(12) United States Patent
Komuro et al.

(10) Patent No.: US 9,005,874 B2
(45) Date of Patent: Apr. 14, 2015

(54) COMPOUND, POLYMERIC COMPOUND, ACID GENERATOR, RESIST COMPOSITION, AND METHOD OF FORMING RESIST PATTERN

(75) Inventors: Yoshitaka Komuro, Kawasaki (JP); Yoshiyuki Utsumi, Kawasaki (JP); Akiya Kawaue, Kawasaki (JP); Masatoshi Arai, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 67 days.

(21) Appl. No.: 13/449,727

(22) Filed: Apr. 18, 2012

(65) Prior Publication Data
US 2012/0270155 A1    Oct. 25, 2012

(30) Foreign Application Priority Data

Apr. 20, 2011   (JP) .................................. 2011-094450

(51) Int. Cl.
| | |
|---|---|
| G03F 7/029 | (2006.01) |
| G03F 7/039 | (2006.01) |
| C07C 69/533 | (2006.01) |
| C08F 220/18 | (2006.01) |
| C07C 381/12 | (2006.01) |
| C07C 309/12 | (2006.01) |
| C07C 309/19 | (2006.01) |
| C07C 309/42 | (2006.01) |
| C07C 309/43 | (2006.01) |
| C07C 311/09 | (2006.01) |
| C07C 311/48 | (2006.01) |
| C07D 307/93 | (2006.01) |
| C07D 493/18 | (2006.01) |
| C08F 220/28 | (2006.01) |
| C08F 228/02 | (2006.01) |
| G03F 7/004 | (2006.01) |
| G03F 7/20 | (2006.01) |

(52) U.S. Cl.
CPC .............. *C07C 381/12* (2013.01); *G03F 7/039* (2013.01); *C07C 309/12* (2013.01); *C07C 309/19* (2013.01); *C07C 309/42* (2013.01); *C07C 309/43* (2013.01); *C07C 311/09* (2013.01); *C07C 311/48* (2013.01); *C07C 2101/08* (2013.01); *C07C 2101/14* (2013.01); *C07C 2102/42* (2013.01); *C07C 2103/74* (2013.01); *C07D 307/93* (2013.01); *C07D 493/18* (2013.01); *C08F 220/28* (2013.01); *C08F 228/02* (2013.01); *G03F 7/0045* (2013.01); *G03F 7/0046* (2013.01); *G03F 7/0397* (2013.01); *G03F 7/2041* (2013.01); *Y10S 430/115* (2013.01); *Y10S 430/122* (2013.01); *Y10S 522/904* (2013.01)

(58) Field of Classification Search
None
See application file for complete search history.

(56) References Cited

U.S. PATENT DOCUMENTS

| 2,631,990 A | 3/1953 | Mack et al. |
| 3,592,655 A * | 7/1971 | Dykstra .................... 430/628 |

(Continued)

FOREIGN PATENT DOCUMENTS

| GB | 1148285 | * 4/1969 |
| JP | A 60-181111 | 9/1985 |

(Continued)

OTHER PUBLICATIONS

Office Action in Japanese Patent Application No. 2011-094450, mailed Jan. 6, 2015.

*Primary Examiner* — Cynthia Hamilton
(74) *Attorney, Agent, or Firm* — Knobbe Martens Olson & Bear LLP

(57) ABSTRACT

There are provided a novel compound, a polymeric compound, a resist composition, an acid generator and a method of forming a resist pattern the compound represented by general formula (1-1):
wherein each of $R^1$ and $R^3$ independently represents a single bond or a divalent linking group; A represents a divalent linking group; each of $R^2$ and $R^4$ independently represents a hydroxyl group, a hydrocarbon group which may have a substituent, or a group represented by general formula (1-an1), (1-an2) or (1-an3), provided that at least one of $R^2$ and $R^4$ represents a group represented by general formula (1-an1), (1-an2) or (1-an3); and n0 is preferably 0 or 1, and
wherein $Y^1$ represents a single bond or $—SO_2—$; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M^+$ represents an organic cation or a metal cation,

[Chemical Formula 1]

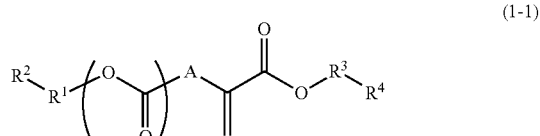

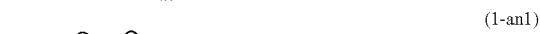

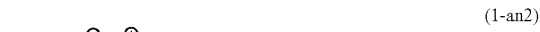

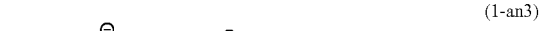

11 Claims, No Drawings

(56) References Cited

U.S. PATENT DOCUMENTS

| | | |
|---|---|---|
| 5,945,517 A | 8/1999 | Nitta et al. |
| 6,153,733 A | 11/2000 | Yukawa et al. |
| 6,444,397 B2 | 9/2002 | Hada et al. |
| 6,949,325 B2 | 9/2005 | Li et al. |
| 7,074,543 B2 | 7/2006 | Iwai et al. |
| 7,482,108 B2 | 1/2009 | Matsumaru et al. |
| 2007/0149702 A1* | 6/2007 | Ando et al. .............. 524/556 |
| 2008/0187860 A1 | 8/2008 | Tsubaki et al. |
| 2009/0317743 A1 | 12/2009 | Shiono et al. |

FOREIGN PATENT DOCUMENTS

| | | |
|---|---|---|
| JP | A 62-213758 | 9/1987 |
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A 2000-302746 | 10/2000 |
| JP | A-2003-241385 | 8/2003 |
| JP | A-2005-336452 | 12/2005 |
| JP | A-2006-045311 | 2/2006 |
| JP | A-2006-259582 | 9/2006 |
| JP | A-2006-317803 | 11/2006 |
| JP | A-2008-292975 | 12/2008 |
| JP | A-2010-002870 | 1/2010 |
| WO | WO 2004/074242 | 9/2004 |
| WO | WO 2009/117729 A2 | 9/2009 |

* cited by examiner

COMPOUND, POLYMERIC COMPOUND, ACID GENERATOR, RESIST COMPOSITION, AND METHOD OF FORMING RESIST PATTERN

BACKGROUND OF THE INVENTION

1. Field of the Invention

The present invention relates to a novel compound, a polymeric compound containing a structural unit derived from the compound, a resist composition containing the polymeric compound, an acid generator including the compound, a resist composition containing the acid generator, and a method of forming a resist pattern using the resist composition.

Priority is claimed on Japanese Patent Application No. 2011-094450, filed Apr. 20, 2011, the content of which is incorporated herein by reference.

2. Description of Related Art

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (and increasing the energy) of the exposure light source. Conventionally, ultraviolet radiation typified by g-line and i-line radiation has been used, but nowadays KrF excimer lasers and ArF excimer lasers are now starting to be introduced in mass production. Furthermore, research is also being conducted into lithography techniques that use an exposure light source having a shorter wavelength (and a higher energy level) than these excimer lasers, such as extreme ultraviolet radiation (EUV), and X-ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base component that exhibits a changed solubility in a developing solution under the action of acid and an acid generator component that generates acid upon exposure.

For example, in the case where the developing solution is an alkali developing solution (namely, an alkali developing process), a positive-type chemically amplified resist composition is typically used, which contains a resin component (base resin) that exhibits increased solubility in an alkali developing solution under the action of acid, and an acid generator component. If the resist film formed using this resist composition is selectively exposed during formation of a resist pattern, then acid is generated from the acid generator component within the exposed portions, and the action of this acid causes an increase in the solubility of the resin component in an alkali developing solution, making the exposed portions soluble in the alkali developing solution. In this manner, the unexposed portions remain to form a positive resist pattern. Here, the base resin uses a resin for which the polarity increases under the action of acid, resulting in an increase in the solubility of the resin in an alkali developing solution, but a decrease in the solubility of the resin within organic solvents. For this reason, if a process that uses a developing solution containing an organic solvent (an organic developing solution) (hereafter, this process is sometimes referred to as "solvent developing process" or "negative developing process") is employed instead of an alkali developing process, then within the exposed portions of the resist film, the solubility in an organic developing solution decreases relatively. As a result, during the solvent developing process, the unexposed portions of the resist film are dissolved and removed by the organic developing solution, whereas the exposed portions remain as a pattern, resulting in the formation of a negative resist pattern. For example, a negative developing process has been proposed in Patent Document 1.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 2).

Furthermore, a multitude of compounds have been proposed as the acid generator used in a chemically amplified resist composition, and examples of known acid generators include onium salt-based acid generators, oxime sulfonate-based acid generators, diazomethane-based acid generators, nitrobenzylsulfonate-based acid generators, iminosulfonate-based acid generators, and disulfone-based acid generators. In recent years, base resins that include a structural unit which functions as an acid generator have also been used (see, for example, Patent Document 3).

DOCUMENTS OF RELATED ART

Patent Document

[Patent Document 1] Japanese Unexamined Patent Application, First Publication No. 2008-292975
[Patent Document 2] Japanese Unexamined Patent Application, First Publication No. 2003-241385
[Patent Document 3] Japanese Unexamined Patent Application, First Publication No. 2006-045311

SUMMARY OF THE INVENTION

In the future, as further progress is made in lithography techniques and miniaturization of resist patterns, further improvement in resist materials has been demanded in terms of various lithography properties such as resolution, line width roughness (LWR) and exposure latitude (EL) margin, and resist pattern shape.

However, when conventional acid generators or structural units functioning as an acid generator as those disclosed in Patent Documents 2 and 3 were used, there was still room for improvement in lithography properties such as resolution, LWR and EL margin, and resist pattern shape.

The present invention takes the above circumstances into consideration, with an object of providing a novel compound useful for acid generation in a resist composition, a polymeric compound containing a structural unit derived from the compound, a resist composition containing the polymeric compound, an acid generator including the compound, a resist composition containing the acid generator, and a method of forming a resist pattern using the resist composition.

For solving the above-mentioned problems, the present invention employs the following aspects.

Namely, a first aspect of the present invention is a compound represented by general formula (1-1) shown below.

[Chemical Formula 1]

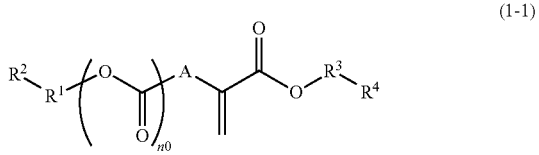

(1-1)

In the formula, each of $R^1$ and $R^3$ independently represents a single bond or a divalent linking group; A represents a divalent linking group; each of $R^2$ and $R^4$ independently represents a hydroxyl group, a hydrocarbon group which may have a substituent, or a group represented by general formula (1-an1), (1-an2) or (1-an3) shown below, provided that at least either one of $R^2$ and $R^4$ represents a group represented by general formula (1-an1), (1-an2) or (1-an3) shown below; and n0 represents 0 or 1.

[Chemical Formula 2]

(1-an1)

(1-an2)

(1-an3)

In the formulas, $Y^1$ represents a single bond or $-SO_2-$; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M^+$ represents an organic cation or a metal cation.

A second aspect of the present invention is a polymeric compound having a structural unit derived from the compound according to the aforementioned first aspect in which the aforementioned $M^+$ represents an organic cation.

A third aspect of the present invention is a resist composition containing a base component (A') that generates acid upon exposure and exhibits changed solubility in a developing solution under the action of acid, wherein the base component (A') contains a polymeric compound (A1') according to the aforementioned second aspect.

A fourth aspect of the present invention is an acid generator including the compound according to the aforementioned first aspect in which the aforementioned $M^+$ represents an organic cation.

A fifth aspect of the present invention is a resist composition containing a base component (A) which exhibits changed solubility in a developing solution under the action of acid and an acid generator component (B) which generates acid upon exposure, wherein the acid generator component (B) contains an acid generator (B1) according to the aforementioned fourth aspect.

A sixth aspect of the present invention is a method of forming a resist pattern, including: forming a resist film on a substrate using the resist composition according to the aforementioned third or fifth aspect; conducting exposure of the resist film; and developing the resist film to form a resist pattern.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon groups, unless otherwise specified.

The term "alkylene group" includes linear, branched or cyclic divalent saturated hydrocarbon groups, unless otherwise specified. The same applies for the alkyl group within an alkoxy group.

A "halogenated alkyl group" is a group in which part or all of the hydrogen atoms of an alkyl group is substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atoms.

The term "structural unit" refers to a monomer unit that contributes to the formation of a polymeric compound (namely, a resin, polymer or copolymer).

An "acrylate ester" is a compound in which the hydrogen atom at the carboxyl group terminal of acrylic acid ($CH_2=CH-COOH$) has been substituted with an organic group.

A "structural unit derived from an acrylate ester" refers to a structural unit that is formed by the cleavage of the ethylenic double bond of an acrylate ester.

Examples of the substituent bonded to the carbon atom on the α-position in the "acrylate ester which may have the hydrogen atom bonded to the carbon atom on the α-position substituted with a substituent" include a halogen atom, an alkyl group of 1 to 5 carbon atoms, a halogenated alkyl group of 1 to 5 carbon atoms and a hydroxyalkyl group. With respect to the "structural unit derived from an acrylate ester", the "α-position (the carbon atom on the α-position)" refers to the carbon atom having the carbonyl group bonded thereto, unless specified otherwise.

Examples of the halogen atom as the substituent which may be bonded to the carbon atom on the α-position include a fluorine atom, a chlorine atom, a bromine atom and an iodine atom.

Specific examples of the alkyl group of 1 to 5 carbon atoms for the substituent which may be bonded to the carbon atom on the α-position include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Further, specific examples of the halogenated alkyl group of 1 to 5 carbon atoms for the substituent include groups in which part or all of the hydrogen atoms of the aforementioned "alkyl group of 1 to 5 carbon atoms for the substituent" are substituted with halogen atoms. Examples of the halogen atom include a fluorine atom, a chlorine atom, a bromine atom and an iodine atom, and a fluorine atom is particularly desirable.

Further, specific examples of the hydroxyalkyl group for the substituent include groups in which part or all of the hydrogen atoms of the aforementioned "alkyl group of 1 to 5 carbon atoms for the substituent" are substituted with hydroxy groups.

In the present invention, it is preferable that a hydrogen atom, an alkyl group of 1 to 5 carbon atoms or a halogenated alkyl group of 1 to 5 carbon atoms is bonded to the carbon atom on the α-position, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

The term "exposure" is used as a general concept that includes irradiation with any form of radiation.

According to the present invention, there are provided a novel compound useful for acid generation in a resist composition, a polymeric compound containing a structural unit derived from the compound, and an acid generator including the compound.

Further, the present invention also provides a resist composition containing either the polymeric compound or the acid generator according to the present invention which exhibits excellent lithography properties (such as resolution, line width roughness (LWR) and exposure latitude (EL) margin) and resist pattern shape, and a method of forming a resist pattern using the resist composition.

DETAILED DESCRIPTION OF THE INVENTION

<<Compound>>

A compound according to the first aspect of the present invention is a compound represented by general formula (1-1) shown below (hereafter, this compound is sometimes referred to as "compound (1-1)").

[Chemical Formula 3]

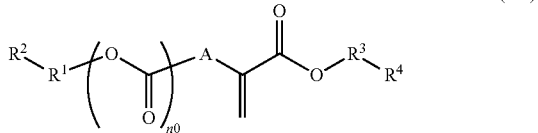

(1-1)

In the formula, each of $R^1$ and $R^3$ independently represents a single bond or a divalent linking group; A represents a divalent linking group; each of $R^2$ and $R^4$ independently represents a hydroxyl group, a hydrocarbon group which may have a substituent, or a group represented by general formula (1-an1), (1-an2) or (1-an3) shown below, provided that at least one of $R^2$ and $R^4$ represents a group represented by general formula (1-an1), (1-an2) or (1-an3) shown below; and n0 represents 0 or 1.

[Chemical Formula 4]

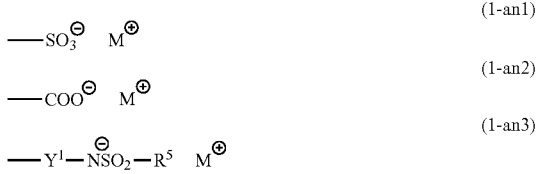

(1-an1)
(1-an2)
(1-an3)

In the formulas, $Y^1$ represents a single bond or $-SO_2-$; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M^+$ represents an organic cation or a metal cation.

In formula (1-1), each of $R^1$ and $R^3$ independently represents a single bond or a divalent linking group.

Preferable examples of the divalent linking group for $R^1$ and $R^3$ include a divalent hydrocarbon group which may have a substituent, and a divalent linking group containing a hetero atom.

Among the above-mentioned examples, in those cases where $R^2$ or $R^4$ that are bonded to the $R^1$ and $R^3$ groups represent a hydroxyl group or a cyclic group which may have a substituent, as the divalent linking group for $R^1$ and $R^3$, a divalent linking group containing a hetero atom is preferable. Further, in those cases where $R^2$ and $R^4$ that are bonded to the $R^1$ and $R^3$ groups represent any one of the groups represented by the above formulas (1-an1), (1-an2) and (1-an3), as the divalent linking group for $R^1$ and $R^3$, a divalent hydrocarbon group which may have a substituent is preferable. The $R^2$ and $R^4$ groups will be described later in more detail.

Here, the description that the hydrocarbon group "may have a substituent" means that part or all of the hydrogen atoms within the hydrocarbon group may be substituted with an atom other than a hydrogen atom or with a group.

The hydrocarbon group may be either an aliphatic hydrocarbon group, or an aromatic hydrocarbon group.

An "aliphatic hydrocarbon group" refers to a hydrocarbon group that has no aromaticity.

Further, the aliphatic hydrocarbon group may be either saturated or unsaturated. In general, the aliphatic hydrocarbon group is preferably saturated.

As specific examples of the aliphatic hydrocarbon group for the hydrocarbon group as $R^1$ and $R^3$, a linear, branched or cyclic aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8 carbon atoms, still more preferably 1 to 4 carbon atoms, and most preferably 1 to 3 carbon atoms.

As the linear aliphatic hydrocarbon group, a linear alkylene group is preferable. Specific examples thereof include a methylene group $[-CH_2-]$, an ethylene group $[-(CH_2)_2-]$, a trimethylene group $[-(CH_2)_3-]$, a tetramethylene group $[-(CH_2)_4-]$ and a pentamethylene group $[-(CH_2)_5-]$.

As the branched aliphatic hydrocarbon group, branched alkylene groups are preferred, and specific examples include various alkylalkylene groups, including alkylmethylene groups such as $-CH(CH_3)-$, $-CH(CH_2CH_3)-$, $-C(CH_3)_2-$, $-C(CH_3)(CH_2CH_3)-$, $-C(CH_3)(CH_2CH_2CH_3)-$, and $-C(CH_2CH_3)_2-$; alkylethylene groups such as $-CH(CH_3)CH_2-$, $-CH(CH_3)CH(CH_3)-$, $-C(CH_3)_2CH_2-$, $-CH(CH_2CH_3)CH_2-$, and $-C(CH_2CH_3)_2-CH_2-$; alkyltrimethylene groups such as $-CH(CH_3)CH_2CH_2-$, and $-CH_2CH(CH_3)CH_2-$; and alkyltetramethylene groups such as $-CH(CH_3)CH_2CH_2CH_2-$, and $-CH_2CH(CH_3)CH_2CH_2-$. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (=O).

Among the above-mentioned examples, as the chain-like aliphatic hydrocarbon group, the aforementioned linear or branched alkylene groups or the aforementioned linear or branched alkylene groups in which part or all of the hydrogen atoms have been substituted with fluorine atoms (namely, fluorinated alkylene groups) are preferred. Specific examples of such fluorinated alkylene groups include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CF_2CH_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$— and —$C(CF_3)_2CH_2$—.

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O). Examples of the cyclic aliphatic hydrocarbon group having a substituent include camphor having an oxygen atom.

Examples of the aforementioned aromatic hydrocarbon group for the hydrocarbon group as $R^1$ and $R^3$ include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O), and a fluorine atom is particularly desirable.

Further, as the hydrocarbon group for $R^1$ and $R^3$, groups in which the aromatic hydrocarbon group is bonded to the terminal of the aforementioned chain-like aliphatic hydrocarbon group or interposed within the chain of a chain-like aliphatic hydrocarbon group are also preferable.

When $R^1$ or $R^3$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, "-$A^R$-O—$B^R$— (wherein O is an oxygen atom, and each of $A^R$ and $B^R$ independently represents a divalent hydrocarbon group which may have a substituent)" and a combination of a divalent hydrocarbon group which may have a substituent with a divalent linking group containing a hetero atom. As examples of the divalent hydrocarbon group which may have a substituent, the same groups as those described above for the hydrocarbon group which may have a substituent can be given, and a linear or branched aliphatic hydrocarbon group or an aliphatic hydrocarbon group containing a ring in the structure thereof is preferable.

When $R^1$ or $R^3$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $R^1$ or $R^3$ is "-$A^R$-O—$B^R$—", each of $A^R$ and $B^R$ independently represents a divalent hydrocarbon group which may have a substituent.

The hydrocarbon group for $A^R$ may be either an aliphatic hydrocarbon group, or an aromatic hydrocarbon group. An "aliphatic hydrocarbon group" refers to a hydrocarbon group that has no aromaticity.

The aliphatic hydrocarbon group for $A^R$ may be either saturated or unsaturated. In general, the aliphatic hydrocarbon group is preferably saturated.

As specific examples of the aliphatic hydrocarbon group for $A^R$, a linear or branched aliphatic hydrocarbon group, and an aliphatic hydrocarbon group having a ring in the structure thereof can be given. These are the same as defined above.

Among these, $A^R$ is preferably a linear aliphatic hydrocarbon group, more preferably a linear alkylene group, still more preferably a linear alkylene group of 2 to 5 carbon atoms, and most preferably an ethylene group.

As the hydrocarbon group for $B^R$, the same divalent hydrocarbon groups as those described above for $A^R$ can be used.

As $B^R$, a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Among the above-mentioned examples, in those cases where $R^2$ or $R^4$ that are bonded to the $R^1$ and $R^3$ groups represent a hydroxyl group or a cyclic group which may have a substituent, as the divalent linking group for $R^1$ and $R^3$, as described above, a divalent linking group containing a hetero atom is preferable, and a divalent linking group containing an oxygen atom as a hetero atom is more preferable.

Further, in those cases where $R^2$ and $R^4$ that are bonded to the $R^1$ and $R^3$ groups represent any one of the groups represented by the above formulas (1-an1), (1-an2) and (1-an3), as the divalent linking group for $R^1$ and $R^3$, as described above, a divalent hydrocarbon group which may have a substituent is preferable, and a fluorinated alkylene group of 1 to 4 carbon atoms which may have a substituent, an alkylene group of 1 to 4 carbon atoms which may have a substituent, or an aliphatic hydrocarbon group or aromatic hydrocarbon group which contains a ring in the structure thereof and which may have a substituent is more preferable.

In formula (1-1), each of $R^2$ and $R^4$ independently represents a hydroxyl group, a hydrocarbon group which may have a substituent, or a group represented by the aforementioned general formula (1-an1), (1-an2) or (1-an3).

As examples of the hydrocarbon group for $R^2$ and $R^4$ which may have a substituent, the same hydrocarbon groups as those described above for $R^1$ and $R^3$ can be given, and an aliphatic cyclic group which may have a substituent is preferable.

If $R^2$ or $R^4$ represents a hydrocarbon group, it is preferable because when the compound (1-1) is used as the acid generator according to the fourth aspect, the solubility thereof in a component (S) can be improved.

If $R^2$ or $R^4$ represents a hydrocarbon group having a substituent, it is thought that when the compound (1-1) is used as the acid generator according to the fourth aspect, the interaction with the polar moiety within the component (A) or component (A') described later becomes stronger, and is therefore preferable.

The aliphatic cyclic group for $R^2$ and $R^4$ which may have a substituent may be either a monocyclic group or a polycyclic group. The alicyclic group has 3 to 30 carbon atoms, preferably 5 to 30 carbon atoms, more preferably 5 to 20 carbon atoms, still more preferably 6 to 15 carbon atoms, and most preferably 6 to 12 carbon atoms.

Examples of the alicyclic group include groups in which one or more hydrogen atoms have been removed from a monocycloalkane, and groups in which one or more hydrogen atoms have been removed from a polycycloalkane such as a bicycloalkane, tricycloalkane or tetracycloalkane. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 5]

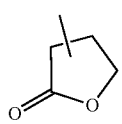

(L1)

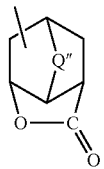

(L2)

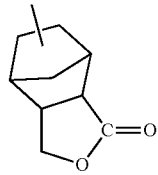

(L3)

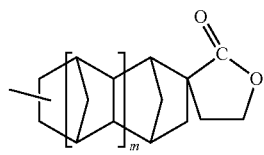

(L4)

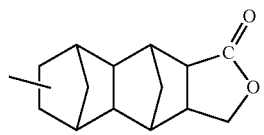

(L5)

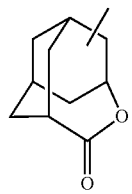

(L6)

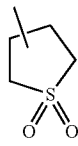

(S1)

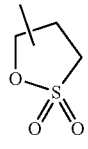

(S2)

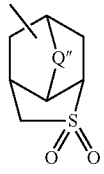

(S3)

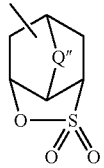

(S4)

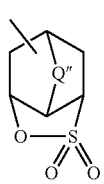

In the formulas, Q″ represents an alkylene group of 1 to 5 carbon atoms, —O—, —S—, —O—$R^{94}$— or —S—$R^{95}$—

(wherein each of $R^{94}$ and $R^{95}$ independently represents an alkylene group of 1 to 5 carbon atoms); and m represents an integer of 0 or 1.

In the formulas, examples of the alkylene group for Q", $R^{94}$ and $R^{95}$ include a methylene group [—$CH_2$—]; an alkylmethylene group such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$— or —$C(CH_2CH_3)_2$—; an ethylene group [—$CH_2CH_2$—]; an alkylethylene group such as —$CH(CH_3)CH_2$—, —$CH(CH_3)CH(CH_3)$—, —$C(CH_3)_2CH_2$— or —$CH(CH_2CH_3)CH_2$—; a trimethylene group (an n-propylene group) [—$CH_2CH_2CH_2$—]; an alkyltrimethylene group such as —$CH(CH_3)CH_2CH_2$— or —$CH_2CH(CH_3)CH_2$—; a tetramethylene group [—$CH_2CH_2CH_2CH_2$—]; an alkyltetramethylene group such as —$CH(CH_3)CH_2CH_2CH_2$— or —$CH_2CH(CH_3)CH_2CH_2$—; and a pentamethylene group [—$CH_2CH_2CH_2CH_2CH_2$—].

In these aliphatic cyclic groups, part of the hydrogen atoms bonded to the carbon atoms constituting the ring structure may be substituted with a substituent. Examples of the substituent include an alkyl group, an alkoxy group, a halogen atom, a halogenated alkyl group, a hydroxyl group and an oxygen atom (═O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

Further, the above hydrocarbon group may be an acid dissociable group which may be cleaved by the action of acid.

Specific examples of the case where $R^2$ and $R^4$ represent an acid dissociable group include:

(1) a case where $R^1$ or $R^3$ which is bonded to these $R^2$ and $R^4$ groups has a single bond or —C(═O)O— at the terminal thereof, and a tertiary carbon atom constituted by the $R^2$ and $R^4$ groups is bonded to the terminal oxygen atom of this $R^1$ or $R^3$ group, so that this $R^1$ or $R^3$ group becomes a tertiary alkyl ester-type acid dissociable group described later; and (2) a case where $R^1$ or $R^3$ which is bonded to these $R^2$ and $R^4$ groups has —C(═O)—O—(C)($R^{O1}$)($R^{O2}$)—O— (in the formula, each of $R^{O1}$ and $R^{O2}$ independently represents a hydrogen atom or an alkyl group of 1 to 5 carbon atoms) or —(C)($R^{O1}$)($R^{O2}$)—O— (in the formula, $R^{O1}$ and $R^{O2}$ are the same as defined above) at the terminal thereof, and the hydrocarbon group for the $R^2$ and $R^4$ groups is bonded to the terminal oxygen atom of this $R^1$ or $R^3$ group to form an acetal-type acid dissociable group described later.

These tertiary alkyl ester-type acid dissociable groups and acetal-type acid dissociable groups will be described later in more detail within the description for the resist composition.

If $R^2$ and $R^4$ represent an acid dissociable group, it is preferable because when the compound (1-1) is used in a resist composition, not only the compound (1-1) functions as an acid generator but the solubility thereof in a developing solution is also changed by the action of acid.

Further, if $R^2$ and $R^4$ represent an acid dissociable group, it is preferable because when the compound (1-1) is used as the acid generator according to the fourth aspect, the molecular weight of anion moiety of this acid dissociable group varies before and after the dissociation to thereby change the length of acid diffusion.

At least either one of $R^2$ and $R^4$ represents a group represented by general formula (1-an1), (1-an2) or (1-an3) shown below. The groups represented by formulas (1-an1) to (1-an3) will be described below in more detail.

[Chemical Formula 6]

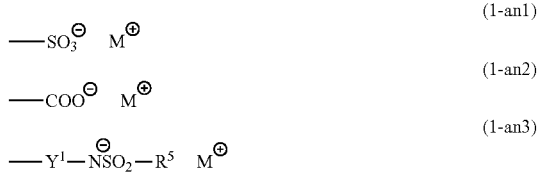

In the formulas, $Y^1$ represents a single bond or —$SO_2$—; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M^+$ represents an organic cation or a metal cation.

In formulas (1-an1) to (1-an3), $M^+$ represents an organic cation or a metal cation.

As the organic cation for $M^+$, there is no particular limitation, and any of those conventionally known as cation moiety for an onium salt-based acid generator of resist compositions can be used.

For example, as the organic cation for $M^+$, a cation moiety represented by general formula (c-1) or (c-2) show below can be used.

[Chemical Formula 7]

In the formulas, each of $R^{1'''}$ to $R^{3'''}$, $R^{5'''}$ and $R^{6'''}$ independently represents an aryl group or an alkyl group; two of $R^{1'''}$ to $R^{3'''}$ in formula (c-1) may be mutually bonded to form a ring with the sulfur atom in the formula.

In formula (c-1), $R^{1'''}$ to $R^{3'''}$ each independently represents an aryl group or an alkyl group. In formula (c-1), two of $R^{1'''}$ to $R^{3'''}$ may be bonded to each other to form a ring with the sulfur atom in the formula.

Further, among $R^{1'''}$ to $R^{3'''}$, it is preferable that at least one group represent an aryl group. It is more preferable that among $R^{1'''}$ to $R^{3'''}$, two or more groups represent aryl groups, and it is particularly desirable that all of $R^{1'''}$ to $R^{3'''}$ represent aryl groups.

The aryl group for $R^{1'''}$ to $R^{3'''}$ is not particularly limited. For example, an aryl group having 6 to 20 carbon atoms may be used, in which some or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group with which hydrogen atoms of the aryl group may be substituted is preferably an alkyl group having 1 to 5 carbon atoms, and most preferably a methyl group, an ethyl group, a propyl group, an n-butyl group, or a tert-butyl group.

The alkoxy group with which hydrogen atoms of the aryl group may be substituted is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom with which hydrogen atoms of the aryl group may be substituted is preferably a fluorine atom.

The alkyl group for $R^{1''}$ to $R^{3''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1''}$ to $R^{3''}$ in formula (c-1) are bonded to each other to form a ring with the sulfur atom shown in the formula, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom.

When two of $R^{1''}$ to $R^{3''}$ in formula (c-1) are bonded to each other to form a ring with the sulfur atom shown in the formula, the remaining one of $R^{1''}$ to $R^{3''}$ is preferably an aryl group. As examples of the aryl group, the same as the above-mentioned aryl groups for $R^{1''}$ to $R^{3''}$ can be given.

Preferred examples of the cation moiety represented by formula (c-1) include cation moieties represented by formulas (I-1-1) to (I-1-32) shown below.

[Chemical Formula 8]

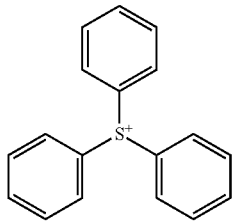
(I-1-1)

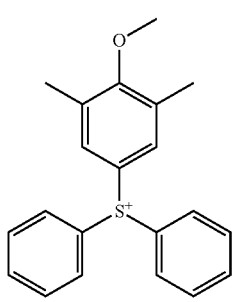
(I-1-2)

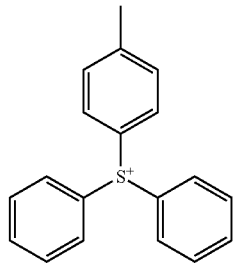
(I-1-3)

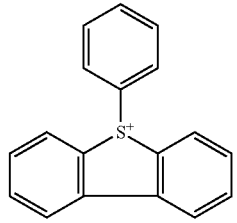
(I-1-4)

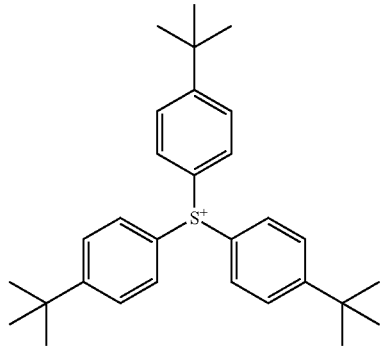
(I-1-5)

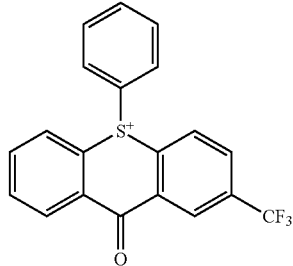
(I-1-6)

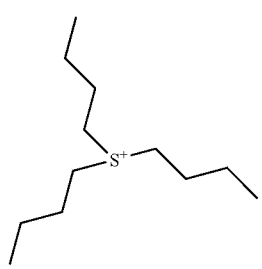
(I-1-7)

[Chemical Formula 9]

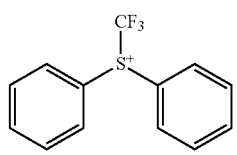
(I-1-8)

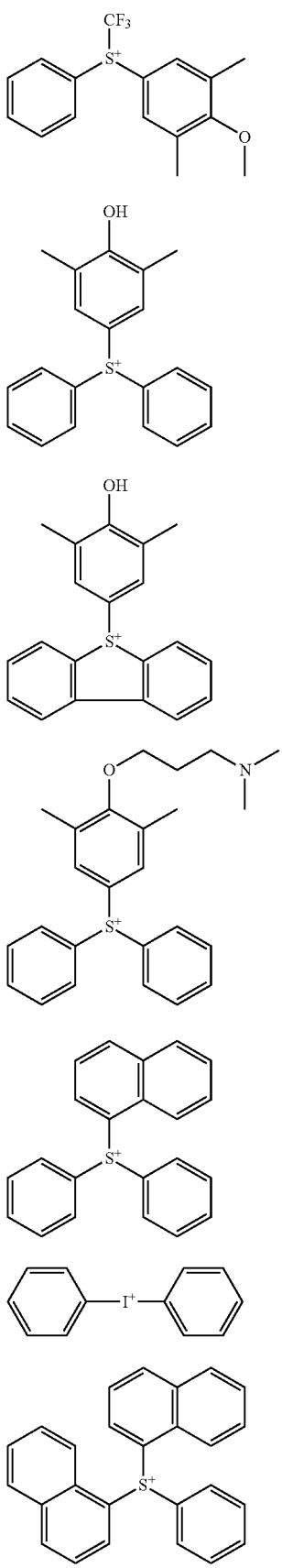
(I-1-9)
(I-1-10)
(I-1-11)
(I-1-12)
(I-1-13)
(I-1-14)
(I-1-15)
[Chemical Formula 10]
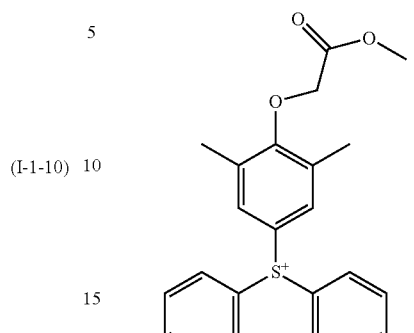
(I-1-16)
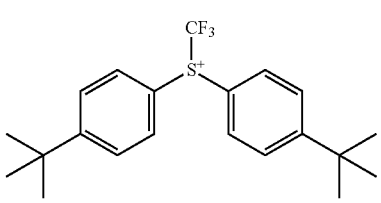
(I-1-17)
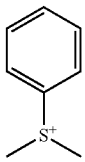
(I-1-18)
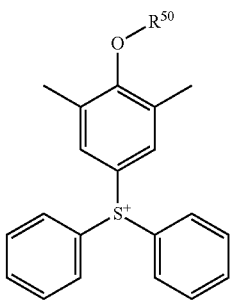
(I-1-19)
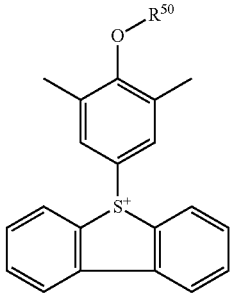
(I-1-20)

(I-1-21)
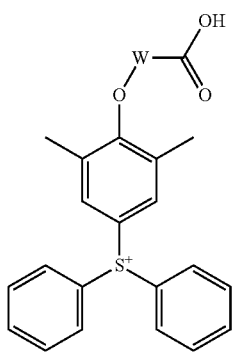
(I-1-22)
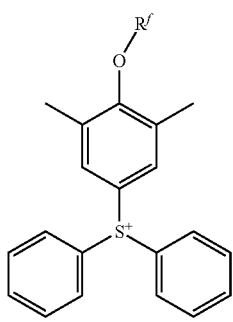
[Chemical Formula 11]
(I-1-23)
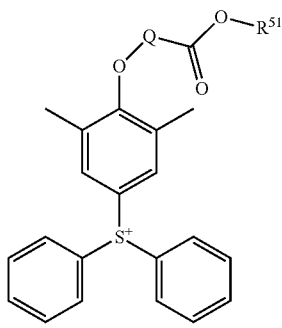
(I-1-24)
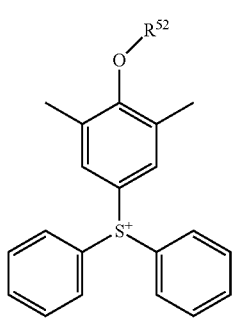
(I-1-25)
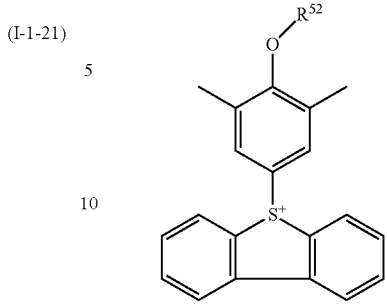
(I-1-26)
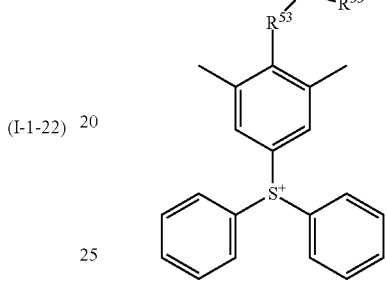
(I-1-27)
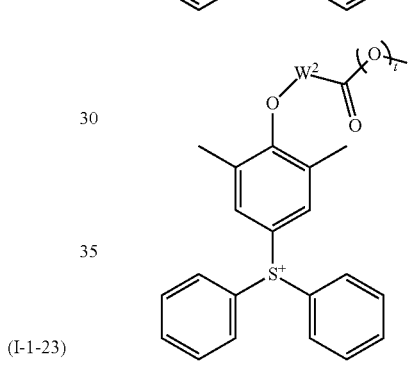
[Chemical Formula 12]
(I-1-28)
(I-1-29)
(I-1-30)
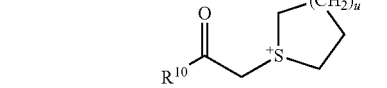
(I-1-31)
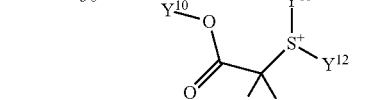
(I-1-32)
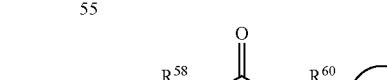
In formulas (I-1-19) and (I-1-20), $R^{50}$ represents a group containing an acid dissociable, dissolution inhibiting group, and preferably a group represented by formula (p1), (p1-1) or (p2) within the description for the resist composition described later, or a group in which any one of the groups represented by the after-mentioned formulas (1-1) to (1-9) and (2-1) to (2-6) as an aliphatic cyclic group is bonded to the oxygen atom of —$R^{91}$—C(=O)—O—. Here, $R^{91}$ represents a single bond or a linear or branched alkylene group, and the alkylene group preferably has 1 to 5 carbon atoms.

In formula (I-1-21), W represents a divalent linking group, and the same divalent linking groups as those described above for $R^1$ and $R^3$ can be used. Among these, a linear or branched alkylene group, a divalent aliphatic cyclic group or a group containing a hetero atom is preferable, a linear or branched alkylene group is more preferable, and a linear alkylene group is still more preferable.

In formula (I-1-22), $R^f$ represents a fluorinated alkyl group, i.e., a group in which an unsubstituted alkyl group has part or all of the hydrogen atoms substituted with fluorine atoms. The unsubstituted alkyl group is preferably a linear or branched alkyl group, and more preferably a linear alkyl group.

In formula (I-1-23), Q represents a divalent linking group, and $R^{51}$ represents a carbonyl group, an ester bond or an organic group having a sulfonyl group.

Examples of the divalent linking group for Q include the same divalent linking groups as those described above for $R^1$ and $R^3$. The divalent linking group is preferably an alkylene group or a divalent linking group containing an ester bond (—C(=O)—O—), and in particular, an alkylene group or —$R^{92}$—C(=O)—O—$R^{93}$— (each of $R^{92}$ and $R^{93}$ independently represents an alkylene group) is more preferable.

The carbonyl group, ester bond or organic group having a sulfonyl group for $R^{51}$ may be either an aromatic hydrocarbon group or an aliphatic hydrocarbon group. Examples of the aromatic hydrocarbon group and the aliphatic hydrocarbon group include the same groups as those described above for $R^1$ and $R^3$. Of these, as the carbonyl group, ester bond or organic group having a sulfonyl group for $R^{51}$, aliphatic hydrocarbon groups are preferable, and in particular, bulky aliphatic hydrocarbon groups are more preferable, and cyclic saturated hydrocarbon groups are still more preferable. As preferable examples of $R^{51}$, groups represented by the aforementioned formulas (L1) to (L6) and (S1) to (S4), and groups in which the hydrogen atom bonded to a monocyclic group or polycyclic group has been substituted with an oxygen atom (=O) can be given.

In formulas (I-1-24) and (I-1-25), $R^{52}$ represents an alkyl group of 4 to 10 carbon atoms which is not an acid dissociable group. As $R^{52}$, a linear or branched alkyl group is preferable, and a linear alkyl group is more preferable.

In formula (I-1-26), $R^{53}$ represents a divalent group having a base dissociable portion, $R^{54}$ represents a divalent linking group, and $R^{55}$ represents a group having an acid dissociable group.

Here, the "base dissociable portion" of $R^{53}$ refers to a portion which is dissociated by the action of an alkali developing solution (more specifically, a 2.38% by weight aqueous solution of tetramethylammonium hydroxide at 23° C.). When the base dissociable portion is dissociated, the solubility in an alkali developing solution increases. As an alkaline developing solution, those that are generally used in the field of lithography may be used. It is preferable that the base dissociable portion is dissociated by the action of a 2.38% by weight aqueous solution of tetramethylammonium hydroxide at 23° C.

Further, $R^{53}$ may be a group constituted only by the base dissociable portion or may be a group constituted by the base dissociable portion and a group or atom bonded thereto which does not dissociate by a base.

An ester bond (—C(=O)—O—) is most preferred as the base dissociable portion of $R^{53}$.

As the examples of a group or atom included in $R^{53}$ which does not dissociate by a base, the same divalent linking groups as those described above for $R^1$ and $R^3$, and a combination of these linking groups (excluding those that are dissociated by a base) can be mentioned. Here, the expression "combination of these linking groups" refers to a divalent group constituted by linking groups that are bonded to each other. Of these, a combination of an alkylene group with a divalent linking group containing a hetero atom is particularly desirable. However, it is preferable that the hetero atom is not positioned adjacent to the atom which is forming a bond to be cleaved by the action of a base within the base dissociable portion.

Examples of the alkylene groups include the same linear or branched alkylene groups as those described above for $R^1$ and $R^3$.

Further, it is particularly desirable that the hetero atom is an oxygen atom.

Among the above examples, $R^{53}$ is preferably a group constituted by the base dissociable portion and a group or atom bonded thereto which does not dissociate by a base.

$R^{54}$ represents a divalent linking group, and examples thereof include the same divalent linking groups as those described above for $R^1$ and $R^3$. Among these, an alkylene group or a divalent aliphatic cyclic group is preferable, and an alkylene group is particularly desirable.

$R^{55}$ represents a group having an acid dissociable group.

Here, an acid dissociable group refers to an organic group which may be dissociated by the action of acid, and there is no particular limitation as long as it is a group that satisfies this definition. Examples thereof include acid dissociable, dissolution inhibiting groups which have been proposed for the base resin of a conventional chemically amplified resist. Specific examples thereof are the same as the acid dissociable, dissolution inhibiting groups as those described above in connection with the structural unit (a1), and include cyclic or chain-like tertiary alkyl ester-type acid dissociable groups; and acetal-type acid dissociable groups such as alkoxyalkyl groups. Among these, tertiary alkyl ester-type acid dissociable groups are preferable.

Further, a "group having an acid dissociable group" may be an acid dissociable group itself, or may be a group constituted by an acid dissociable group and a group or atom bonded thereto which does not dissociate by an acid (namely, a group or atom which remains to be bonded to an acid generator even after dissociation of the acid dissociable group). Here, as the examples of a group or atom which does not dissociate by an acid, the same divalent linking groups as those described above for $R^1$ and $R^2$ can be mentioned.

In formula (I-1-27), $W^2$ represents a single bond or a divalent linking group, t represents 0 or 1, and $R^{62}$ represents a group which is not dissociable by acid (hereafter, referred to as "acid non-dissociable group").

Examples of the divalent linking group for $W^2$ include the same divalent linking groups as those described above for $R^1$ and $R^3$. Of the above possibilities, $W^2$ is preferably a single bond.

t is preferably 0.

The acid non-dissociable group for $R^{62}$ is not particularly limited as long as it is a group which is not dissociable by the action of acid. The acid non-dissociable group is preferably an acid non-dissociable hydrocarbon group which may have a substituent, more preferably a cyclic hydrocarbon group which may have a substituent, and still more preferably a group in which one hydrogen atom has been removed from adamantane.

In formulas (I-1-28) and (I-1-29), each of $R^9$ and $R^{10}$ independently represents a phenyl group or naphthyl group which may have a substituent, an alkyl group of 1 to 5 carbon atoms, an alkoxy group or a hydroxyl group. u is an integer of 1 to 3, and most preferably 1 or 2.

In formula (I-1-30), $Y^{10}$ represents a cyclic hydrocarbon group of 5 or more carbon atoms which may have a substituent and is an acid dissociable group which may be dissociated by the action of acid; each of $R^{56}$ and $R^{57}$ independently represents a hydrogen atom, an alkyl group or an aryl group, and $R^{56}$ and $R^{57}$ may be bonded to each other to form a ring; and each of $Y^{11}$ and $Y^{12}$ independently represents an alkyl group or an aryl group, and $Y^{11}$ and $Y^{12}$ may be bonded to each other to form a ring.

$Y^{10}$ represents a cyclic hydrocarbon group of 5 or more carbon atoms which may have a substituent and is an acid dissociable group which may be dissociated by the action of acid. By virtue of $Y^{10}$ representing a cyclic hydrocarbon group of 5 or more carbon atoms which is an acid dissociable group and may be dissociated by the action of acid, various lithography properties (such as resolution, line width roughness (LWR) and exposure latitude (EL margin)) and resist pattern shape can be improved.

Examples of $Y^{10}$ include groups to form a cyclic tertiary alkyl ester with —C($R^{56}$)($R^{57}$)—C(=O)—O—.

The term "tertiary alkyl ester" as used herein indicates a structure in which the tertiary carbon atom in a cyclic hydrocarbon group of 5 or more carbon atoms is bonded to the terminal oxygen atom of —C($R^{56}$)($R^{57}$)—C(=O)—O—. In this tertiary alkyl ester, the action of acid causes cleavage of the bond between the oxygen atom and the tertiary carbon atom.

The cyclic hydrocarbon group may have a substituent, and the number of carbon atoms within this substituent is not included in the number of carbon atoms referred to as "5 or more carbon atoms".

Examples of the "aliphatic cyclic group" include a monocyclic group or polycyclic group that has no aromaticity, and a polycyclic group is preferred.

The "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

Examples of aliphatic cyclic groups include groups in which two or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group. Specific examples include groups in which two or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

Each of $R^{56}$ and $R^{57}$ independently represents a hydrogen atom, an alkyl group or an aryl group.

Examples of the alkyl group and aryl group for $R^{56}$ and $R^{57}$ include the same alkyl groups and aryl groups as those described above for $R^{1'''}$ to $R^{3'''}$, respectively. Further, $R^{56}$ and $R^{57}$ may be bonded to each other to form a ring in the same manner as that of $R^{1'''}$ to $R^{3'''}$ described above.

Of the various possibilities described above, it is particularly desirable that $R^{57}$ and $R^{56}$ are both hydrogen atoms.

Each of $Y^{11}$ and $Y^{12}$ independently represents an alkyl group or an aryl group.

Examples of the alkyl group and aryl group for $Y^{11}$ and $Y^{12}$ include the same alkyl groups and aryl groups as those described above for $R^{1'''}$ to $R^{3'''}$, respectively.

Among these, it is particularly desirable that each of $Y^{11}$ and $Y^{12}$ represent a phenyl group or a naphthyl group. Further, $Y^{11}$ and $Y^{12}$ may be bonded to each other to form a ring in the same manner as that of $R^{1'''}$ to $R^{3'''}$ described above.

In formula (I-1-31), $R^{58}$ represents an aliphatic cyclic group; $R^{59}$ represents a single bond or an alkylene group which may have a substituent; $R^{60}$ represents an arylene group which may have a substituent; and $R^{61}$ represents an alkylene group of 4 or 5 carbon atoms which may have a substituent.

The aliphatic cyclic group for $R^{58}$ may be either a monocyclic group or a polycyclic group, although it is preferably a polycyclic group, is more preferably a group in which one or more hydrogen atoms have been removed from a polycycloalkane, and is most preferably a group in which one or more hydrogen atoms have been removed from adamantane.

The alkylene group for $R^{59}$ which may have a substituent is preferably a linear or branched alkylene group, and in particular, a single bond or an alkylene group of 1 to 3 carbon atoms is preferred.

The arylene group for $R^{60}$ preferably has 6 to 20 carbon atoms, more preferably 6 to 14 carbon atoms, and still more preferably 6 to 10 carbon atoms. Examples of the arylene group include a phenylene group, a biphenylene group, a fluorenylene group, a naphthylene group, an anthrylene group and a phenanthrylene group, and a phenylene group or a naphthylene group is preferred because it can be synthesized at a low cost.

In formula (I-1-32), $R^{1'''}$ represents an arylene group or an alkylene group; each of $R^{2'''}$ and $R^{3'''}$ independently represents an aryl group or an alkyl group, and $R^{2'''}$ and $R^{3'''}$ may be mutually bonded to form a ring with the sulfur atom shown in the formula; at least one of $R^{1'''}$ to $R^{3'''}$ represents an arylene group or an aryl group; $W^1$ represents a linking group having a valency of n, wherein n represents 2 or 3.

The arylene group for $R^{1'''}$ is not particularly limited and includes, for example, an arylene group having 6 to 20 carbon atoms in which part or all of the hydrogen atoms of the arylene group may be substituted. The alkylene group for $R^{1'''}$ is not particularly limited and includes, for example, a linear, branched or cyclic alkylene group having 1 to 10 carbon atoms.

The aryl group for $R^{2'''}$ and $R^{3'''}$ is not particularly limited and includes, for example, an aryl group having 6 to 20 carbon atoms in which part or all of the hydrogen atoms of the aryl group may be substituted. The alkyl group for $R^{2'''}$ and $R^{3'''}$ is not particularly limited and includes, for example, a linear, branched or cyclic alkyl group having 1 to 10 carbon atoms.

Examples of the divalent linking group for $W^1$ include the same divalent linking groups as those described above for $R^1$ and $R^2$. The divalent linking group may be linear, branched or cyclic, although a cyclic divalent linking group is preferred. In particular, a group that combines two carbonyl groups at both ends of the arylene group is preferred.

As a trivalent linking group for $W^1$, a group in which three carbonyl groups are combined with an arylene group is preferred.

In formula (c-2), $R^{5'''}$ and $R^{6'''}$ each independently represents an aryl group or alkyl group. At least one of $R^{5'''}$ and $R^{6'''}$ represents an aryl group. It is preferable that both of $R^{5'''}$ and $R^{6'''}$ represent an aryl group.

Examples of the aryl group for $R^{5'''}$ and $R^{6'''}$ include the same aryl groups as those described for $R^{1'''}$ to $R^{3'''}$.

Examples of the alkyl group for $R^{5'''}$ and $R^{6'''}$ include the same alkyl groups as those described for $R^{1'''}$ to $R^{3'''}$.

It is particularly desirable that both of $R^{5'''}$ and $R^{6'''}$ represents a phenyl group.

Alternatively, as the organic cation for $M^+$, an organic cation represented by general formula (c-3) shown below may also be used.

[Chemical Formula 13]

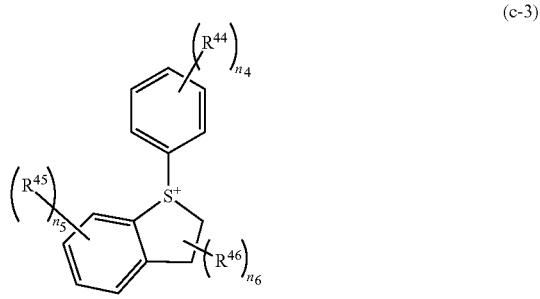

(c-3)

In the formula, each of $R^{44}$ to $R^{46}$ independently represents an alkyl group, an acetyl group, an alkoxy group, a carboxy group, a hydroxyl group or a hydroxyalkyl group; each of $n_4$ and $n_5$ independently represents an integer of 0 to 3; and $n_6$ represents an integer of 0 to 2.

With respect to $R^{44}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{44}$ to $R^{46}$ group, as indicated by the corresponding value of $n_1$ to $n_6$, then the two or more of the individual $R^{44}$ to $R^{46}$ group may be the same or different from each other.

$n_4$ is preferably 0 to 2, and more preferably 0 or 1.
$n_5$ is preferably 0 or 1, and more preferably 0.
$n_6$ is preferably 0 or 1, and more preferably 1.

In the present invention, as the organic cation for $M^+$, an organic cation represented by the aforementioned general formula (c-1) or (c-3) is preferred.

There are no particular limitations on the metal cation for $M^+$, although an alkali metal ion is preferable. Specific examples thereof include a sodium ion, a lithium ion and a potassium ion, and a sodium ion or a lithium ion is more preferable.

In formula (1-an3), $Y^1$ represents a single bond or —$SO_2$—. It is preferable if $Y^1$ represents a single bond when the resist composition according to the third or fifth aspect is prepared, since the resist pattern shape improves. On the other hand, it is preferable if $Y^1$ represents —$SO_2$— because the resolution improves.

In formula (1-an3), $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom.

Specific examples of the linear or branched monovalent hydrocarbon group of 1 to 10 carbon atoms for $R^5$ include linear alkyl groups such as a methyl group, an ethyl group, a propyl group, a butyl group, a pentyl group, a hexyl group, a heptyl group, an octyl group, a nonyl group and a decyl group; and branched alkyl groups such as a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group. The linear or branched monovalent hydrocarbon group may or may not be substituted with a fluorine atom, although a fluorinated alkyl group is preferable, a group in which all of the hydrogen atoms constituting a linear alkyl group have been substituted with fluorine atoms (namely, a perfluoroalkyl group) is more preferable, and a trifluoromethyl group is particularly desirable.

As the cyclic monovalent hydrocarbon group of 3 to 20 carbon atoms for $R^5$, an aliphatic cyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable.

The cyclic monovalent hydrocarbon group may or may not be substituted with a fluorine atom.

Examples of the monovalent hydrocarbon group of 3 to 20 carbon atoms for $R^5$ having a cyclic partial structure include a group in which the "cyclic monovalent hydrocarbon group" described above is bonded to a group having one hydrogen atom further removed from the "linear or branched monovalent hydrocarbon group" described above.

The cyclic monovalent hydrocarbon group having a cyclic partial structure may or may not be substituted with a fluorine atom.

Both of $R^2$ and $R^4$ may be a group represented by the aforementioned general formula (1-an1), (1-an2) or (1-an3). When both of $R^2$ and $R^4$ represent a group represented by the aforementioned general formula (1-an1), (1-an2) or (1-an3), for example, the acid generating ability of the structural unit (a0) in the polymeric compound according to the second aspect or in the acid generator according to the fourth aspect can be relatively increased.

In the present invention, it is preferable that only one of $R^2$ and $R^4$ represent a group represented by the aforementioned general formula (1-an1), (1-an2) or (1-an3), and it is more preferable that only one of $R^2$ and $R^4$ represent a group represented by the aforementioned general formula (1-an1), (1-an2) or (1-an3) while the other represents a hydrocarbon group which may have a substituent (and particularly preferably an aliphatic cyclic group which may have a substituent). Suitable properties for use as a resist composition can be improved by providing different properties within the same structural unit or within the same molecule.

In formula (1-1), A represents a divalent linking group.
Examples of the divalent linking group for A include the same divalent linking groups as those described above for $R^1$ and $R^3$, and a divalent hydrocarbon group which may have a substituent is preferable, a linear or branched aliphatic hydrocarbon group is more preferable, and a methylene group, an ethylene group or a trimethylene group is particularly desirable.

In formula (1-1), n0 represents 0 or 1. When n0 represents 0, this means that the moiety in the parenthesis ( ) indicates a single bond. In particular, n0 is preferably 1.

As the compound of the present invention, compounds shown in the following general formulas (1-1-1) to (1-1-18) are preferable, and compounds shown in the following general formulas (1-1-1) to (1-1-6) are more preferable.

In the formulas shown below, $M^+$ is the same as defined above.

[Chemical Formula 14]

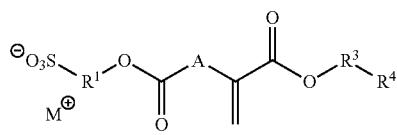
(1-1-1)

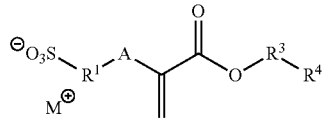
(1-1-2)

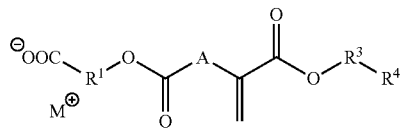
(1-1-3)

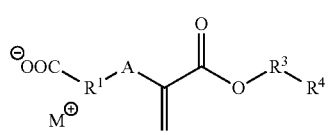
(1-1-4)

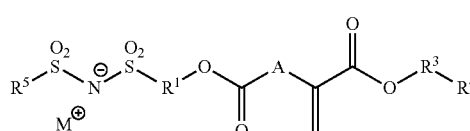
(1-1-5)

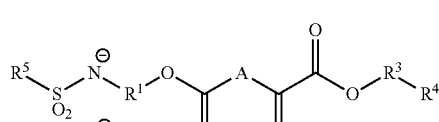
(1-1-6)

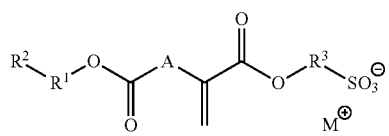
(1-1-7)

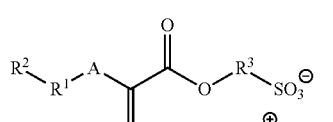
(1-1-8)

-continued

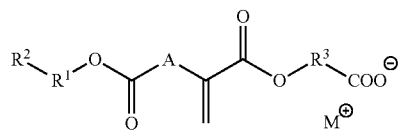
(1-1-9)

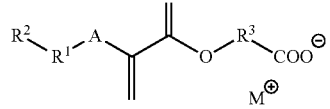
(1-1-10)

[Chemical Formula 15]

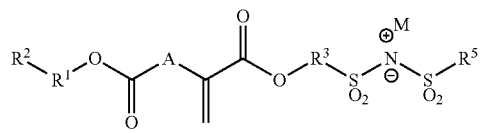
(1-1-11)

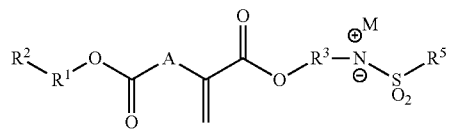
(1-1-12)

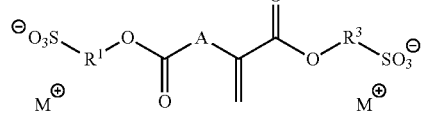
(1-1-13)

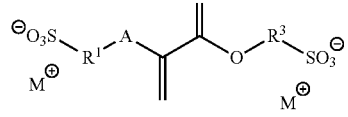
(1-1-14)

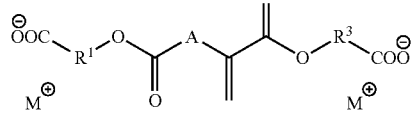
(1-1-15)

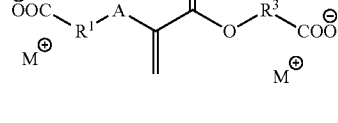
(1-1-16)

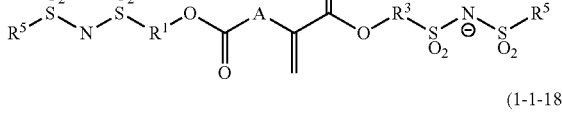
(1-1-17)

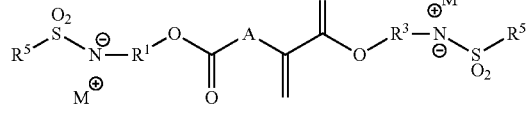
(1-1-18)

Specific examples of compounds represented by the above general formulas (1-1-1) to (1-1-18) are shown below. In the formulas shown below, $M^+$ is the same as defined above.

[Chemical Formula 16]
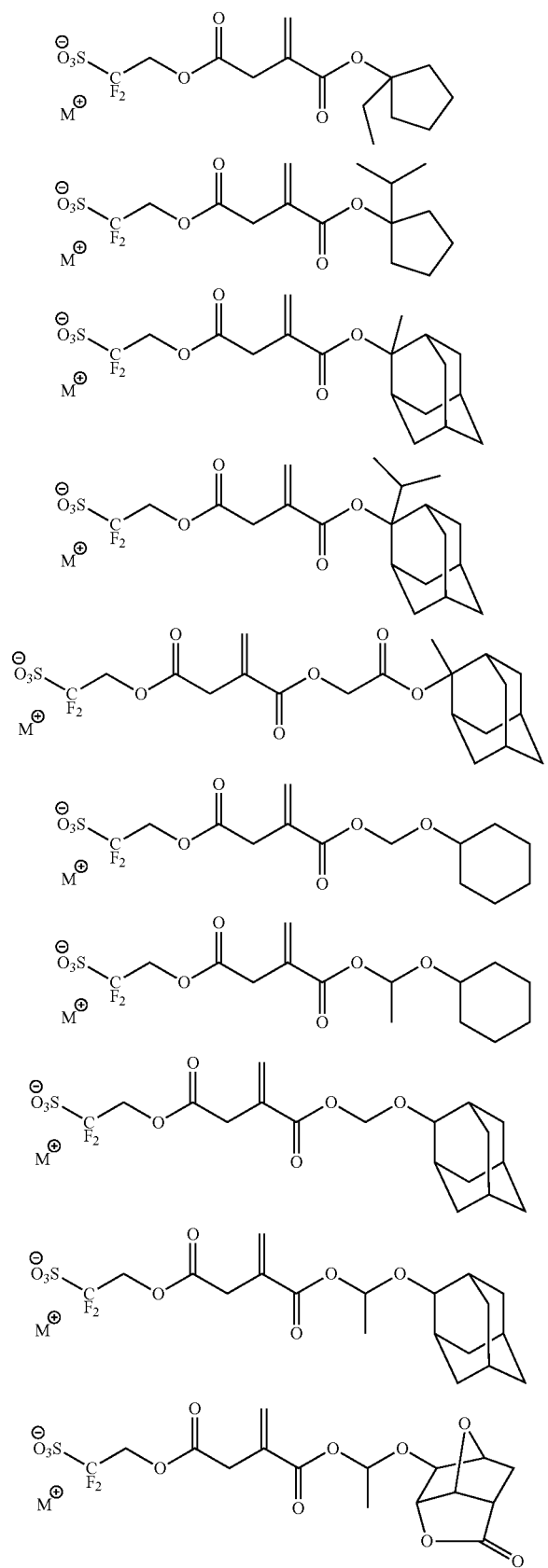
[Chemical Formula 17]
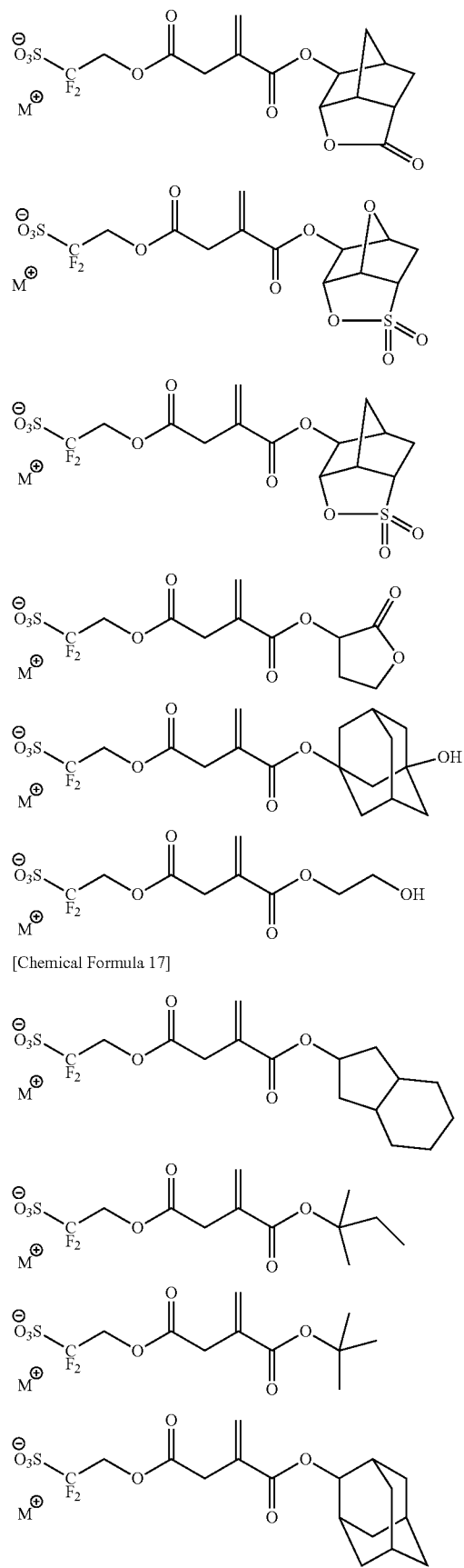

-continued
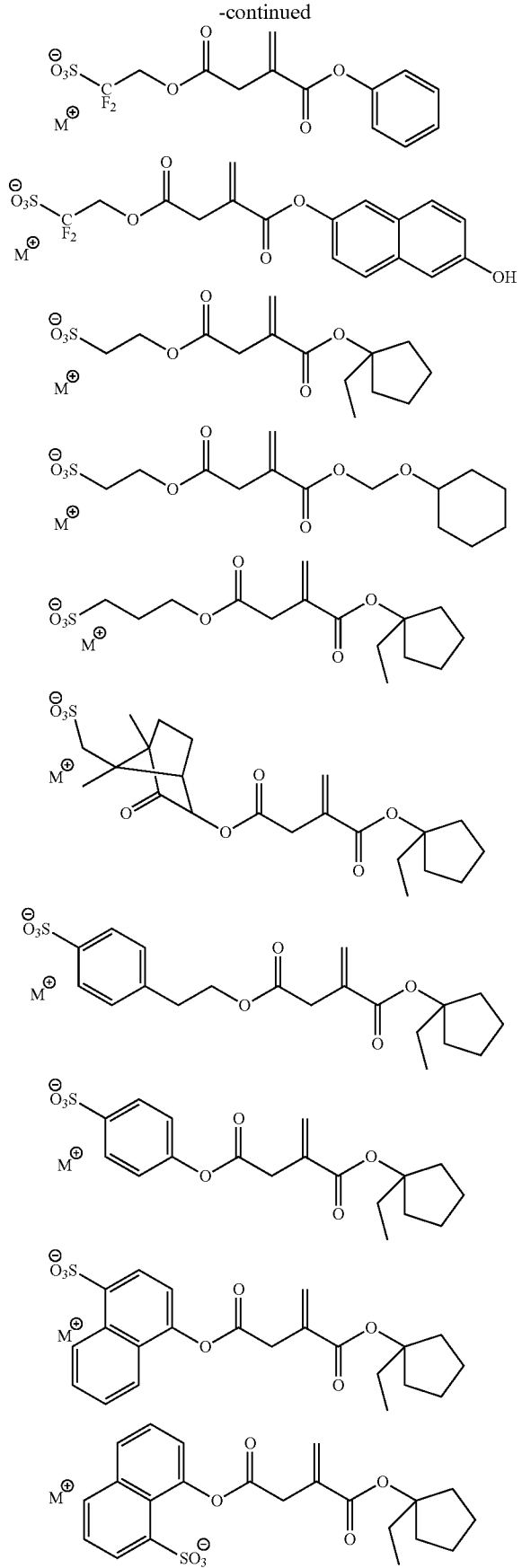
[Chemical Formula 18]
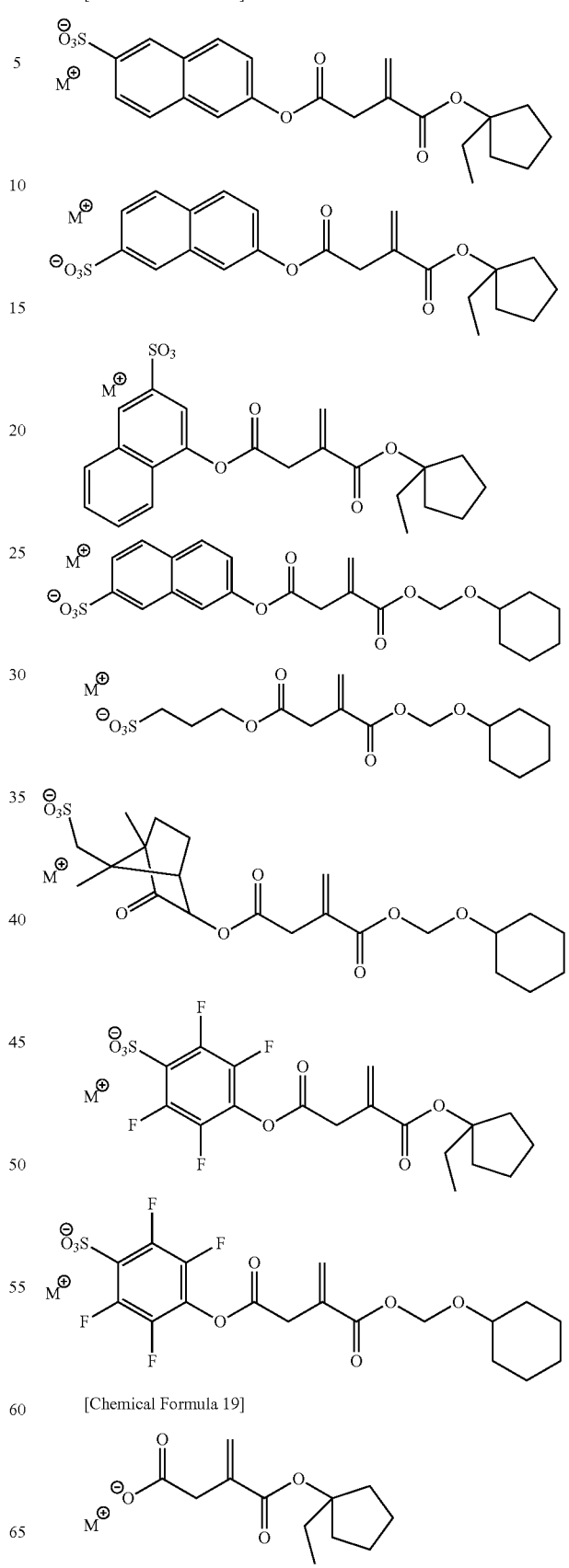
[Chemical Formula 19]

31
-continued

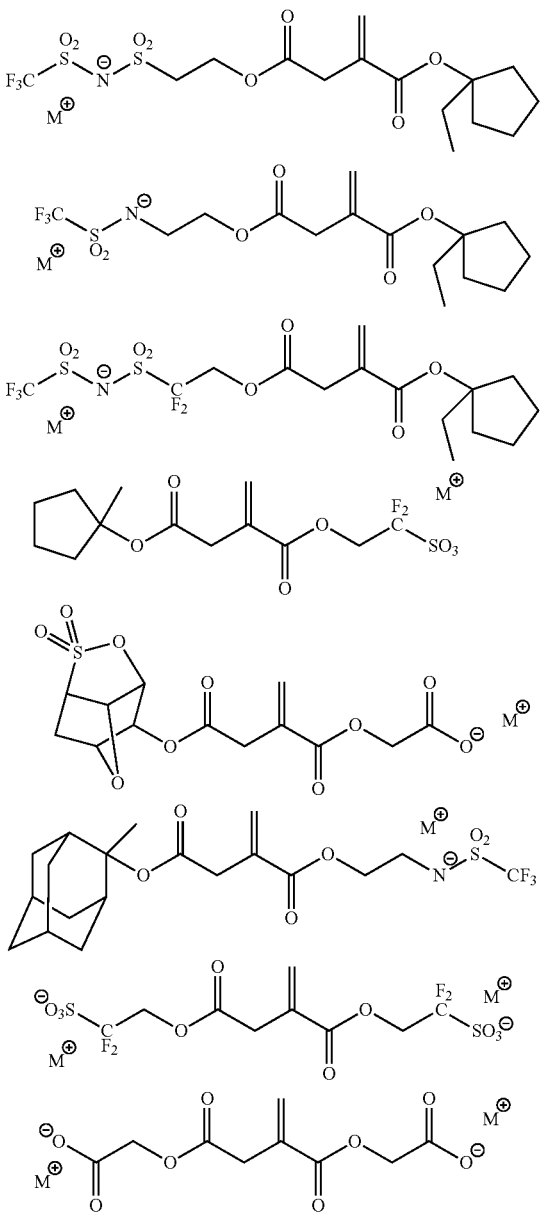

[Chemical Formula 20]

32

(Production Method of Compound (1-1))

The production method of the compound (1-1) of the present invention is not particularly limited. For example, when producing a compound (1-11) in which $R^2$ is a group represented by the aforementioned general formula (1-an1) and n0 is 1, a compound (i-1) represented by general formula (i-1) shown below can be reacted with a compound (i-2) represented by general formula (i-2) shown below to obtain a compound (i-3) represented by general formula (i-3) shown below, and following hydrolysis of the compound (i-3) to obtain a compound (i-4) represented by general formula (i-4) shown below, the compound (i-4) can be reacted with a compound (i-5), thereby producing a compound (1-11) represented by general formula (1-11).

[Chemical Formula 21]

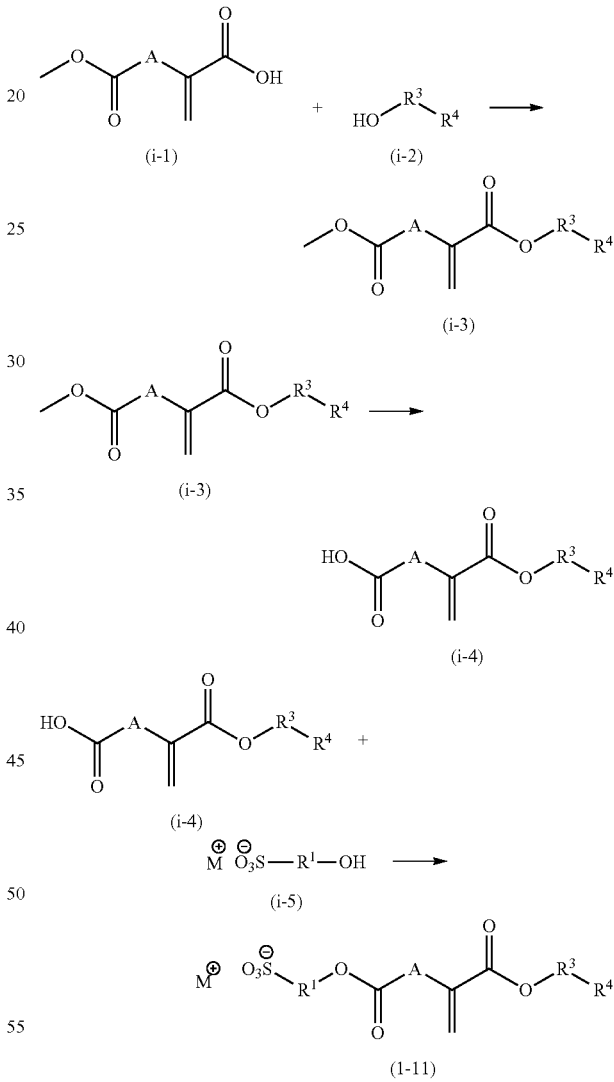

In the formulas, $R^1$, $R^3$, $R^4$, A and $M^+$ are the same as defined above.

Firstly, the compound (i-1) is reacted with the compound (i-2), to thereby obtain the compound (i-3).

In formula (i-1), A is the same as defined above. In formula (i-2), $R^3$ and $R^4$ are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate halogenating agent, a condensing agent or an acid catalyst, followed by washing and recovering the reaction mixture.

The halogenating agent, condensation agent or acid catalyst used in the above reaction is not particularly limited, and examples thereof include thionyl chloride and carbodiimide ($R^d$—N=C=N—$R^d$, wherein $R^d$ represents an alkyl group). The amount thereof is preferably about 0.05 to about 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include dichloromethane and the like. The amount of the organic solvent is preferably 0.5 to 100 parts by weight, more preferably 0.5 to 20 parts by weight, per 1 part by weight of the amount of the compound (i-1). As the solvent, one type of solvent may be used alone, or two or more types of solvents may be used in combination.

In general, the amount of the compound (i-2) used in the above reaction is preferably about 0.5 to about 5 moles per 1 mole of the compound (i-1), and more preferably about 0.8 to about 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the ester bond of the obtained compound (i-3) is hydrolyzed, thereby obtaining the compound (i-4).

The method for hydrolyzing the ester bond of the compound (i-3) to obtain the compound (i-4) is not particularly limited, but can be performed, for example, by reacting the compound (i-3) in an organic solvent in the presence of an appropriate base or an appropriate acid, followed by washing and recovering the reaction product.

The base or acid used in the above reaction is not particularly limited, and examples of the base include sodium hydroxide, and examples of the acid include hydrochloric acid. The amount thereof is preferably about 0.3 to 3 moles, per 1 mole of the compound (i-3).

Examples of the organic solvent used in the above reaction include dichloromethane, methanol, tetrahydrofuran and the like. The amount of the organic solvent is preferably 0.5 to 100 parts by weight, and more preferably 0.5 to 20 parts by weight, per 1 part by weight of the weight of the compound (i-3). As the solvent, one type of solvent may be used alone, or two or more types of solvents may be used in combination.

The reaction time in the above reaction depends on the type of the compound (i-3) or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-4) is reacted with the compound (i-5), thereby obtaining the compound (1-11).

In formula (i-5), $R^1$ and $M^+$ are the same as defined above.

As the compound (i-5), commercially available compounds may be used, or the compounds may be synthesized.

The method for reacting the compound (i-4) with the compound (i-5) to obtain the compound (1-11) is not particularly limited, but can be performed, for example, by reacting the compound (i-4) with the compound (i-5) in an organic solvent in the presence of an appropriate base, followed by washing and recovering the reaction mixture.

The base used in the above reaction is not particularly limited, and examples thereof include N,N-dimethylaminopyridine. The amount thereof is preferably about 0.05 to 5 moles, per 1 mole of the compound (i-4).

As the organic solvent used in the above reaction, any organic solvent which is capable of dissolving the raw materials, i.e., the compound (i-4) and the compound (i-5) can be used, and specific examples thereof include dichloromethane and the like. The amount of the organic solvent is preferably 0.5 to 100 parts by weight, more preferably 0.5 to 20 parts by weight, per 1 part by weight of the amount of the compound (i-4). As the solvent, one type of solvent may be used alone, or two or more types of solvents may be used in combination.

In general, the amount of the compound (i-5) used in the above reaction is preferably about 0.5 to about 5 moles per 1 mole of the compound (i-4), and more preferably about 0.8 to about 4 moles per 1 mole of the compound (i-4).

The reaction time depends on the reactivity of the compounds (i-4) and (i-5), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (1-11) contained in the reaction liquid may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (1-11) obtained in the manner described above can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

Because the compound according to the first aspect of the present invention described above has a group represented by the aforementioned formula (1-an1) to (1-an3) within at least one of $R^2$ and $R^4$, it exhibits an acid generating ability when the aforementioned $M^+$ is an organic cation. Further, in the case where the aforementioned $M^+$ is a metal cation, a compound exhibiting an acid generating ability can be easily obtained by salt exchange with an onium salt having a desired organic cation.

Therefore, the compound according to the first aspect in which the aforementioned $M^+$ represents an organic cation can be used as the acid generator according to the fourth aspect which will be described later, and this acid generator can be suitably used for the resist composition according to the fifth aspect which will be described later.

Further, because the compound according to the first aspect has a polymerizable group within the structure thereof, it is possible to form the polymeric compound according to the second aspect which will be described later by cleaving the polymerizable group to convert the compound into a structural unit, followed by polymerization of the structural unit or copolymerization of the structural unit with other structural units. The polymeric compound can be suitably used as a base resin of the resist composition according to the third aspect which will be described later. The polymeric compound and the base resin exhibit acid generating ability when the aforementioned $M^+$ is an organic cation.

<<Polymeric Compound>>

The polymeric compound according to the second aspect of the present invention is a polymeric compound having a structural unit derived from the abovementioned compound according to the first aspect in which the aforementioned M⁺ represents an organic cation. The structural unit derived from the abovementioned compound according to the first aspect in which the aforementioned M⁺ represents an organic cation is represented by formula (a0) shown below.

[Chemical Formula 22]

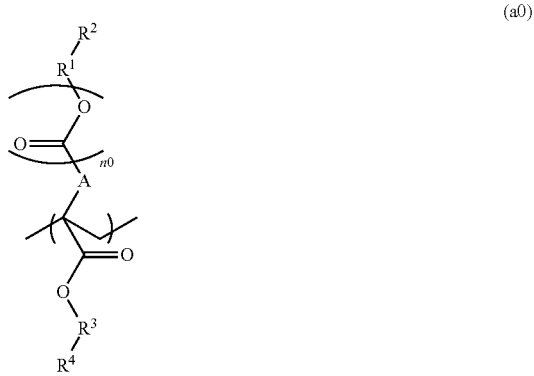

(a0)

In the formula, each of $R^1$ and $R^3$ independently represents a single bond or a divalent linking group; A represents a divalent linking group; each of $R^2$ and $R^4$ independently represents a hydroxyl group, an aliphatic cyclic group which may have a substituent, or a group represented by general formula (1-an1), (1-an2) or (1-an3) shown below, provided that at least one of $R^2$ and $R^4$ represents a group represented by general formula (1-an1), (1-an2) or (1-an3) shown below. n0 represents 0 or 1.

[Chemical Formula 23]

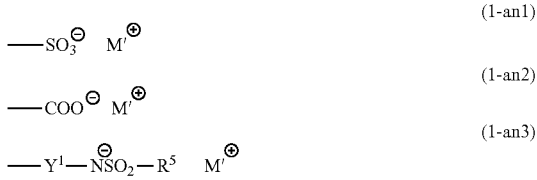

In the formulas, $Y^1$ represents a single bond or —SO₂—; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M'^+$ represents an organic cation.

In formula (a0), $R^1$ to $R^4$, A and n0 are the same as defined above, respectively.

In formulas (1-an1), (1-an2) and (1-an3), $R^5$ and $Y^1$ are the same as defined above, respectively. $M'^+$ represents an organic cation, and examples thereof include the same organic cations as those described above for M⁺.

Details regarding the polymeric compound according to the second aspect of the present invention are the same as the description for the component (A1') of the resist composition according to the third aspect which will be described later.

The polymeric compound according to the second aspect of the present invention can be suitably used as a base resin of a resist composition because it has an ability of generating acid.

<<Resist Composition 1>>

The resist composition according to the third aspect of the present invention (hereafter, sometimes referred to as "resist composition 1") contains a base component (A') that generates acid upon exposure and exhibits changed solubility in a developing solution under the action of acid (hereafter, referred to as "component (A')"), wherein the base component (A') contains a polymeric compound (A1') according to the aforementioned second aspect, i.e., a polymeric compound (A1') having a structural unit (a0) represented by formula (a0) which is derived from the compound according to the aforementioned first aspect in which M⁺ represents an organic cation.

<Component (A')>

[Polymeric Compound (A1')]

The component (A') in the resist composition 1 of the present invention is a base component which generates acid upon exposure and exhibits changed solubility in a developing solution under the action of acid.

In the present invention, the term "base component" refers to an organic compound capable of forming a film, and preferably refers to an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a "low molecular weight compound".

As a polymer, any of those which have a molecular weight of 1,000 or more is generally used. Hereafter, a polymer having a molecular weight of 1,000 or more is referred to as a "polymeric compound". With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

In the present invention, the component (A') in the resist composition 1 contains a polymeric compound (A1') (hereafter, referred to as "component (A1')") including a structural unit (a0) represented by the aforementioned general formula (a0).

The resist composition 1 of the present invention is preferably a resist composition which forms a positive pattern in an alkali developing process and a negative pattern in a solvent developing process. By using the resist composition as well as the component (A1') that satisfy these requirements, since the polarity of the base component changes prior to and after exposure, an excellent development contrast can be obtained not only in an alkali developing process, but also in a solvent developing process.

More specifically, when an alkali developing process is used, the component (A1') is substantially insoluble in an alkali developing solution prior to exposure, but when acid is generated from the component (A') upon exposure, the action of this acid causes an increase in the polarity, thereby increasing the solubility in an alkali developing solution. Therefore, in the formation of a resist pattern, by conducting selective exposure of a resist film formed by applying the resist composition onto a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, when a solvent developing process is used, the component (A1') exhibits high solubility in an organic developing solution prior to exposure, and when acid is generated from the component (A1') upon exposure, the action of the acid causes an increase in the polarity, thereby decreasing the solubility in an organic developing solution. Therefore, in the formation of a resist pattern, by conducting selective exposure of a resist film formed by applying the resist composition onto a substrate, the exposed portions changes from a soluble state to an insoluble state in an organic developing solution, whereas the unexposed portions remain soluble in an organic developing solution. As a result, by conducting development using an organic developing solution, a contrast can be made between the exposed portions and the unexposed portions, thereby enabling the formation of a negative resist pattern.

In the resist composition 1 of the present invention, as described above, the component (A1') has the structural unit (a0) represented by the aforementioned general formula (a0).

In the resist composition 1 of the present invention, it is preferable that the component (A1') also has a structural unit (a1) derived from an acrylate ester which may have the hydrogen atom bonded to the carbon atom on the α-position substituted with a substituent and contains an acid decomposable group which exhibits increased polarity by the action of acid.

In the resist composition 1 of the present invention, the component (A1') preferably also includes at least one structural unit (a2) selected from the group consisting of structural units derived from an acrylate ester in which the hydrogen atom bonded to the carbon atom on the α-position may be substituted with a substituent and containing an —SO$_2$— containing cyclic group, and structural units derived from an acrylate ester in which the hydrogen atom bonded to the carbon atom on the α-position may be substituted with a substituent and containing a lactone-containing cyclic group.

Further, in the resist composition 1 of the present invention, it is preferable that the component (A1') also has a structural unit (a3) derived from an acrylate ester which may have the hydrogen atom bonded to the carbon atom on the α-position substituted with a substituent and contains a polar group-containing aliphatic hydrocarbon group.

(Structural Unit (a0))

The structural unit (a0) is a structural unit represented by general formula (a0) shown below.

The structural unit (a0) generates acid upon exposure because it has a group represented by the aforementioned formula (1-an1) to (1-an3) within at least one of $R^2$ and $R^4$.

[Chemical Formula 24]

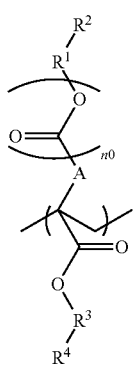

(a0)

In the formula, each of $R^1$ and $R^3$ independently represents a single bond or a divalent linking group; A represents a divalent linking group; each of $R^2$ and $R^4$ independently represents a hydroxyl group, a hydrocarbon group which may have a substituent, or a group represented by general formula (1-an1), (1-an2) or (1-an3) shown below, provided that at least one of $R^2$ and $R^4$ represents a group represented by general formula (1-an1), (1-an2) or (1-an3) shown below; and n0 represents 0 or 1.

[Chemical Formula 25]

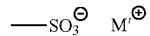 (1-an1)

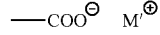 (1-an2)

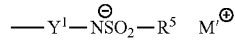 (1-an3)

In the formulas, $Y^1$ represents a single bond or —SO$_2$—; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M'^+$ represents an organic cation.

In formula (a0), $R^1$ to $R^4$, A and n0 are the same as defined above, respectively.

In formulas (1-an1), (1-an2) and (1-an3), $R^5$, $Y^1$ and $M'^+$ are the same as defined above, respectively.

Specific examples of the structural unit (a0) include the structural units obtained by cleavage of a polymerizable group listed above within the description for the specific examples of the compound according to the first aspect.

Of the various possibilities, it is particularly desirable that $R^2$ and $R^4$ in the structural unit (a0) have an aliphatic cyclic group, and that the aliphatic cyclic group is an acid dissociable group. Because the structural unit (a0) is a structural unit having an acid generating ability, when the structural unit (a0) also has an acid dissociable group therein, various lithography properties such as resolution and roughness as well as the pattern shape can be improved, compared to those cases where different structural units are each provided with an acid generating ability and an acid dissociable group.

In the component (A1'), as the structural unit (a0), one type of structural unit may be used alone, or two or more types of structural units may be used in combination.

In the component (A1'), the amount of the structural unit (a0) based on the combined total of all structural units constituting the component (A1') is preferably 0.1 to 80 mol %, more preferably 0.5 to 60 mol %, still more preferably 1 to 50 mol %, and most preferably 1.5 to 40 mol %. When the amount of the structural unit (a0) is at least as large as the lower limit of the above-mentioned range, various lithography properties (such as LWR and resolution) and resist pattern shape can be improved. On the other hand, when the amount of the structural unit (a0) is no more than the upper limit of the above-mentioned range, a good balance can be achieved with the other structural units.

(Structural Unit (a1))

The structural unit (a1) is a structural unit derived from an acrylate ester which may have the hydrogen atom bonded to the carbon atom on the α-position substituted with a substituent and contains an acid decomposable group which exhibits increased polarity by the action of acid.

The term "acid decomposable group" refers to a group exhibiting acid decomposability in which at least a part of the bond within the structure of this acid decomposable group may be cleaved by the action of acid generated from the component (A') upon exposure.

Examples of the acid decomposable group that exhibits increased polarity by the action of acid include groups which are decomposed by the action of acid to form a polar group.

Examples of the polar group include a carboxyl group, a hydroxyl group, an amino group and a sulfo group (—SO$_3$H). Among these, a polar group containing —OH in the structure thereof (hereafter, sometimes referred to as "OH-containing polar group") is preferable, and a carboxyl group or a hydroxyl group is more preferable.

More specific examples of acid decomposable groups include groups in which the aforementioned polar group is protected with an acid dissociable group (such as groups in which the hydrogen atom of an OH-containing polar group is protected with an acid dissociable group).

An "acid dissociable group" is a group exhibiting acid dissociability in which at least the bond between the acid dissociable group and the atom adjacent to this acid dissociable group may be cleaved by the action of acid generated from the component (A') upon exposure. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire component (A1') is increased. By the increase in the polarity, in the case of applying an alkali developing process, the solubility in an alkali developing solution is relatively increased.

On the other hand, in the case of applying a solvent developing process, the solubility in an organic developing solution containing an organic solvent decreases.

As the acid dissociable group for the structural unit (a1), any of those which have been proposed as acid dissociable groups for a base resin of a chemically amplified resist may be used. Generally, groups that form either a cyclic or chain-like tertiary alkyl ester with the carboxyl group of the (meth) acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom, thereby forming a carboxyl group. As a result, the polarity of the component (A1') is increased.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid-dissociable groups include aliphatic branched acid-dissociable groups and acid dissociable groups containing an aliphatic cyclic group.

In the present description and claims, the term "aliphatic branched" refers to a branched structure having no aromaticity.

The structure of the "aliphatic branched acid dissociable group" is not limited to groups constituted of only carbon atoms and hydrogen atoms (not limited to hydrocarbon groups), but is preferably a hydrocarbon group.

Further, the "hydrocarbon group" may be either saturated or unsaturated, but in most cases, is preferably saturated.

Examples of aliphatic branched, acid dissociable groups include tertiary alkyl groups of 4 to 8 carbon atoms, and specific examples include a tert-butyl group, a tert-pentyl group and a tert-heptyl group.

The term "aliphatic cyclic group" refers to a monocyclic group or polycyclic group that has no aromaticity.

The "aliphatic cyclic group" within the structural unit (a1) may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but in most cases, is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable group, for example, a group which has a tertiary carbon atom on the ring structure of the cyclic alkyl group can be used. Specific examples include groups represented by any one of general formulas (1-1) to (1-9) shown below, such as a 2-methyl-2-adamantyl group and a 2-ethyl-2-adamantyl group.

Further, as examples of aliphatic branched acid dissociable group, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as those represented by general formulas (2-1) to (2-6) shown below, can be given.

[Chemical Formula 26]

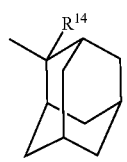

(1-1)

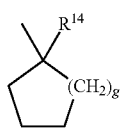 (1-2)

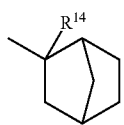 (1-3)

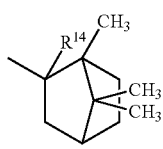 (1-4)

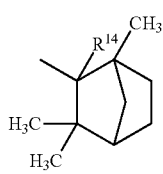 (1-5)

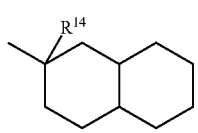 (1-6)

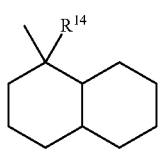 (1-7)

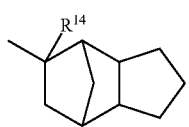 (1-8)

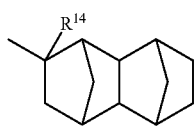 (1-9)

In the formulas above, $R^{14}$ represents an alkyl group; and g represents an integer of 0 to 8.

[Chemical Formula 27]

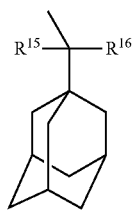 (2-1)

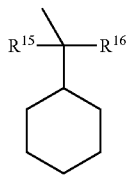 (2-2)

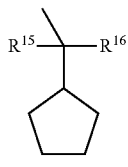 (2-3)

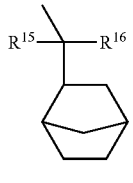 (2-4)

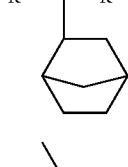 (2-5)

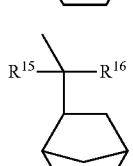 (2-6)

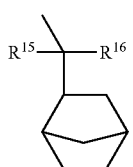

In the formulas, each of $R^{15}$ and $R^{16}$ independently represents an alkyl group (which may be linear or branched, and preferably has 1 to 5 carbon atoms).

As the alkyl group for $R^{14}$, a linear or branched alkyl group is preferable.

The linear alkyl group preferably has 1 to 5 carbon atoms, more preferably 1 to 4 carbon atoms, and still more preferably 1 or 2 carbon atoms. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5 carbon atoms. Specific examples of such branched alkyl groups include an isopropyl group, an isobutyl group, a tert-butyl group, an isopentyl group and a neopentyl group, and an isopropyl group or a tert-butyl group is particularly desirable.

g is preferably an integer of 0 to 3, more preferably an integer of 1 to 3, and still more preferably 1 or 2.

As the alkyl group for $R^{15}$ and $R^{16}$, the same alkyl groups as those for $R^{14}$ can be used.

In formulas (1-1) to (1-9) and formulas (2-1) to (2-6), a portion of the carbon atoms that constitute the ring(s) may be replaced with an ethereal oxygen atom (—O—).

Further, in formulas (1-1) to (1-9) and formulas (2-1) to (2-6), one or more of the hydrogen atoms bonded to the carbon atoms that constitute the ring(s) may be substituted with a substituent. Examples of the substituent include an alkyl group of 1 to 5 carbon atoms, a fluorine atom and a fluorinated alkyl group.

An "acetal-type acid-dissociable group" generally substitutes a hydrogen atom at the terminal of an OH-containing polar group such as a carboxyl group or hydroxyl group, so as to be bonded with an oxygen atom. When acid is generated upon exposure, the generated acid acts to break the bond between the acetal-type acid dissociable group and the oxygen atom to which the acetal-type, acid dissociable group is bonded, thereby forming an OH-containing polar group such as a carboxyl group or a hydroxyl group. As a result, the polarity of the component (A1') is increased.

Examples of acetal-type acid-dissociable groups include groups represented by general formula (p1) shown below.

[Chemical Formula 28]

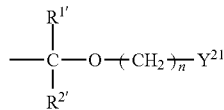

(p1)

In the formula, each of $R^{1'}$ and $R^{2'}$ independently represents a hydrogen atom or an alkyl group of 1 to 5 carbon atoms; n represents an integer of 0 to 3; and $Y^{21}$ represents an alkyl group of 1 to 5 carbon atoms or an aliphatic cyclic group.

In general formula (p1) above, n is preferably an integer of 0 to 2, more preferably 0 or 1, and most preferably 0.

As the alkyl group of 1 to 5 carbon atoms for $R^{1'}$ and $R^{2'}$, the same alkyl groups of 1 to 5 carbon atoms as those described above for R can be used, and a methyl group or an ethyl group is preferable, and a methyl group is most preferable.

In the present invention, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 29]

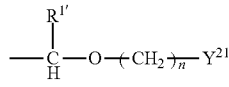

(p1-1)

In the formula, $R^{1'}$, n and $Y^{21}$ are the same as defined above.

As the alkyl group of 1 to 5 carbon atoms for $Y^{21}$, the same alkyl groups of 1 to 5 carbon atoms as those described above for R can be used.

As the aliphatic cyclic group for $Y^{21}$, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable group, groups represented by general formula (p2) shown below can also be used.

[Chemical Formula 30]

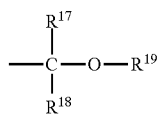

(p2)

In the formula, $R^{17}$ and $R^{18}$ each independently represents a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a1), it is preferable to use at least one member selected from the group consisting of structural units represented by general formula (a1-0-1) shown below and structural units represented by general formula (a1-0-2) shown below.

[Chemical Formula 31]

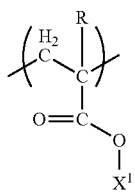

(a1-0-1)

In the formula, R represents a hydrogen atom, an alkyl group of 1 to 5 carbon atoms or a halogenated alkyl group of 1 to 5 carbon atoms; and $X^1$ represents an acid dissociable group.

[Chemical Formula 32]

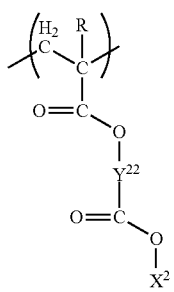

(a1-0-2)

In the formula, R represents a hydrogen atom, an alkyl group of 1 to 5 carbon atoms or a halogenated alkyl group of 1 to 5 carbon atoms; $X^2$ represents an acid dissociable group; and $Y^{22}$ represents a divalent linking group.

In general formula (a1-0-1), the alkyl group of 1 to 5 carbon atoms or halogenated alkyl group of 1 to 5 carbon atoms for R is the same as defined above.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a1-0-2), as the alkyl group of 1 to 5 carbon atoms or halogenated alkyl group of 1 to 5 carbon atoms for R, the same alkyl groups of 1 to 5 carbon atoms or halogenated alkyl groups of 1 to 5 carbon atoms as those defined above for the substituent which may be bonded to the carbon atom on the α-position can be used. $X^2$ is the same as defined for $X^1$ in general formula (a1-0-1).

As preferable examples of the divalent linking group for $Y^{22}$, a divalent hydrocarbon group which may have a substituent, and a divalent linking group containing a hetero atom can be given.

The description that the hydrocarbon group "may have a substituent" means that some or all of the hydrogen atoms within the hydrocarbon group may be substituted with an atom other than a hydrogen atom or with a group.

The hydrocarbon group may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As specific examples of the aliphatic hydrocarbon group for the hydrocarbon group as $Y^{22}$, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8 carbon atoms, still more preferably 1 to 5 carbon atoms, and most preferably 1 or 2 carbon atoms.

As the linear aliphatic hydrocarbon group, a linear alkylene group is preferable, and specific examples include a methylene group [—$CH_2$—], an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —$CH(CH_3)$—, —$CH(CH_2CH_3)$—, —$C(CH_3)_2$—, —$C(CH_3)(CH_2CH_3)$—, —$C(CH_3)(CH_2CH_2CH_3)$—, and —$C(CH_2CH_3)_2$—; alkylethylene groups such as —$CH(CH_3)CH_2$—, —$CH(CH_3)CH(CH_3)$—, —$C(CH_3)_2CH_2$—, —$CH(CH_2CH_3)CH_2$—, and —$C(CH_2CH_3)_2$—$CH_2$—; alkyltrimethylene groups such as —$CH(CH_3)CH_2CH_2$—, and —$CH_2CH(CH_3)CH_2$—; and alkyltetramethylene groups such as —$CH(CH_3)CH_2CH_2CH_2$—, and —$CH_2CH(CH_3)CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (═O).

As examples of the hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (═O).

Examples of the aforementioned aromatic hydrocarbon group for $Y^{22}$ include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

When $Y^{22}$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, "-$A^R$-O—$B^R$—" (wherein 0 is an oxygen atom, and each of $A^R$ and $B^R$ independently represents a divalent hydrocarbon group which may have a substituent)" and a combination of a divalent hydrocarbon group which may have a substituent with a divalent linking group containing a hetero atom. As examples of the divalent hydrocarbon group which may have a substituent, the same groups as those described above for the hydrocarbon group which may have a substituent can be given, and a linear or branched aliphatic hydrocarbon group or an aliphatic hydrocarbon group containing a ring in the structure thereof is preferable.

When $Y^{22}$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^{22}$ is "-$A^R$-O—$B^R$-", each of $A^R$ and $B^R$ independently represents a divalent hydrocarbon group which may have a substituent.

The hydrocarbon group for $A^R$ may be either an aliphatic hydrocarbon group, or an aromatic hydrocarbon group. An "aliphatic hydrocarbon group" refers to a hydrocarbon group that has no aromaticity.

The aliphatic hydrocarbon group for $A^R$ may be either saturated or unsaturated. In general, the aliphatic hydrocarbon group is preferably saturated.

As specific examples of the aliphatic hydrocarbon group for $A^R$, a linear or branched aliphatic hydrocarbon group, and an aliphatic hydrocarbon group having a ring in the structure thereof can be given. These are the same as defined above.

Among these, $A^R$ is preferably a linear aliphatic hydrocarbon group, more preferably a linear alkylene group, still more preferably a linear alkylene group of 2 to 5 carbon atoms, and most preferably an ethylene group.

As the hydrocarbon group for $B^R$, the same divalent hydrocarbon groups as those described above for $A^R$ can be used.

As $B^R$, a linear or branched aliphatic hydrocarbon group is preferable, and a methylene group or an alkylmethylene group is particularly desirable.

The alkyl group within the alkylmethylene group is preferably a linear alkyl group of 1 to 5 carbon atoms, more preferably a linear alkyl group of 1 to 3 carbon atoms, and most preferably a methyl group.

Specific examples of the structural unit (a1) include structural units represented by general formulas (a1-1) to (a1-4) shown below.

[Chemical Formula 33]

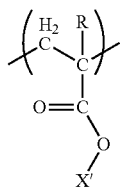

(a1-1)

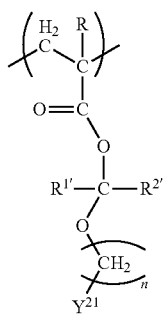

(a1-2)

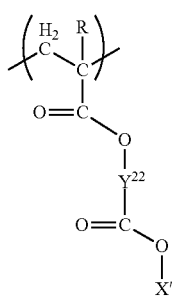

(a1-3)

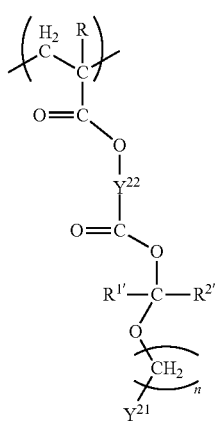

(a1-4)

In the formulas, X' represents a tertiary alkyl ester-type acid dissociable group; $Y^{21}$ represents an alkyl group of 1 to 5 carbon atoms or an aliphatic cyclic group; n represents an integer of 0 to 3; $Y^{22}$ represents a divalent linking group; R is the same as defined above; and each of $R^{1'}$ and $R^{2'}$ independently represents a hydrogen atom or an alkyl group of 1 to 5 carbon atoms.

In the above formulas, examples of the tertiary alkyl ester-type acid dissociable group for X' include the same tertiary alkyl ester-type acid dissociable groups as those described above for $X^1$.

$R^{1'}$, $R^{2'}$, n and $Y^{21}$ are respectively the same as defined for $R^{1'}$, $R^{2'}$, n and $Y^{21}$ in general formula (p1) described above in connection with the "acetal-type acid dissociable group".

As examples of $Y^{22}$, the same groups as those described above for $Y^{22}$ in general formula (a1-0-2) can be given.
Specific examples of the structural units represented by general formulas (a1-1) to (a1-4) are shown below.
In the formulas shown below, $R^\alpha$ represents a hydrogen atom, a methyl group or a trifluoromethyl group.
[Chemical Formula 34]
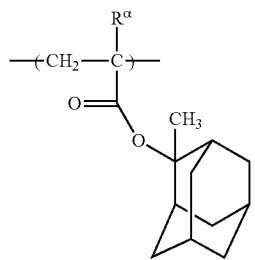
(a1-1-1)
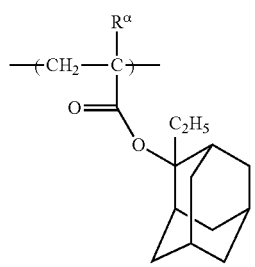
(a1-1-2)
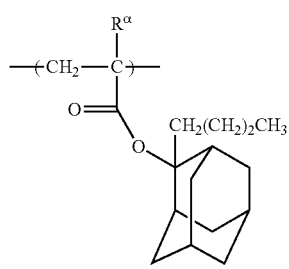
(a1-1-3)
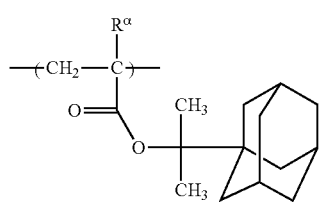
(a1-1-4)
(a1-1-5)
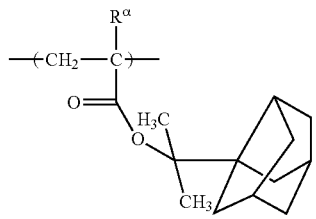
(a1-1-6)
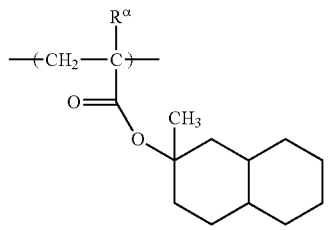
(a1-1-7)
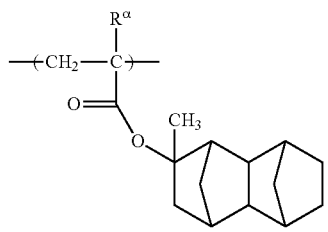
(a1-1-8)
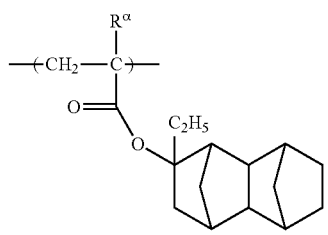
(a1-1-9)
[Chemical Formula 35]
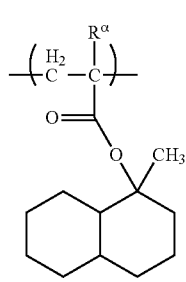
(a1-1-10)
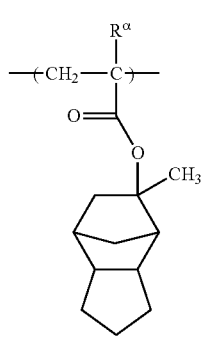
(a1-1-11)

(a1-1-12) 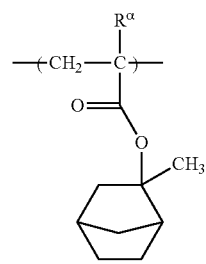
(a1-1-13) 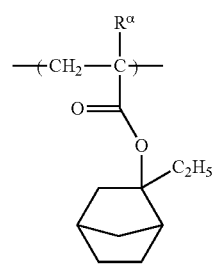
(a1-1-14) 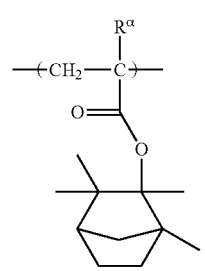
(a1-1-15) 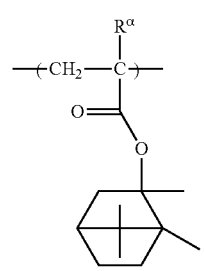
(a1-1-16) 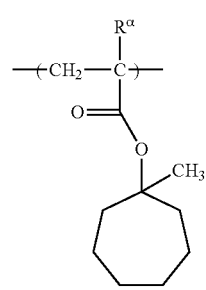
(a1-1-17) 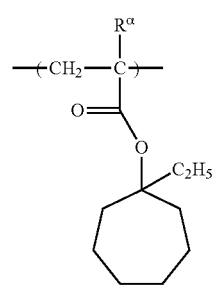
(a1-1-18) 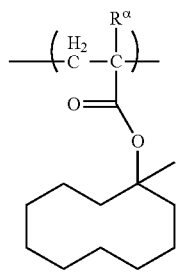
(a1-1-19) 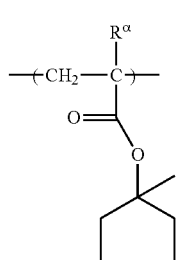
(a1-1-20) 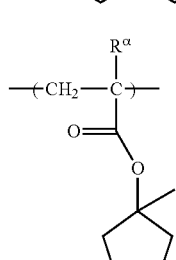
(a1-1-21) 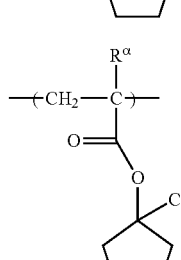
[Chemical Formula 36]
(a1-1-22) 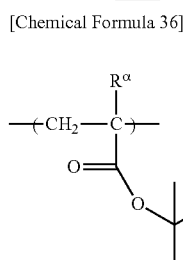
(a1-1-23) 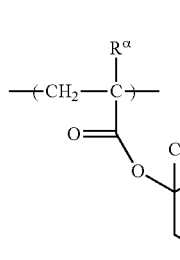

(a1-1-24) 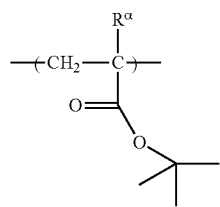
(a1-1-25) 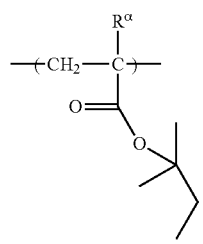
(a1-1-26) 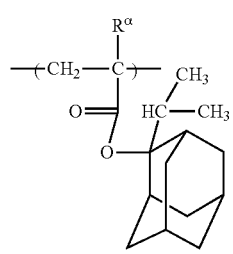
(a1-1-27) 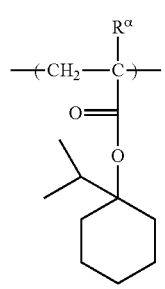
(a1-1-28) 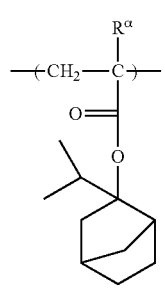
(a1-1-29) 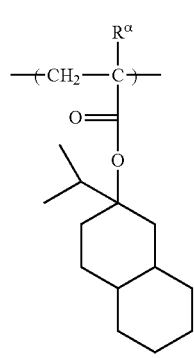
(a1-1-30) 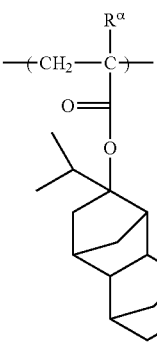
(a1-1-31) 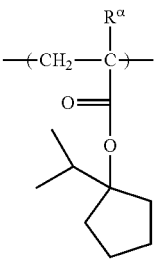
(a1-1-32) 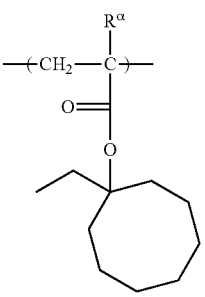
[Chemical Formula 37]
(a1-2-1) 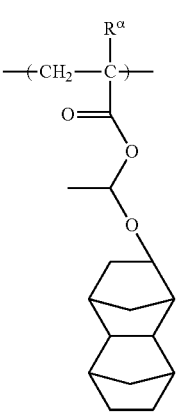

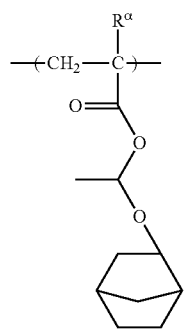 (a1-2-2)
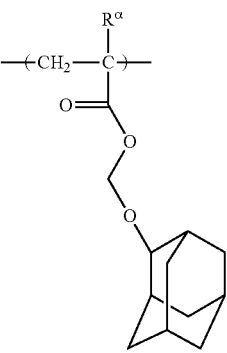 (a1-2-6)
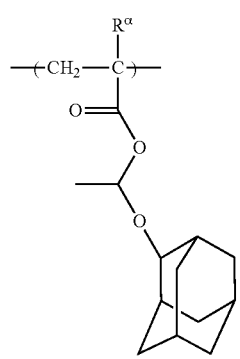 (a1-2-3)
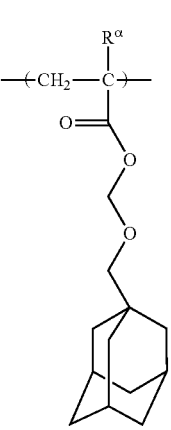 (a1-2-7)
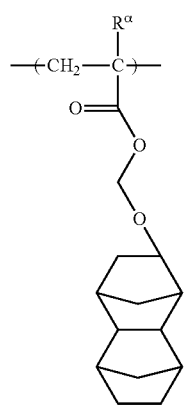 (a1-2-4)
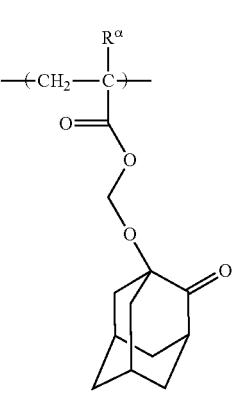 (a1-2-8)
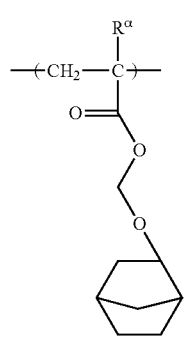 (a1-2-5)
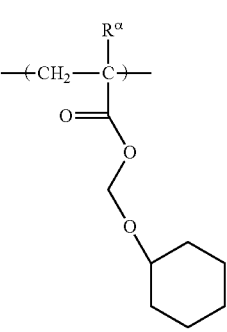 (a1-2-9)

(a1-2-10) 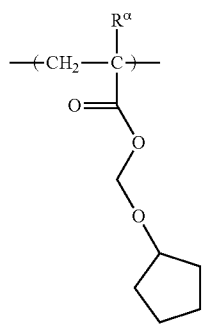
(a1-2-14) 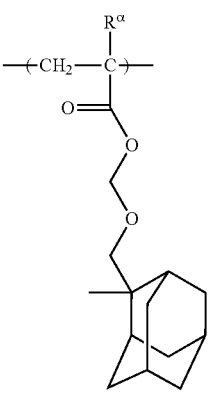
(a1-2-11) 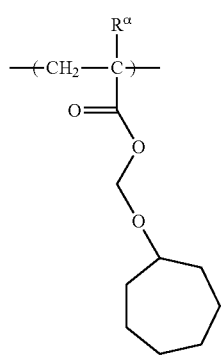
(a1-2-15) 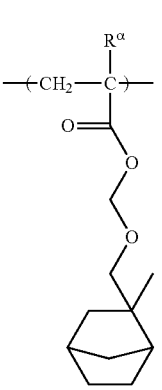
(a1-2-12) 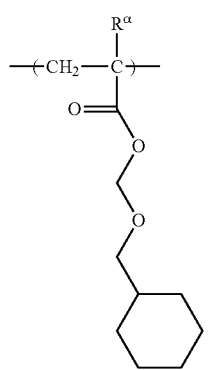
(a1-2-16) 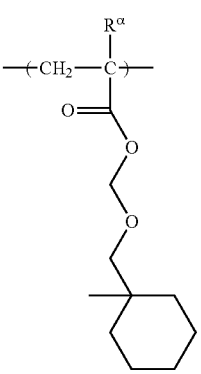
(a1-2-13) 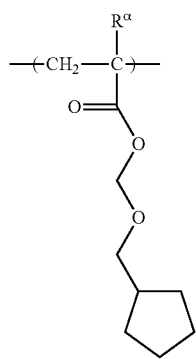
(a1-2-17) 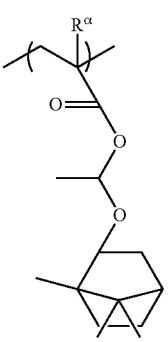

(a1-2-18)
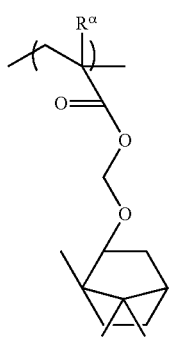
(a1-2-19)
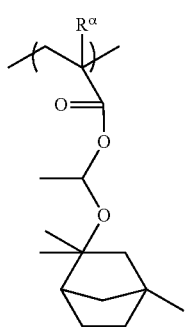
(a1-2-20)
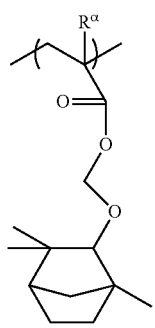
(a1-2-21)
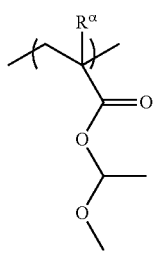
(a1-2-22)
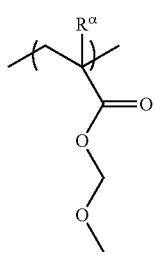
(a1-2-23)
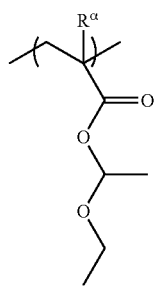
(a1-2-24)
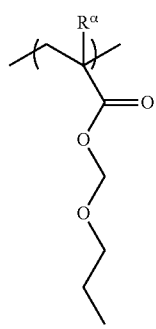
[Chemical Formula 38]
(a1-3-1)
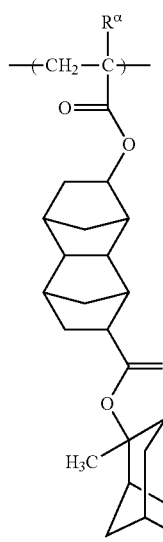

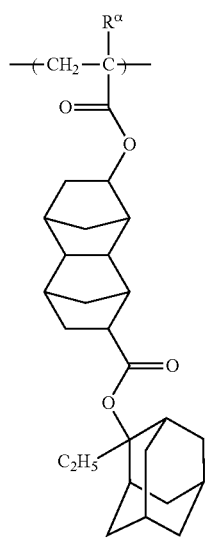
(a1-3-2)
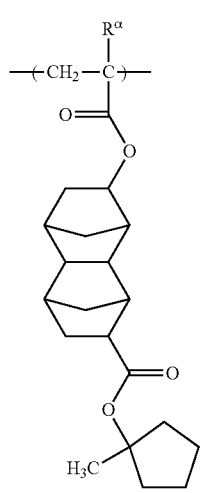
(a1-3-3)
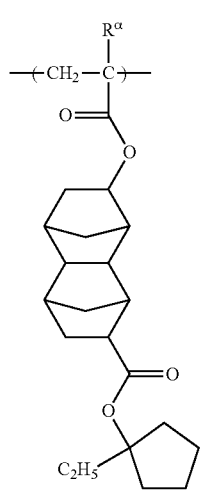
(a1-3-4)
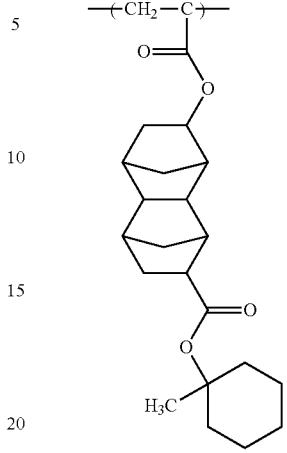
(a1-3-5)
(a1-3-6)
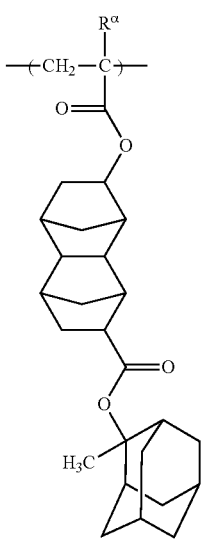
(a1-3-7)

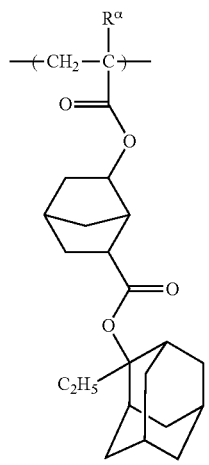 (a1-3-8)
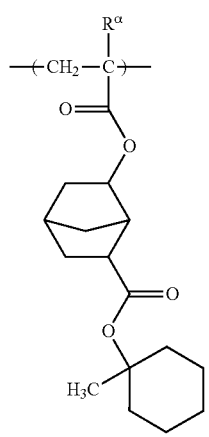 (a1-3-9)
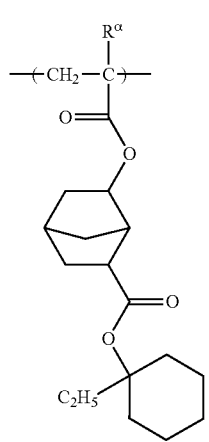 (a1-3-10)
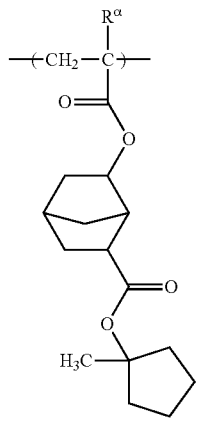 (a1-3-11)
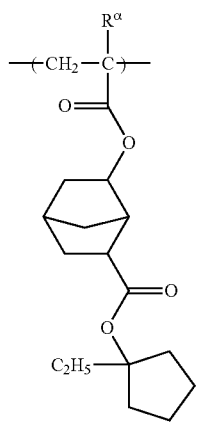 (a1-3-12)
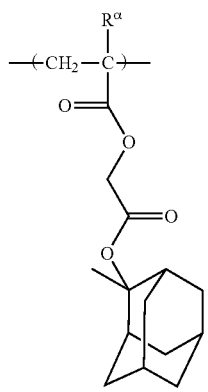 (a1-3-13)
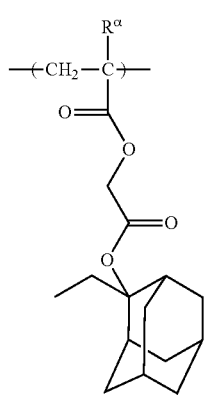 (a1-3-14)

(a1-3-15)
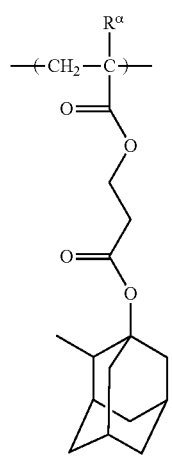
(a1-3-16)
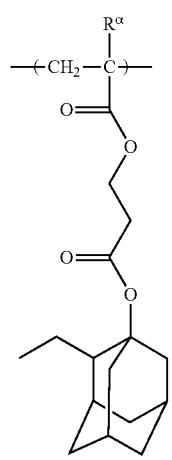
(a1-3-17)
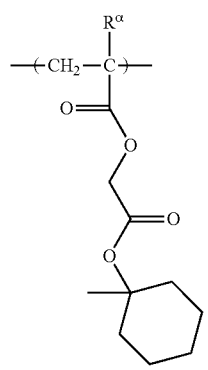
(a1-3-18)
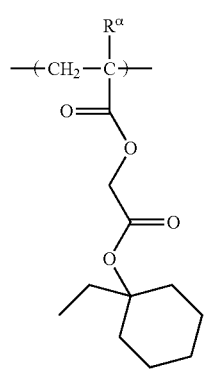
[Chemical Formula 39]
(a1-3-19)
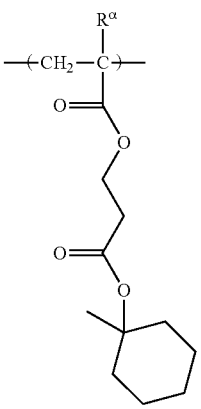
(a1-3-20)
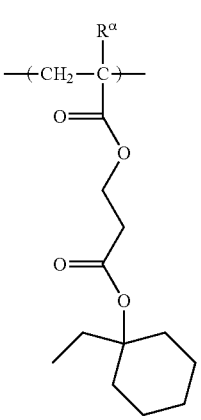
(a1-3-21)
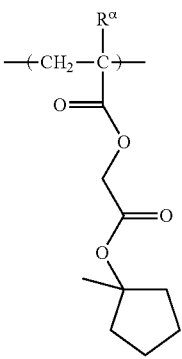
(a1-3-22)
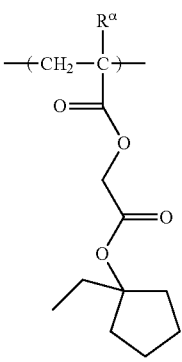

-continued
(a1-3-23) 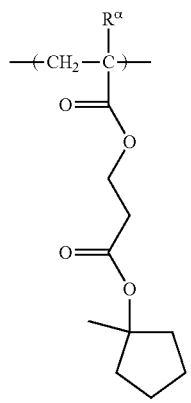
(a1-3-24) 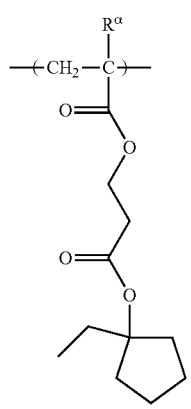
[Chemical Formula 40]
(a1-3-25) 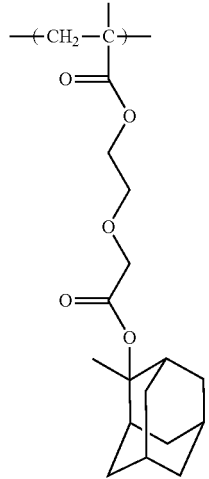
-continued
(a1-3-26) 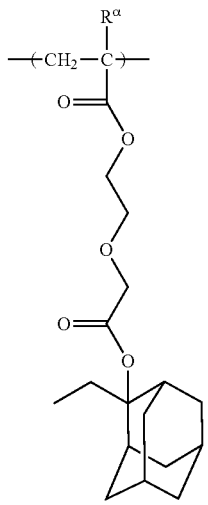
(a1-3-27) 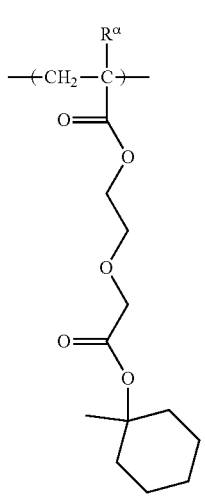
(a1-3-28) 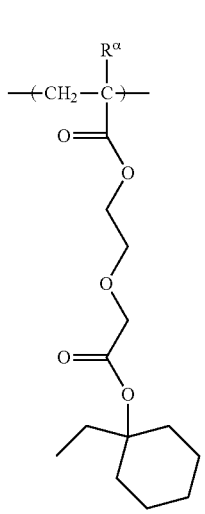

(a1-3-29)
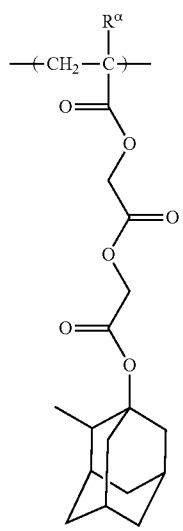
(a1-3-30)
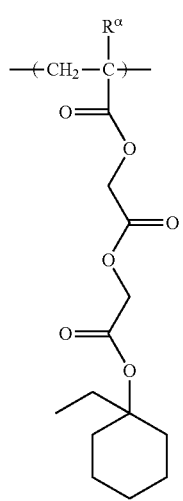
(a1-3-31)
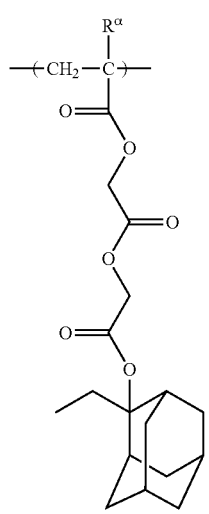
(a1-3-32)
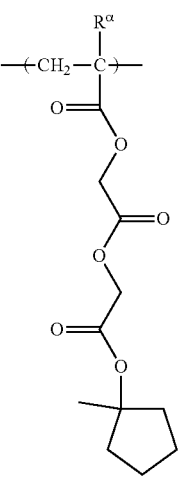
[Chemical Formula 41]
(a1-4-1)
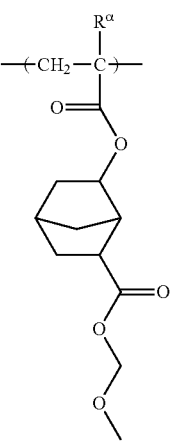
(a1-4-2)
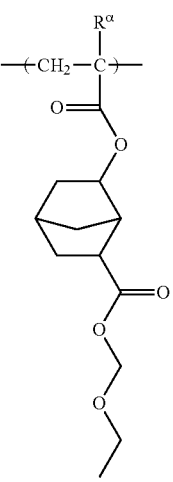

-continued
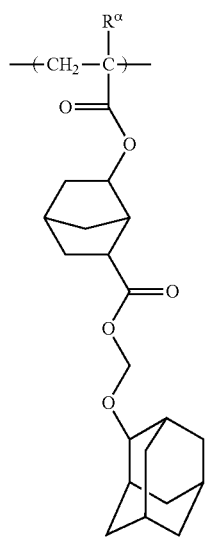 (a1-4-3)
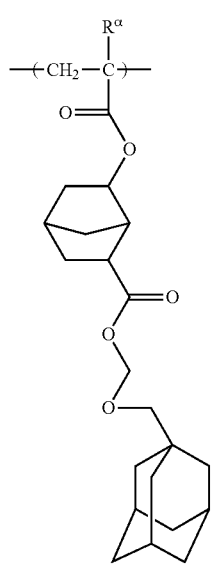 (a1-4-4)
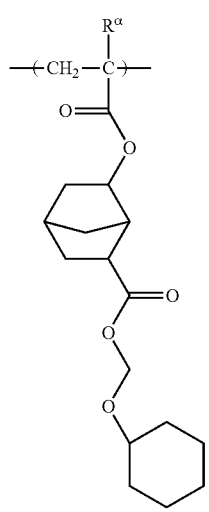 (a1-4-5)
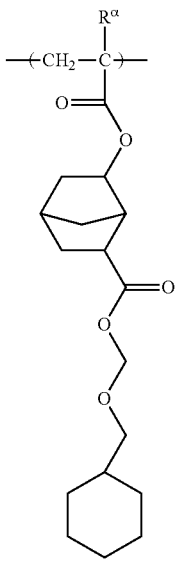 (a1-4-6)
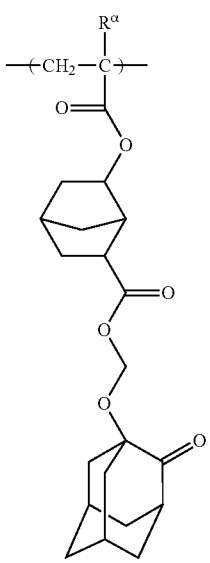 (a1-4-7)
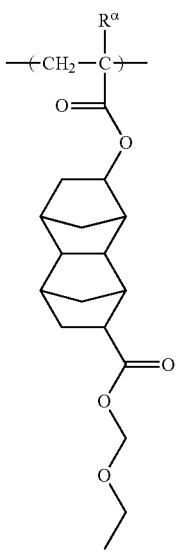 (a1-4-8)

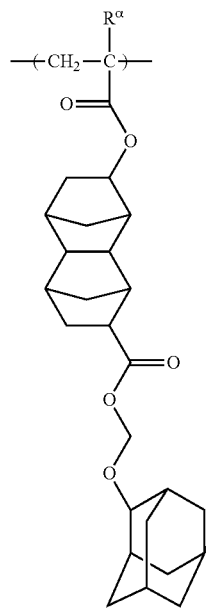
(a1-4-9)
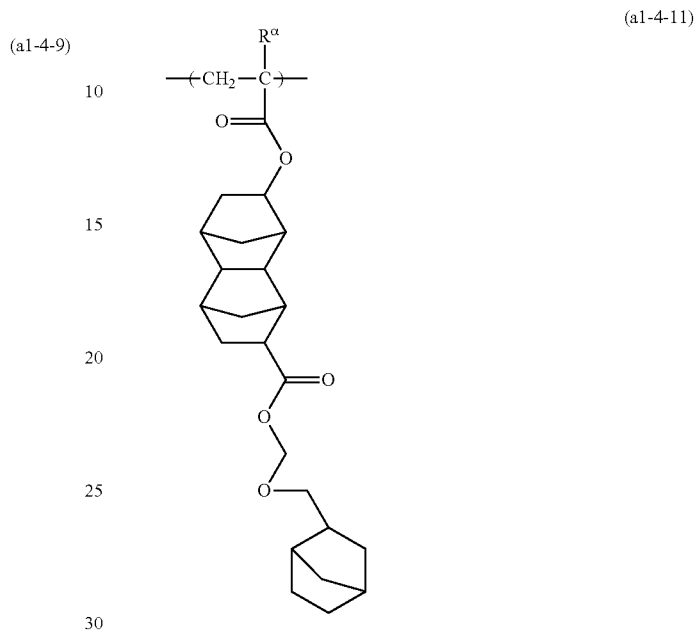
(a1-4-10)
(a1-4-11)
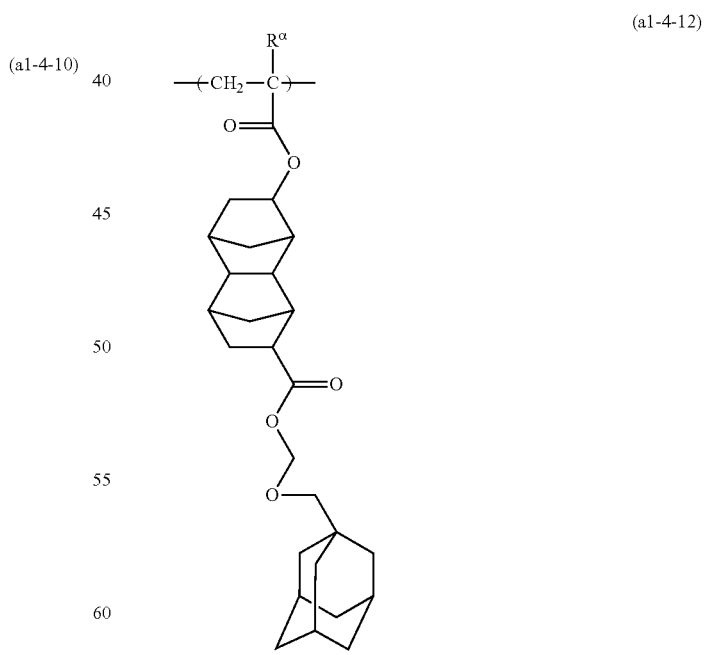
(a1-4-12)

(a1-4-13)

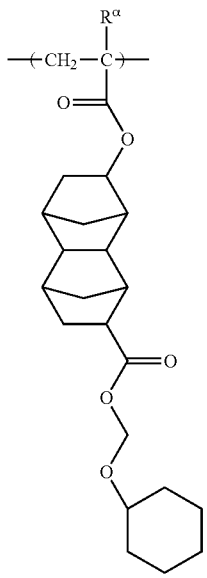

(a1-4-14)

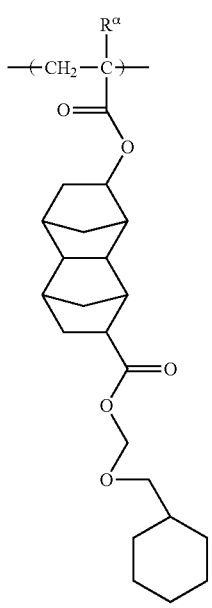

(a1-4-15)

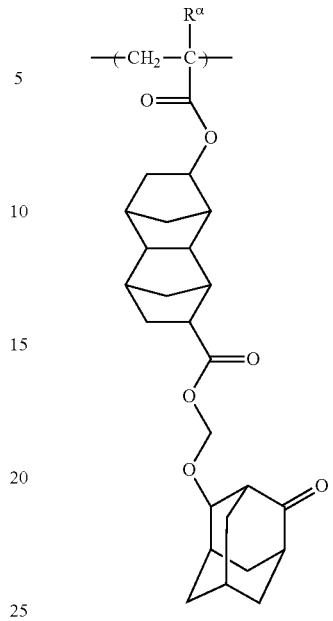

As the structural unit (a1), one type of structural unit may be used alone, or two or more types of structural units may be used in combination.

Among these, structural units represented by general formula (a1-1), (a1-2) or (a1-3) are preferable. More specifically, at least one structural unit selected from the group consisting of structural units represented by formulas (a1-1-1) to (a1-1-4), (a1-1-20) to (a1-1-23), (a1-2-1) to (a1-2-24) and (a1-3-25) to (a1-3-28) is more preferable.

Further, as the structural unit (a1), structural units represented by general formula (a1-1-01) shown below which includes the structural units represented by formulas (a1-1-1) to (a1-1-3) and (a1-1-26), structural units represented by general formula (a1-1-02) shown below which includes the structural units represented by formulas (a1-1-16), (a1-1-17), (a1-1-20) to (a1-1-23) and (a1-1-32), structural units represented by general formula (a1-3-01) shown below which include the structural units represented by formulas (a1-3-25) and (a1-3-26), structural units represented by general formula (a1-3-02) shown below which include the structural units represented by formulas (a1-1-27) and (a1-3-28), and structural units represented by general formula (a1-1-03) shown below which include the structural units represented by formulas (a1-1-29) and (a1-3-30) are also preferable.

[Chemical Formula 42]

(a1-1-01)

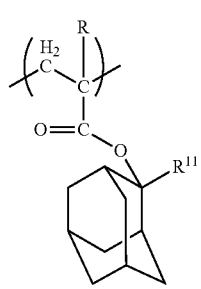

-continued (a1-1-02)

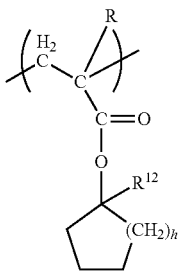

[Chemical Formula 45]

(a1-3-03)

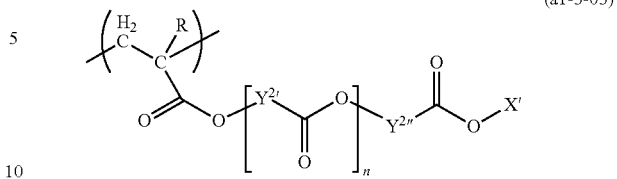

In the formulas, each R independently represents a hydrogen atom, an alkyl group of 1 to 5 carbon atoms or a halogenated alkyl group of 1 to 5 carbon atoms; $R^{11}$ represents an alkyl group of 1 to 5 carbon atoms; $R^{12}$ represents an alkyl group of 1 to 7 carbon atoms; and h represents an integer of 1 to 6.

In general formula (a1-1-01), R is the same as defined above. The alkyl group of 1 to 5 carbon atoms for $R^{11}$ is the same as defined for the alkyl group of 1 to 5 carbon atoms for R, and a methyl group, an ethyl group or an isopropyl group is preferable.

In general formula (a1-1-02), R is the same as defined above. The alkyl group of 1 to 5 carbon atoms for $R^{12}$ is the same as defined for the alkyl group of 1 to 5 carbon atoms for R, and a methyl group, an ethyl group or an isopropyl group is preferable. h is preferably 1 or 2, and most preferably 2.

[Chemical Formula 43]

(a1-3-01)

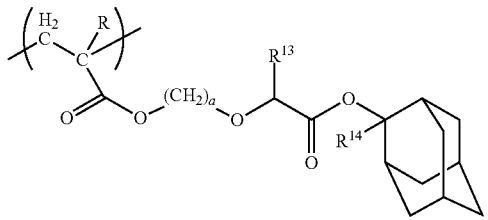

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; and a represents an integer of 1 to 10.

[Chemical Formula 44]

(a1-3-02)

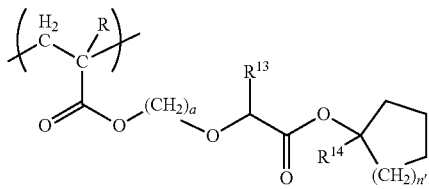

In the formula, R represents a hydrogen atom, an alkyl group of 1 to 5 carbon atoms or a halogenated alkyl group of 1 to 5 carbon atoms; $R^{14}$ is the same as defined above; $R^{13}$ represents a hydrogen atom or a methyl group; a represents an integer of 1 to 10; and n' represents an integer of 1 to 6.

In the formula, R is the same as defined above; each of $Y^{2'}$ and $Y^{2''}$ independently represents a divalent linking group; X' represents an acid dissociable group; and n represents an integer of 0 to 3.

In the above general formulas (a1-3-01) to (a1-3-03), R is the same as defined above.

$R^{13}$ is preferably a hydrogen atom.

n' is preferably 1 or 2, and is most preferably 2.

a is preferably an integer of 1 to 8, more preferably an integer of 2 to 5, and most preferably 2.

As the divalent linking group for $Y^{2'}$ and $Y^{2''}$, the same groups as those described above for $Y^{22}$ in general formula (a1-3) can be used.

$Y^{2'}$ is preferably a divalent hydrocarbon group which may have a substituent, is more preferably a linear aliphatic hydrocarbon group, and is still more preferably a linear alkylene group. Among such groups, a linear alkylene group of 1 to 5 carbon atoms is preferable, and a methylene group or ethylene group is the most desirable.

$Y^{2''}$ is preferably a divalent hydrocarbon group which may have a substituent, is more preferably a linear aliphatic hydrocarbon group, and is still more preferably a linear alkylene group. Among such groups, a linear alkylene group of 1 to 5 carbon atoms is preferable, and a methylene group or ethylene group is the most desirable.

As the acid dissociable group for X', the same groups as those described above can be used. X' is preferably a tertiary alkyl ester-type acid dissociable group, more preferably the aforementioned group which has a tertiary carbon atom on the ring structure of a cyclic alkyl group. Among the aforementioned groups, groups represented by the aforementioned general formulas (1-1) to (1-9) are preferable.

n represents an integer of 0 to 3, preferably an integer of 0 to 2, more preferably 0 or 1, and most preferably 1.

In the component (A1'), as the structural unit (a1), one type of structural unit may be used alone, or two or more types of structural units may be used in combination.

In the component (A1'), the amount of the structural unit (a1) based on the combined total of all structural units constituting the component (A1') is preferably 5 to 90 mol %, more preferably 10 to 85 mol %, and still more preferably 15 to 80 mol %. By making the amount of the structural unit (a1) at least as large as the lower limit of the above-mentioned range, a pattern can be easily formed using a resist composition prepared from the component (A1'). On the other hand, by making the amount of the structural unit (a1) no more than the upper limit of the above-mentioned range, a good balance can be achieved with the other structural units.

(Structural Unit (a2))

The structural unit (a2) is at least one structural unit selected from the group consisting of a structural unit derived from an acrylate ester which may have the hydrogen atom bonded to the carbon atom on the α-position substituted with a substituent and contains a —$SO_2$— containing cyclic group (hereafter, referred to as "structural unit ($a2^S$)") and a structural unit derived from an acrylate ester which may have the hydrogen atom bonded to the carbon atom on the α-position substituted with a substituent and contains a lactone-containing cyclic group (hereafter, referred to as structural unit (a2$^L$)").

By virtue of the structural unit (a2) containing a —SO$_2$— containing cyclic group or a lactone-containing cyclic group, a resist composition containing the component (A1') including the structural unit (a2) is capable of improving the adhesion of a resist film to a substrate, and increasing the compatibility with the developing solution containing water (especially, in the case of alkali developing process), thereby contributing to improvement of lithography properties.

Structural Unit (a2$^S$):

The structural unit (a2$^S$) is a structural unit derived from an acrylate ester containing a —SO$_2$— containing cyclic group and which may have the hydrogen atom bonded to the carbon atom on the α-position substituted with a substituent.

Here, an "—SO$_2$— containing cyclic group" refers to a cyclic group having a ring containing —SO$_2$— within the ring skeleton thereof, i.e., a cyclic group in which the sulfur atom (S) within —SO$_2$— forms part of the ring skeleton of the cyclic group. The ring containing —SO$_2$— within the ring skeleton thereof is counted as the first ring. A cyclic group in which the only ring structure is the ring that contains —SO$_2$— in the ring skeleton thereof is referred to as a monocyclic group, and a group containing other ring structures is described as a polycyclic group regardless of the structure of the other rings. The —SO$_2$— containing cyclic group may be either a monocyclic group or a polycyclic group.

As the —SO$_2$— containing cyclic group, a cyclic group containing —O—SO$_2$— within the ring skeleton thereof, i.e., a cyclic group containing a sultone ring in which —O—S— within the —O—SO$_2$— group forms part of the ring skeleton thereof is particularly desirable.

The —SO$_2$— containing cyclic group preferably has 3 to 30 carbon atoms, more preferably 4 to 20 carbon atoms, still more preferably 4 to 15 carbon atoms, and most preferably 4 to 12 carbon atoms. Herein, the number of carbon atoms refers to the number of carbon atoms constituting the ring skeleton, excluding the number of carbon atoms within a substituent.

The —SO$_2$— containing cyclic group may be either an —SO$_2$— containing aliphatic cyclic group or an —SO$_2$— containing aromatic cyclic group. An —SO$_2$— containing aliphatic cyclic group is preferred.

Examples of the —SO$_2$— containing aliphatic cyclic group include aliphatic cyclic groups in which part of the carbon atoms constituting the ring skeleton thereof has been substituted with an —SO$_2$— group or an —O—SO$_2$— group and has at least one hydrogen atom removed from the aliphatic hydrocarbon ring. More specific examples include groups in which at least one hydrogen atom has been removed from an aliphatic hydrocarbon ring in which a —CH$_2$— group that constitutes part of the ring skeleton has been substituted with an —SO$_2$— group, and groups in which at least one hydrogen atom has been removed from an aliphatic hydrocarbon ring in which a —CH$_2$—CH$_2$— group that constitutes part of the ring structure has been substituted with an —O—SO$_2$— group.

The alicyclic hydrocarbon group preferably has 3 to 20 carbon atoms, and more preferably 3 to 12 carbon atoms.

The alicyclic hydrocarbon group may be either a polycyclic group or a monocyclic group. As the monocyclic alicyclic hydrocarbon group, a group in which two hydrogen atoms have been removed from a monocycloalkane of 3 to 6 carbon atoms is preferable. Examples of the monocycloalkane include cyclopentane and cyclohexane. As the polycyclic alicyclic hydrocarbon group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —SO$_2$— containing cyclic group may have a substituent. Examples of the substituent include an alkyl group, an alkoxy group, a halogen atom, a halogenated alkyl group, a hydroxy group, an oxygen atom (=O), —COOR", —OC(=O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or ethyl group is preferable, and a methyl group is particularly desirable.

As the alkoxy group for the substituent, an alkoxy group of 1 to 6 carbon atoms is preferable. Further, the alkoxy group is preferably a linear alkoxy group or a branched alkoxy group. Specific examples of the alkoxy group include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxyl group.

More specific examples of the —SO$_2$— containing cyclic group include groups represented by general formulas (3-1) to (3-4) shown below.

[Chemical Formula 46]

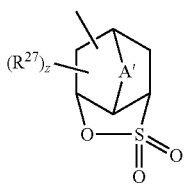
(3-1)

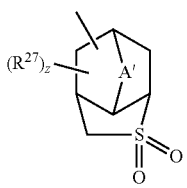
(3-2)

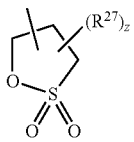
(3-3)

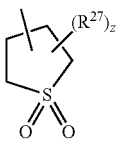
(3-4)

In the formulas, A' represents an oxygen atom, a sulfur atom or an alkylene group of 1 to 5 carbon atoms which may contain an oxygen atom or a sulfur atom; z represents an integer of 0 to 2; and R$^{27}$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms represented by A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—CH$_2$—, —CH$_2$—O—CH$_2$—, —S—CH$_2$— and —CH$_2$—S—CH$_2$—.

A' is preferably an alkylene group of 1 to 5 carbon atoms or —O—, more preferably an alkylene group of 1 to 5 carbon atoms, and most preferably a methylene group.

z represents an integer of 0 to 2, and is most preferably 0.

When z is 2, the plurality of R$^{27}$ may be the same or different from each other.

As the alkyl group, alkoxy group, halogenated alkyl group, —COOR", —OC(=O)R" and hydroxyalkyl group for R$^{27}$, the same alkyl groups, alkoxy groups, halogenated alkyl groups, —COOR", —OC(=O)R" and hydroxyalkyl groups as those described above as the substituent which the —SO$_2$— containing cyclic group may have can be used.

Specific examples of the cyclic groups represented by general formulas (3-1) to (3-4) are shown below. In the formulas shown below, "Ac" represents an acetyl group.

[Chemical Formula 47]

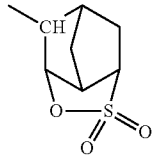
(3-1-1)

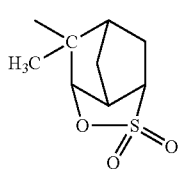
(3-1-2)

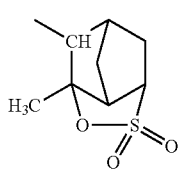
(3-1-3)

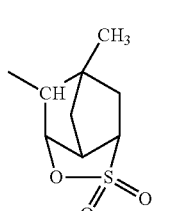
(3-1-4)

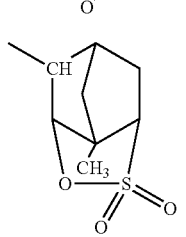
(3-1-5)

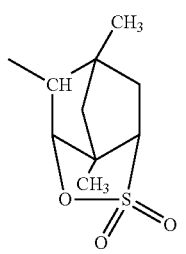
(3-1-6)

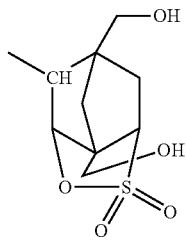
(3-1-7)

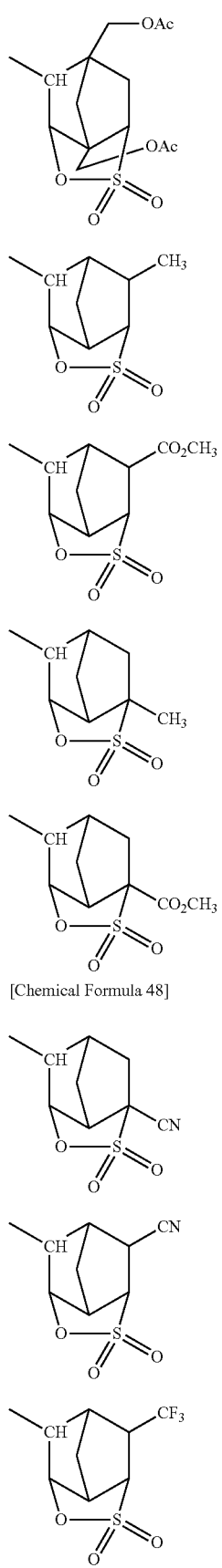
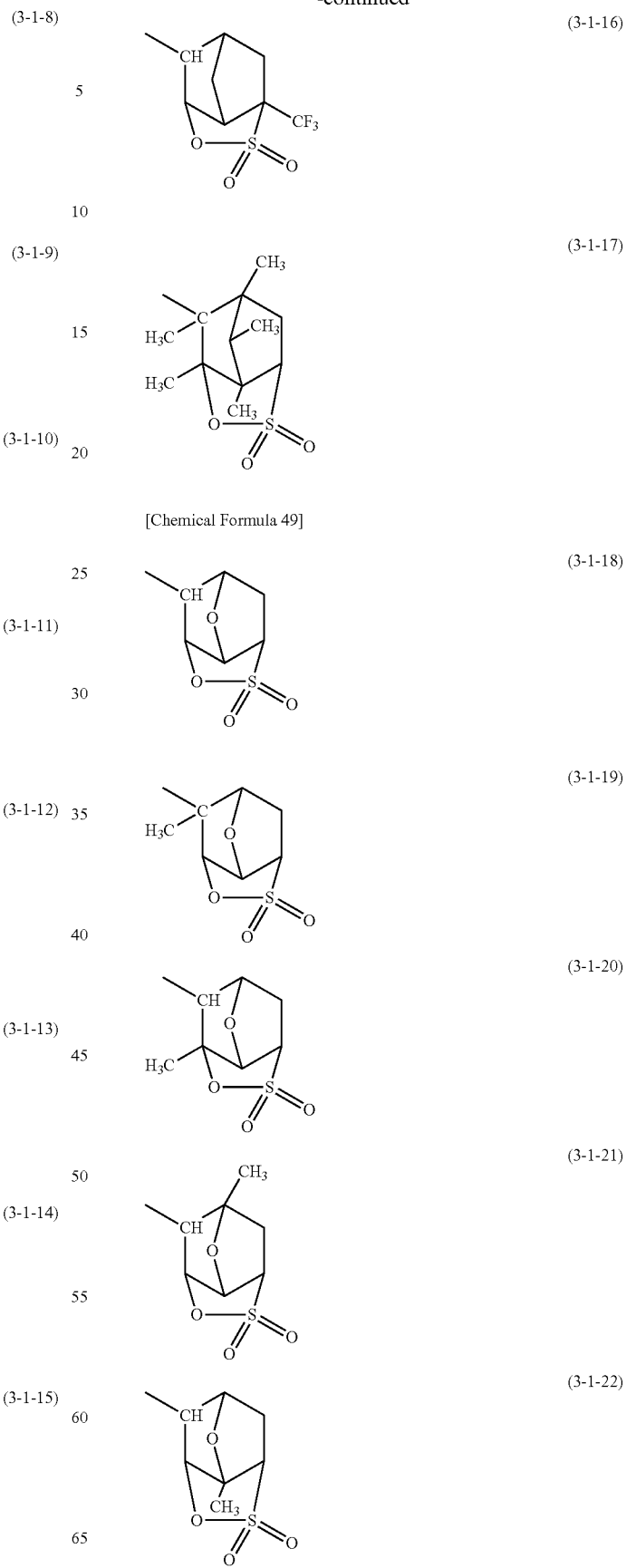

(3-1-23) 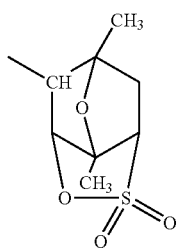

(3-1-24) 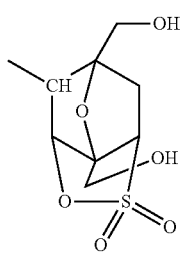

(3-1-25) 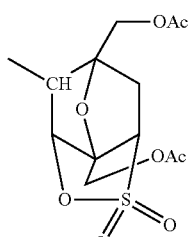

[Chemical Formula 50]

(3-1-26) 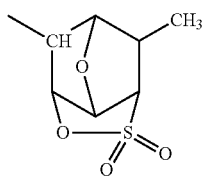

(3-1-27) 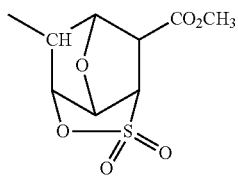

(3-1-28) 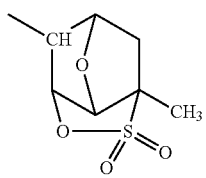

(3-1-29) 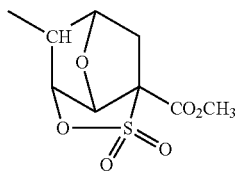

(3-1-30) 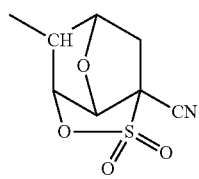

(3-1-31) 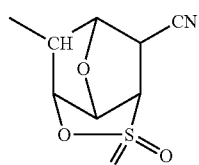

(3-1-32) 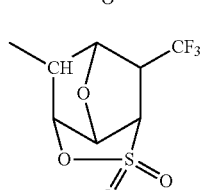

(3-1-33) 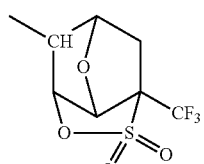

[Chemical Formula 51]

(3-2-1) 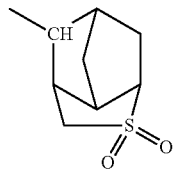

(3-2-2) 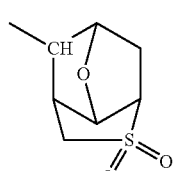

(3-3-1) 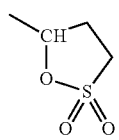

(3-4-1) 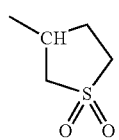

Of the groups shown above, the —$SO_2$— containing cyclic group is preferably a group represented by the general formula (3-1), more preferably at least one group selected from the group consisting of groups represented by the aforementioned chemical formulas (3-1-1), (3-1-18), (3-3-1) and (3-4-1), and most preferably a group represented by the aforementioned chemical formula (3-1-1).

More specific examples of the structural unit ($a2^S$) include structural units represented by general formula (a2-0) shown below.

[Chemical Formula 52]

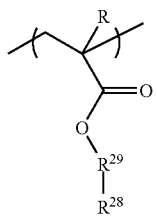

(a2-0)

In the formula, R represents a hydrogen atom, an alkyl group of 1 to 5 carbon atoms or a halogenated alkyl group of 1 to 5 carbon atoms; $R^{28}$ represents a —$SO_2$— containing cyclic group; and $R^{29}$ represents a single bond or a divalent linking group.

In genera formula (a2-0), R is the same as defined above.

$R^{28}$ is the same as defined for the aforementioned —$SO_2$— containing group.

$R^{29}$ may be either a single bond or a divalent linking group. A divalent linking group is preferable in terms of achieving superior effects for the present invention.

The divalent linking group for $R^{29}$ is not particularly limited, and examples thereof include the same divalent linking groups as those described above for $Y^{22}$ in the aforementioned formula (a1-0-2). Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^{22}$.

As the divalent linking group containing an ester bond, a group represented by general formula: —$R^{30}$—C(=O)—O— (in the formula, $R^{30}$ represents a divalent linking group) is particularly desirable. That is, the structural unit ($a2^S$) is preferably a structural unit represented by general formula (a2-0-1) shown below.

[Chemical Formula 53]

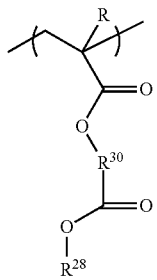

(a2-0-1)

In the formula, R and $R^{28}$ are the same as defined above; and $R^{30}$ represents a divalent linking group.

$R^{30}$ is not particularly limited, and examples thereof include the same divalent linking groups as those described above for $Y^{22}$ in the aforementioned formula (a1-0-2).

As the divalent linking group for $R^{30}$, a linear or branched alkylene group, a divalent alicyclic hydrocarbon group or a divalent linking group containing a hetero atom is preferable.

As the linear or branched alkylene group, the divalent alicyclic hydrocarbon group and the divalent linking group containing a hetero atom, the same linear or branched alkylene group, cyclic aliphatic hydrocarbon group and divalent linking group containing a hetero atom as those described above for $Y^{22}$ can be mentioned.

Of the above groups, a linear or branched alkylene group, or a divalent linking group containing an oxygen atom as a hetero atom is preferred.

As the linear alkylene group, a methylene group or an ethylene group is preferable, and a methylene group is particularly desirable.

As the branched alkylene group, an alkylmethylene group or an alkylethylene group is preferable, and —CH($CH_3$)—, —C($CH_3$)$_2$— or —C($CH_3$)$_2$$CH_2$— is particularly desirable.

As the divalent linking group containing an oxygen atom, a divalent linking group containing an ether bond or an ester bond is preferable, and a group represented by the aforementioned formula -$A^R$-O—$B^R$—, -[$A^R$-C(=O)—O]$_m$—$B^R$— or -$A^R$-O—C(=O)—$B^R$— is more preferable.

Among these, a group represented by the formula -$A^R$-O—C(=O)—$B^R$— is preferable, and a group represented by the formula: —($CH_2$)$_{c1}$—C(=O)—O—($CH_2$)$_{d1}$— is particularly desirable. c1 represents an integer of 1 to 5, and preferably 1 or 2. d1 represents an integer of 1 to 5, and preferably 1 or 2.

In particular, as the structural unit ($a2^S$), a structural unit represented by general formula (a0-1-11) or (a0-1-12) shown below is preferable, and a structural unit represented by general formula (a0-1-12) shown below is more preferable.

[Chemical Formula 54]

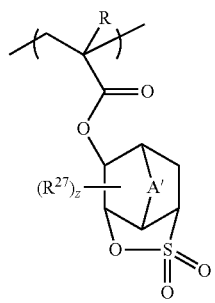

(a0-1-11)

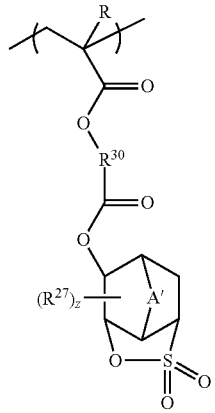

(a0-1-12)

In the formulas, R, A', $R^{27}$, z and $R^{30}$ are the same as defined above.

In general formula (a0-1-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a0-1-12), a structural unit represented by general formula (a0-1-12a) or (a0-1-12b) shown below is particularly desirable.

[Chemical Formula 55]

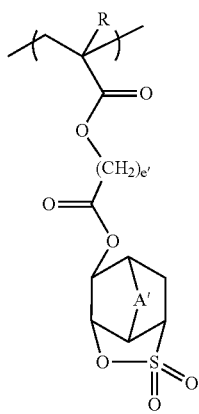

(a0-1-12a)

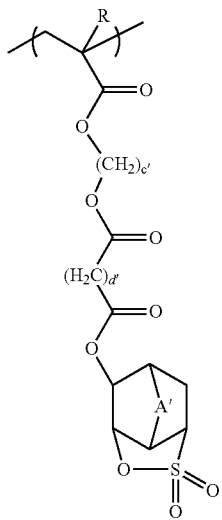

(a0-1-12b)

In the formulas, R and A' are the same as defined above; and each of c' to e' independently represents an integer of 1 to 3.

Structural Unit ($a2^L$):

The structural unit ($a2^L$) is a structural unit derived from an acrylate ester which may have the hydrogen atom bonded to the carbon atom on the α-position substituted with a substituent and contains a lactone-containing cyclic group.

The term "lactone-containing cyclic group" refers to a cyclic group including a ring containing a —O—C(O)— group within the ring structure thereof (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

There are no particular limitations on the lactone-containing cyclic group within the structural unit ($a2^L$), and an arbitrary lactone-containing cyclic group may be used. Specific examples of lactone-containing monocyclic groups include groups in which one hydrogen atom has been removed from a 4- to 6-membered lactone ring, including a group in which one hydrogen atom has been removed from β-propiolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

Examples of the structural unit ($a2^L$) include structural units represented by the aforementioned general formula (a2-0) in which the $R^{28}$ group has been substituted with a lactone-containing cyclic group. Specific examples thereof include structural units represented by general formulas (a2-1) to (a2-5) shown below.

[Chemical Formula 56]

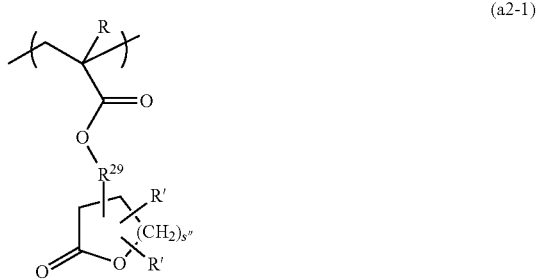

(a2-1)

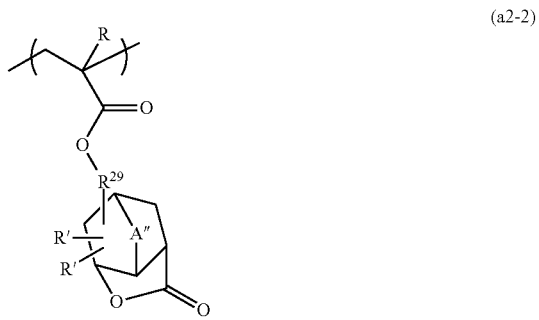

(a2-2)

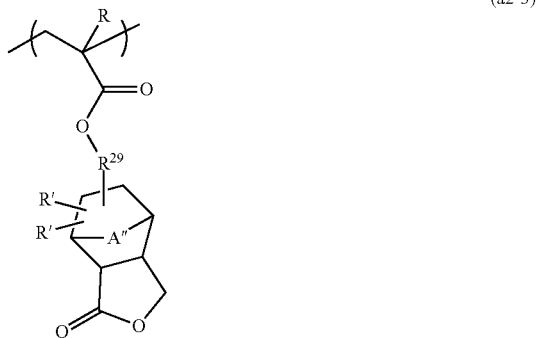

(a2-3)

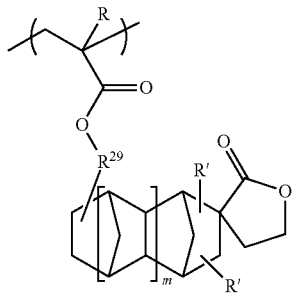

(a2-4)

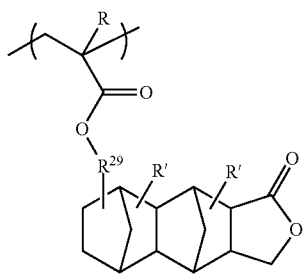

(a2-5)

In the formulas, R represents a hydrogen atom, an alkyl group of 1 to 5 carbon atoms or a halogenated alkyl group of 1 to 5 carbon atoms; each R' independently represents a hydrogen atom, an alkyl group of 1 to 5 carbon atoms, an alkoxy group of 1 to 5 carbon atoms or —COOR", wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above.

Examples of the alkyl group of 1 to 5 carbon atoms for R' include a methyl group, an ethyl group, a propyl group, an n-butyl group and a tert-butyl group.

Examples of the alkoxy group of 1 to 5 carbon atoms for R' include a methoxy group, an ethoxy group, an n-propoxy group, an iso-propoxy group, an n-butoxy group and a tert-butoxy group.

In terms of industrial availability, R' is preferably a hydrogen atom.

The alkyl group for R" may be a linear, branched or cyclic alkyl group.

When R" is a linear or branched alkyl group, the alkyl group preferably has 1 to 10 carbon atoms, and more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cyclic alkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and is more preferably an alkylene group of 1 to 5 carbon atoms or —O—. As the alkylene group of 1 to 5 carbon atoms, a methylene group or a dimethylmethylene group is more preferable, and a methylene group is particularly desirable.

$R^{29}$ is the same as defined for $R^{29}$ in the aforementioned general formula (a2-0).

In formula (a2-1), s" is preferably 1 or 2.

Specific examples of the structural units represented by general formulas (a2-1) to (a2-5) are shown below. In the formulas shown below, $R^{\alpha}$ represents a hydrogen atom, a methyl group or a trifluoromethyl group.

[Chemical Formula 57]

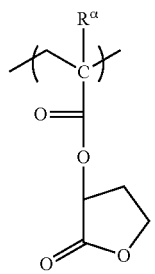

(a2-1-1)

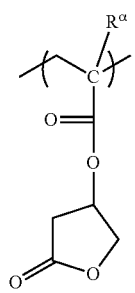

(a2-1-2)

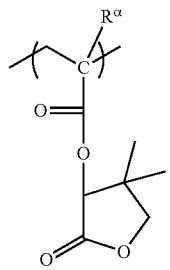

(a2-1-3)

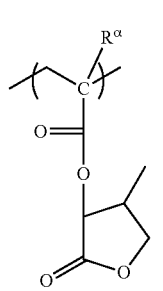

(a2-1-4)

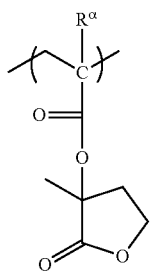 (a2-1-5)
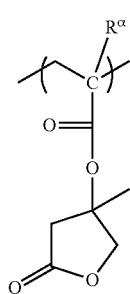 (a2-1-6)
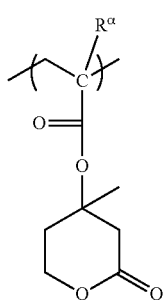 (a2-1-7)
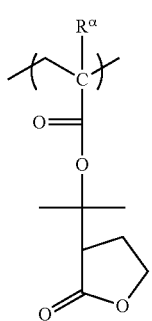 (a2-1-8)
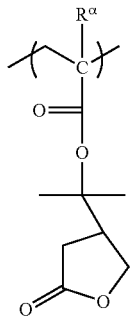 (a2-1-9)
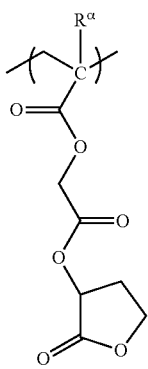 (a2-1-10)
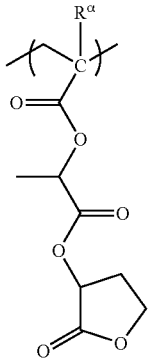 (a2-1-11)
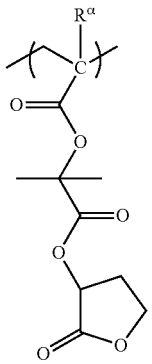 (a2-1-12)
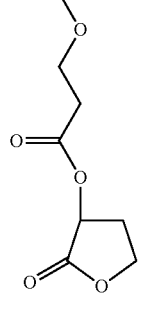 (a2-1-13)

[Chemical Formula 58]
(a2-2-1) 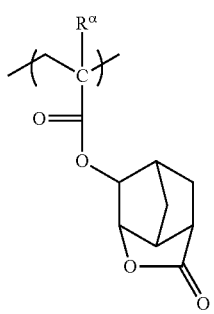
(a2-2-2) 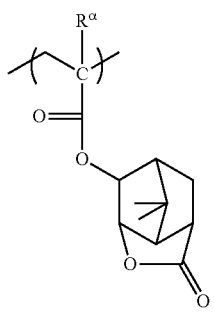
(a2-2-3) 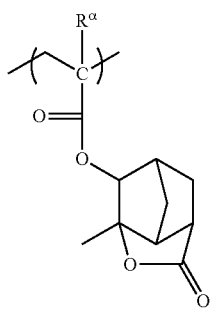
(a2-2-4) 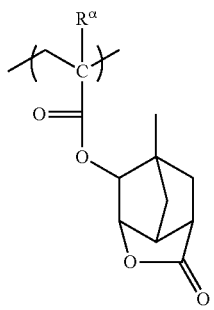
(a2-2-5) 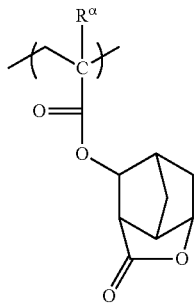
(a2-2-6) 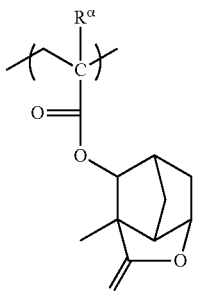
(a2-2-7) 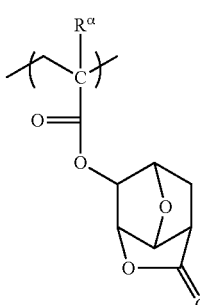
(a2-2-8) 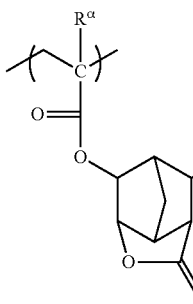
(a2-2-9) 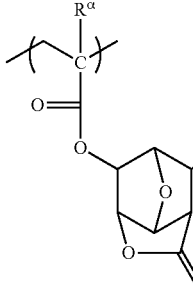
(a2-2-10) 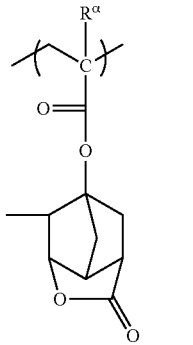

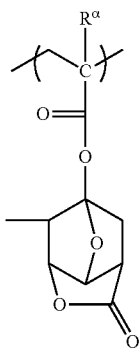
(a2-2-11)
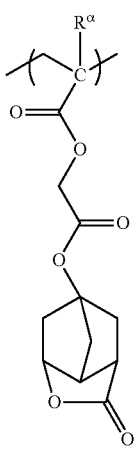
(a2-2-12)
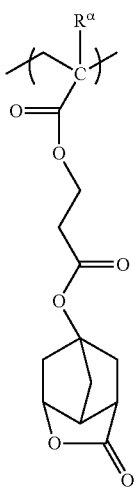
(a2-2-13)
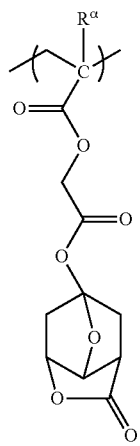
(a2-2-14)
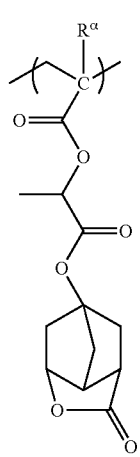
(a2-2-15)
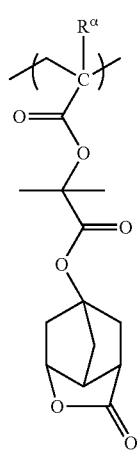
(a2-2-16)

(a2-2-17)
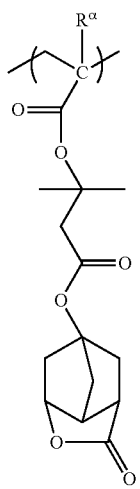
[Chemical Formula 59]
(a2-3-1)
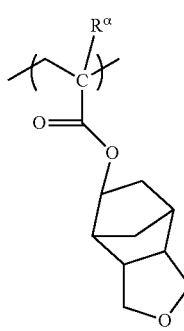
(a2-3-2)
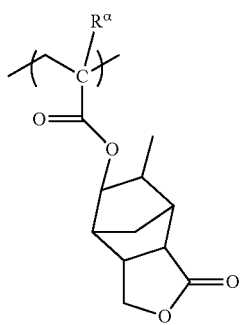
(a2-3-3)
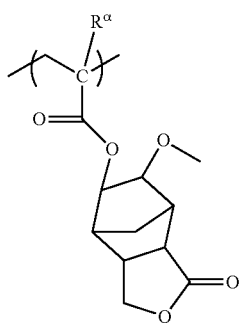
(a2-3-4)
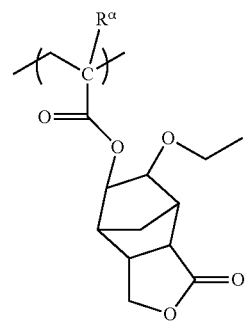
(a2-3-5)
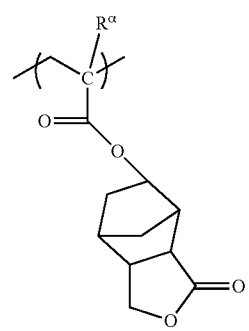
[Chemical Formula 60]
(a2-4-1)
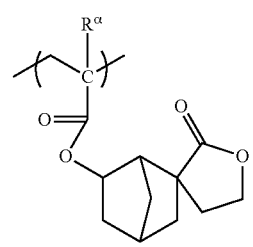
(a2-4-2)
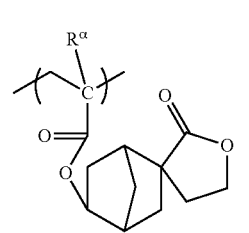
(a2-4-3)
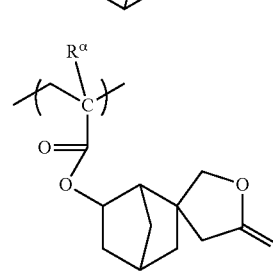
(a2-4-4)
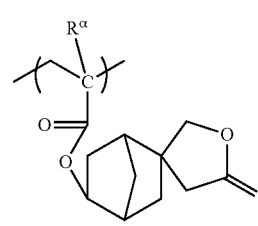

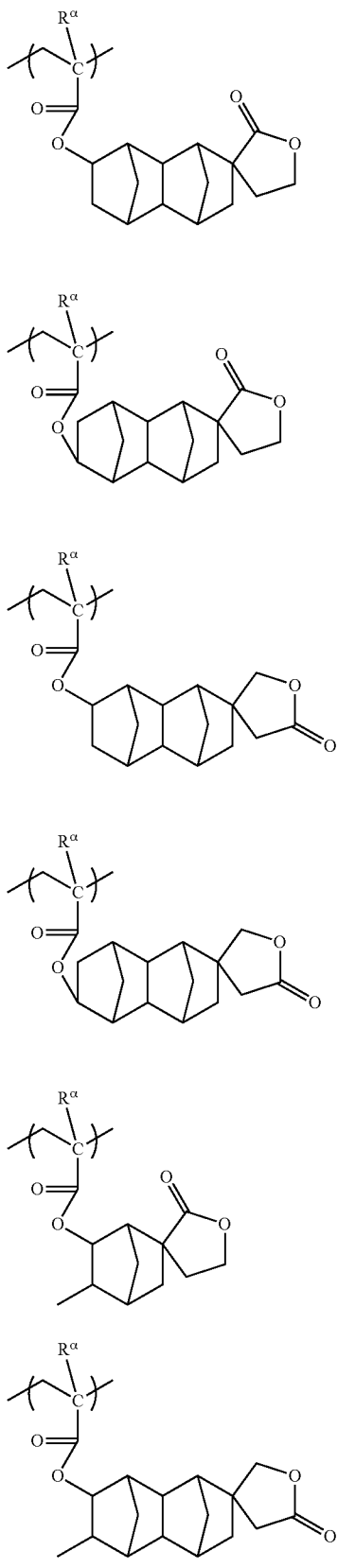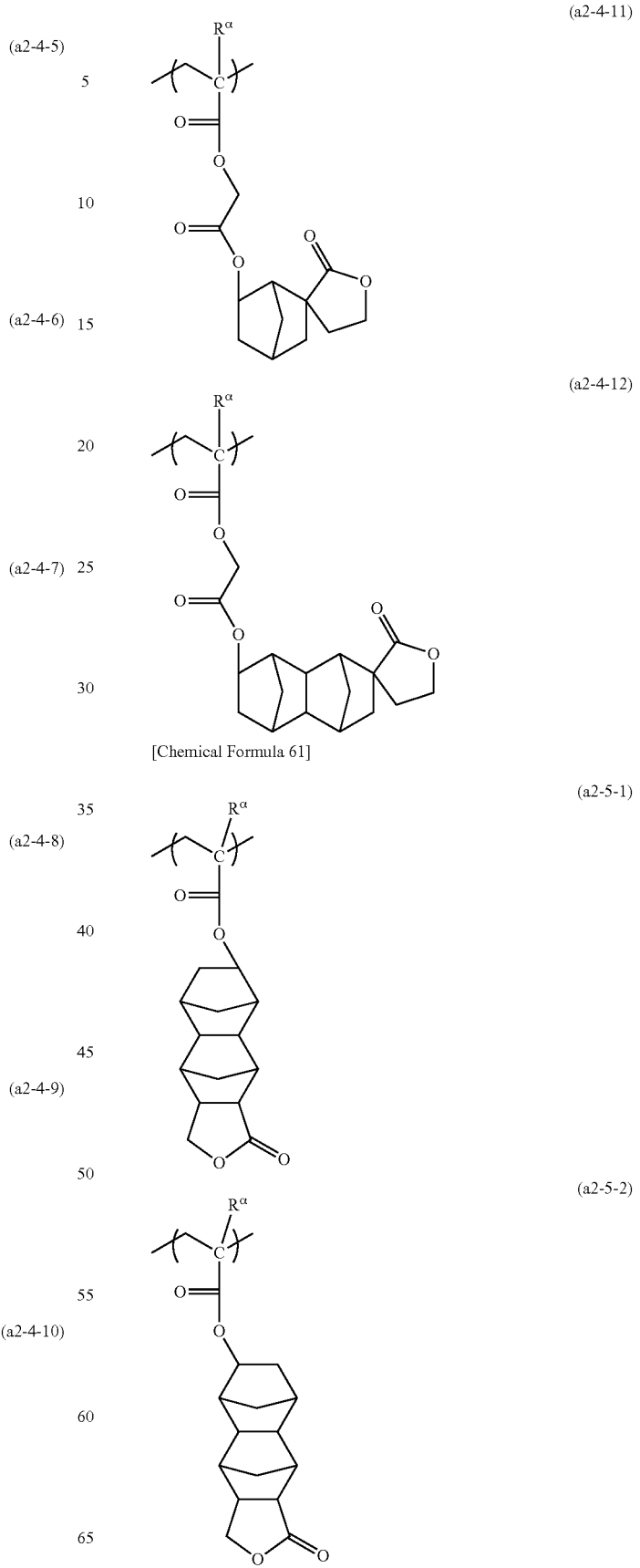

(a2-5-3)

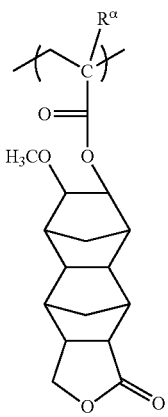

(a2-5-4)

(a2-5-5)

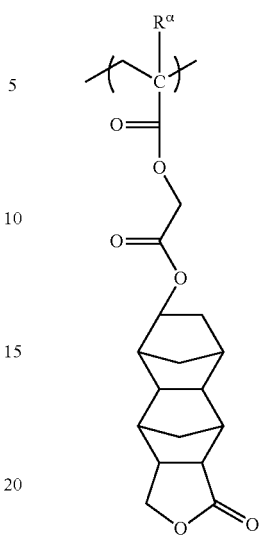

(a2-5-6)

As the structural unit (a2$^L$), it is preferable to include at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and most preferably at least one structural unit selected from the group consisting of structural units represented by the aforementioned general formulas (a2-1) and (a2-3).

Of these, it is particularly preferable to use at least one structural unit selected from the group consisting of structural units represented by the aforementioned formulas (a2-1-1), (a2-1-2), (a2-2-1), (a2-2-7), (a2-2-12), (a2-2-14), (a2-3-1) and (a2-3-5).

In the component (A1'), as the structural unit (a2), one type of structural unit may be used alone, or two or more types of structural units may be used in combination. For example, as the structural unit (a2), the structural unit (a2$^S$) may be used alone, the structural unit (a2$^L$) may be used alone, or the structural units (a2$^S$) and (a2$^L$) may be used in combination. Further, as the structural unit (a2$^S$) or the structural unit (a2$^L$), one type of structural unit may be used alone, or two or more types of structural units may be used in combination.

When the component (A1') contains the structural unit (a2), the amount of the structural unit (a2) within the component (A1') based on the combined total of all structural units constituting the component (A1') is preferably 1 to 80 mol %, more preferably 10 to 70 mol %, still more preferably 10 to 65 mol %, and most preferably 10 to 60 mol %. When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

(Structural Unit (a3))

The structural unit (a3) is a structural unit derived from an acrylate ester which may have the hydrogen atom bonded to the carbon atom on the α-position substituted with a substituent and contains a polar group-containing aliphatic hydrocarbon group.

When the component (A1') includes the structural unit (a3), the hydrophilicity of the component (A') is improved, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group containing a hydroxyl group, cyano group, carboxyl group or a hydroxyalkyl group in which some of the hydrogen atoms of the alkyl group have been substituted with fluorine atoms are particularly desirable. Examples of the polycyclic group include groups in which two or more hydrogen atoms have been removed from a bicycloalkane, tricycloalkane or tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the hydrocarbon group is a polycyclic group, structural units represented by formulas (a3-1), (a3-2) and (a3-3) shown below are preferable.

[Chemical Formula 62]

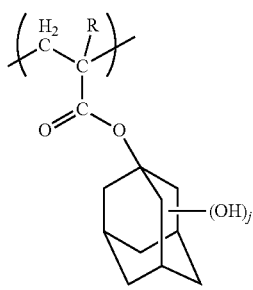

(a3-1)

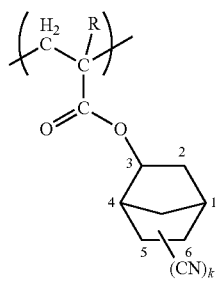

(a3-2)

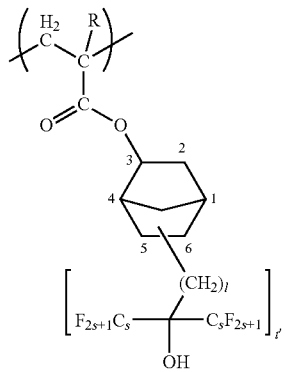

(a3-3)

In the formulas, R is the same as defined above; j is an integer of 1 to 3; k is an integer of 1 to 3; t' is an integer of 1 to 3; l is an integer of 1 to 5; and s is an integer of 1 to 3.

In formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-2), k is preferably 1. The cyano group is preferably bonded to the 5th or 6th position of the norbornyl group.

In formula (a3-3), t' is preferably 1. l is preferably 1. s is preferably 1. Further, it is preferable that a 2-norbornyl group or 3-norbornyl group be bonded to the terminal of the carboxyl group of the acrylic acid. The fluorinated alkyl alcohol is preferably bonded to the 5th or 6th position of the norbornyl group.

As the structural unit (a3), one type of structural unit may be used alone, or two or more types of structural units may be used in combination.

When the component (A1') contains the structural unit (a3), the amount of the structural unit (a3) within the component (A1') based on the combined total of all structural units constituting the component (A1') is preferably 1 to 50 mol %, more preferably 3 to 45 mol %, and still more preferably 5 to 40 mol %. By making the amount of the structural unit (a3) at least as large as the lower limit of the above-mentioned range, the effect of using the structural unit (a3) can be satisfactorily achieved. On the other hand, by making the amount of the structural unit (a3) no more than the upper limit of the above-mentioned range, a good balance can be achieved with the other structural units.

(Other Structural Units)

The component (A1') may also include a structural unit other than the above-mentioned structural units (a0) to (a3)

(hereafter, referred to as "structural unit (a4)"), as long as the effects of the present invention are not impaired.

As the structural unit (a4), any other structural unit which cannot be classified as one of the above structural units (a0) to (a3) can be used without any particular limitations, and any of the multitude of conventional structural units used within resist resins designed for use with ArF excimer lasers or KrF excimer lasers (and particularly for ArF excimer lasers) can be used.

Preferable examples of the structural unit (a4) include a structural unit derived from an acrylate ester which contains a non-acid-dissociable aliphatic polycyclic group and may have the hydrogen atom bonded to the carbon atom on the α-position substituted with a substituent, a structural unit derived from a styrene monomer and a structural unit derived from a vinylnaphthalene monomer. Examples of this polycyclic group include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (a4) include units with structures represented by general formulas (a4-1) to (a4-5) shown below.

[Chemical Formula 63]

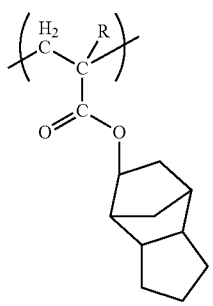

(a4-1)

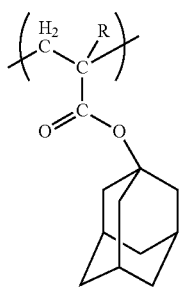

(a4-2)

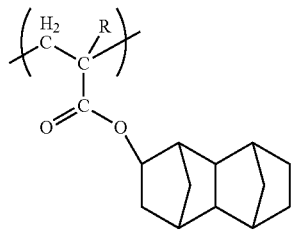

(a4-3)

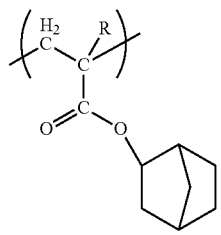

(a4-4)

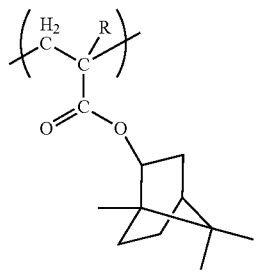

(a4-5)

In the formulas, R is the same as defined above.

As the structural unit (a4), one type of structural unit may be used alone, or two or more types of structural units may be used in combination.

When the structural unit (a4) is included in the component (A1'), the amount of the structural unit (a4) based on the combined total of all structural units constituting the component (A1') is preferably 1 to 20 mol %, more preferably 1 to 15 mol %, and still more preferably 1 to 10 mol %.

The component (A1') is preferably a copolymer that further includes the structural unit (a1), in addition to the structural unit (a0).

Examples of such copolymers include a copolymer consisting of the structural units (a0) and (a1); a copolymer consisting of the structural units (a0), (a1) and (a2); a copolymer consisting of the structural units (a0), (a1) and (a3); and a copolymer consisting of the structural units (a0), (a1), (a2) and (a3).

In the present invention, it is particularly desirable that the component (A1') include a suitable combination of structural units represented by general formula (A1'-1) and (A1'-2) shown below. In general formulas shown below, R, $R^{29}$, s'', $R^{11}$, j, $R^1$, A, $R^3$, n0 and $M'^+$ are the same as defined above. $R^{4a}$ is an aliphatic cyclic group which may have a substituent, and the same aliphatic cyclic groups as those described above for $R^4$ can be used. The plurality of R in the formulas may be the same or different from each other.

Further, in formula (A1'-2), $R^{4a}$ represents an acid dissociable group.

[Chemical Formula 64]

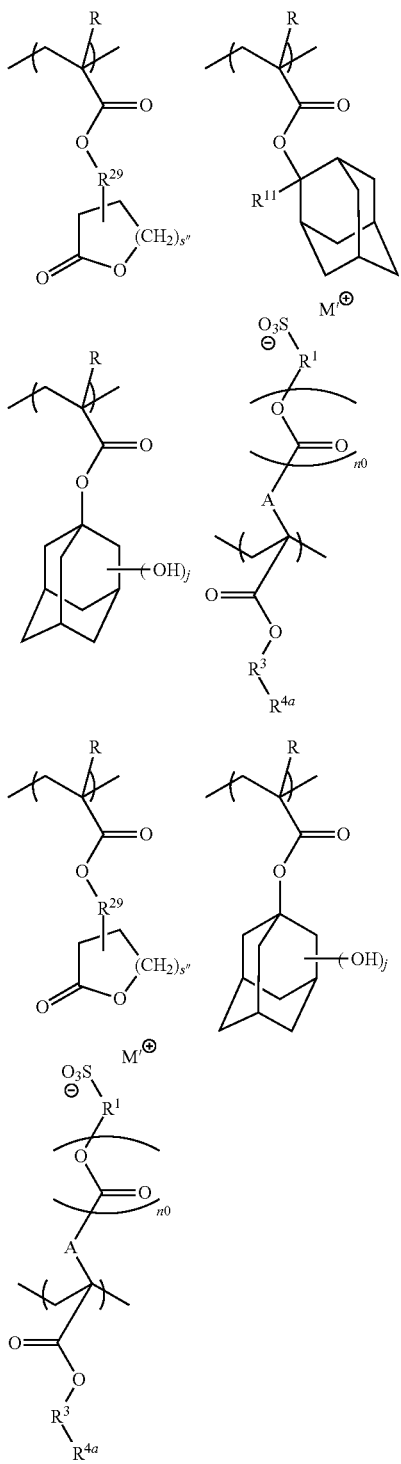

The weight average molecular weight (Mw) (the polystyrene equivalent value determined by gel permeation chromatography) of the component (A1') is not particularly limited, but is preferably within a range from 1,000 to 50,000, more preferably from 1,500 to 30,000, and most preferably from 2,500 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the component (A1') is not particularly limited, but is preferably within a range from 1.0 to 5.0, more preferably from 1.0 to 3.0, and most preferably 1.2 to 2.5.

Here, Mn is the number average molecular weight.

In the component (A), as the component (A1'), one type may be used alone, or two or more types may be used in combination.

In the component (A'), the amount of the component (A1'), based on the total weight of the component (A'), is preferably at least 25% by weight, more preferably 50% by weight or more, still more preferably 75% by weight or more, and may even be 100% by weight. When the amount of the component (A1') is 25% by weight or more, various lithography properties are improved.

[Component (A2)]

In the resist composition of the present invention, the component (A') may contain a base component which does not correspond with the component (A1') and which exhibits changed solubility in a developing solution under the action of acid (hereinafter referred to as "component (A2)").

As the component (A2), a low molecular weight compound that has a molecular weight of at least 500 but less than 2,500, contains a hydrophilic group, and also contains an acid dissociable group such as those listed above in the description of the component (A1') is preferred. Specific examples include compounds containing a plurality of phenol skeletons in which a part of the hydrogen atoms within hydroxyl groups have been substituted with the aforementioned acid dissociable groups.

Preferred examples of the component (A2) include low molecular weight phenol compounds in which a portion of the hydroxyl group hydrogen atoms have been substituted with an aforementioned acid dissociable group. These types of compounds are known, for example, as sensitizers or heat resistance improvers for use in non-chemically amplified g-line or i-line resists, and any of these compounds may be used.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers, tetramers, pentamers and hexamers of formalin condensation products of phenols such as phenol, m-cresol, p-cresol and xylenol. Needless to say, the low molecular weight phenol compound is not limited to these examples. In particular, a phenol compound having 2 to 6 triphenylmethane skeletons is preferable in terms of resolution and LWR.

Also, there are no particular limitations on the acid dissociable group, and suitable examples include the groups described above.

As the component (A2), one type may be used alone, or two or more types may be used in combination.

In the resist composition 1 of the present invention, the component (A') may use either one type of component, or a combination of two or more components.

Of the examples shown above, as the component (A'), it is preferable to use one containing the component (A1').

In the resist composition 1 of the present invention, the amount of the component (A') can be appropriately adjusted depending on the thickness of the resist film to be formed, and the like.

<Optional Component—Component (B)>

The resist composition 1 of the present invention may also include an acid generator component (B) which generates acid upon irradiation (hereafter referred to as "component (B)").

When the resist composition 1 of the present invention includes the component (B), as the component (B), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, for example, a compound represented by general formula (b-1) or (b-2) shown below can be used.

[Chemical Formula 65]

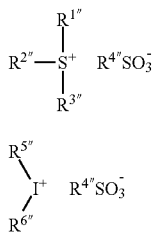

In the formulas above, $R^{1''}$ to $R^{3''}$, $R^{5''}$ and $R^{6''}$ each independently represents an aryl group or alkyl group, wherein two of $R^{1''}$ to $R^{3''}$ in formula (b-1) may be bonded to each other to form a ring with the sulfur atom in the formula; and $R^{4''}$ represents an alkyl group, a halogenated alkyl group, an aryl group or an alkenyl group which may have a substituent, with the proviso that at least one of $R^{1''}$ to $R^{3''}$ represents an aryl group, and at least one of $R^{5''}$ and $R^{6''}$ represents an aryl group.

In general formulas (b-1) and (b-2), $R^{1''}$ to $R^{3''}$, $R^{5''}$ and $R^{6''}$ are respectively the same as defined for $R^{1''}$ to $R^{3''}$, $R^{5''}$ and $R^{6''}$ in the aforementioned general formulas (c1) and (c-2).

In formulas (b-1) and (b-2), $R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms relative to the total number of halogen atoms and hydrogen atoms within the halogenated alkyl group (namely, the halogenation ratio (%)) is preferably within a range from 10 to 100%, more preferably from 50 to 100%, and most preferably 100%. A higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, and a group represented by the formula $X-Q^1-$ (in the formula, $Q^1$ represents a divalent linking group containing an oxygen atom; and X represents a hydrocarbon group of 3 to 30 carbon atoms which may have a substituent).

Examples of the halogen atom and alkyl group include the same halogen atoms and alkyl groups as those described above with respect to the halogenated alkyl group for $R^{4''}$.

Examples of the hetero atom include an oxygen atom, a nitrogen atom, and a sulfur atom.

In the group represented by formula $X-Q^1-$, $Q^1$ represents a divalent linking group containing an oxygen atom.

$Q^1$ may contain an atom other than an oxygen atom. Examples of atoms other than an oxygen atom include a carbon atom, a hydrogen atom, a sulfur atom and a nitrogen atom.

Examples of the divalent linking groups containing an oxygen atom include non-hydrocarbon, oxygen atom-containing linking groups such as an oxygen atom (an ether bond; —O—), an ester bond (—C(=O)—O—), an amido bond (—C(=O)—NH—), a carbonyl group (—C(=O)—) and a carbonate group (—O—C(=O)—O—); and combinations of the aforementioned non-hydrocarbon, hetero atom-containing linking groups with an alkylene group.

Specific examples of the combinations of the aforementioned non-hydrocarbon, hetero atom-containing linking groups and an alkylene group include —$R^{91}$—O—, —$R^{92}$—O—C(=O)—, —C(=O)—O—$R^{93}$—O—C(=O)— (in the formulas, each of $R^{91}$ to $R^{93}$ independently represents an alkylene group).

The alkylene group for $R^{91}$ to $R^{93}$ is preferably a linear or branched alkylene group, and preferably has 1 to 12 carbon atoms, more preferably 1 to 5 carbon atoms, and most preferably 1 to 3 carbon atoms.

Specific examples of the alkylene group include a methylene group [—$CH_2$—], alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—, an ethylene group [—$CH_2CH_2$—], alkylethylene groups such as —CH($CH_3$)$CH_2$—, —CH($CH_3$)CH($CH_3$)—, —C($CH_3$)$_2CH_2$— and —CH($CH_2CH_3$)$CH_2$—, a trimethylene group (n-propylene group) [—$CH_2CH_2CH_2$—], alkyltrimethylene groups such as —CH($CH_3$)$CH_2CH_2$— and —$CH_2$CH($CH_3$)$CH_2$—, a tetramethylene group [—$CH_2CH_2CH_2CH_2$—], alkyltetramethylene groups such as —CH($CH_3$)$CH_2CH_2CH_2$— and —$CH_2$CH($CH_3$)$CH_2CH_2$—, and a pentamethylene group [—$CH_2CH_2CH_2CH_2CH_2$—].

$Q^1$ is preferably a divalent linking group containing an ester bond or ether bond, and more preferably a group represented by —$R^{91}$—O—, —$R^{92}$—O—C(=O)— or —C(=O)—O—$R^{93}$—O—C(=O)—.

In the group represented by the formula X-$Q^1$-, the hydrocarbon group for X may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within substituents is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atoms, more preferably 1 or 2 carbon atoms, and most preferably 1 carbon atom.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, a n-propoxy group, an iso-propoxy group, a n-butoxy group or a tert-butoxy group, and most preferably a methoxy group or an ethoxy group.

Examples of the halogen atom as the substituent for the aromatic hydrocarbon group include a fluorine atom, chlorine atom, bromine atom and iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for X may be either a saturated aliphatic hydrocarbon group, or an unsaturated aliphatic hydrocarbon group. Further, the aliphatic hydrocarbon group may be linear, branched or cyclic.

In the aliphatic hydrocarbon group for X, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for X, there is no particular limitation as long as it is an atom other than a carbon atom and a hydrogen atom. Examples of hetero atoms include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, a n-propoxy group, an iso-propoxy group, a n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Examples of the aforementioned halogenated alkyl group include a group in which part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples of the aliphatic cyclic group include groups in which one or more hydrogen atoms have been removed from a monocycloalkane, or a polycycloalkane such as a bicycloalkane, tricycloalkane or tetracycloalkane. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by the aforementioned formulas (L1) to (L6) and (S1) to (S4).

In the present invention, X is preferably a cyclic group which may have a substituent. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by the aforementioned formulas (L2) to (L6), (S3) and (S4) are preferable.

In the present invention, $R^{4''}$ preferably has X-$Q^1$- as a substituent. In this case, $R^{4''}$ is preferably a group represented by formula X-$Q^1$-$Y^0$—[wherein $Q^1$ and X are the same as defined above; and $Y^0$ represents an alkylene group of 1 to 4 carbon atoms which may have a substituent, or a fluorinated alkylene group of 1 to 4 carbon atoms which may have a substituent].

In the group represented by the formula X-$Q^1$-$Y^0$—, examples of the alkylene group represented by $Y^0$ include those alkylene groups described above for $Q^1$ in which the number of carbon atoms is within a range from 1 to 4.

As the fluorinated alkylene group, the aforementioned alkylene group in which part or all of the hydrogen atoms has been substituted with fluorine atoms can be used.

Specific examples of $Y^0$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—, —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—, —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$— and —$C(CH_3)(CH_2CH_3)$—.

$Y^0$ is preferably a fluorinated alkylene group, and particularly preferably a fluorinated alkylene group in which the carbon atom bonded to the adjacent sulfur atom is fluorinated. Examples of such fluorinated alkylene groups include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CH_2CF_2$—, —$CH_2CH_2CF_2$—, —$CH_2CF_2CF_2$—, —$CH_2CH_2CH_2CF_2$—, —$CH_2CH_2CF_2CF_2$— and —$CH_2CF_2CF_2CF_2$—.

Of these, —$CF_2$—, —$CF_2CF_2$—, —$CF_2CF_2CF_2$— or $CH_2CF_2CF_2$— is preferable, —$CF_2$—, —$CF_2CF_2$— or —$CF_2CF_2CF_2$— is more preferable, and —$CF_2$— is particularly desirable.

The alkylene group or fluorinated alkylene group may have a substituent. The expression that the alkylene group or fluorinated alkylene group "may have a substituent" means that part or all of the hydrogen atoms or fluorine atoms in the alkylene group or fluorinated alkylene group may each be substituted, either with an atom other than a hydrogen atom or fluorine atom, or with a group.

Examples of substituents which the alkylene group or fluorinated alkylene group may have include an alkyl group of 1 to 4 carbon atoms, an alkoxy group of 1 to 4 carbon atoms, and a hydroxyl group.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate, such as methanesulfonate, n-propanesulfonate, n-butanesulfonate, n-octanesulfonate, 1-adamantanesulfonate, 2-norbornanesulfonate or d-camphor-10-sulfonate; or replaced by an aromatic sulfonate, such as benzenesulfonate, perfluorobenzenesulfonate or p-toluenesulfonate.

Furthermore, onium salts in which the anion moiety of these onium salts has been replaced by an anion moiety represented by any one of formulas (b1) to (b8) shown below can also be used.

[Chemical Formula 66]

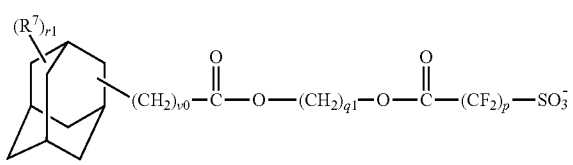

(b1)

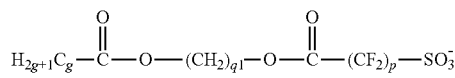

(b2)

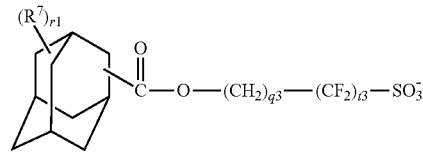

(b3)

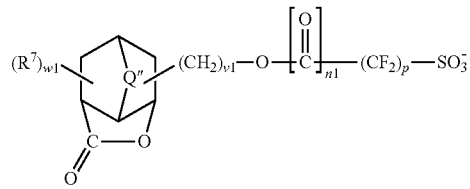

(b4)

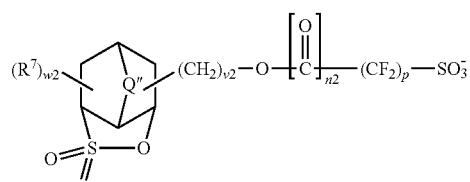

(b5)

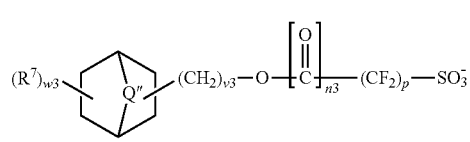

(b6)

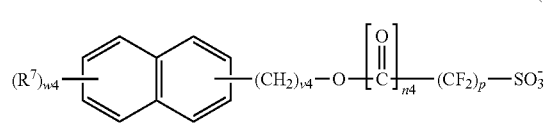

(b7)

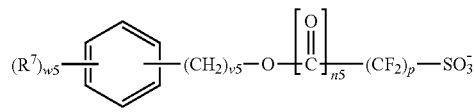

(b8)

In the formulas, p represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n5 independently represents 0 or 1; each of v0 to v5 independently represents an integer of 0 to 3; each of w1 to w5 independently represents an integer of 0 to 3; and Q'' is the same as defined above.

As the substituent for $R^7$, the same groups as those which the aforementioned aliphatic hydrocarbon group or aromatic hydrocarbon group for X may have as a substituent can be used.

If there are two or more of the $R^7$ group, as indicated by the values r1, r2, and w1 to w5, then the two or more of the $R^7$ groups may be the same or different from each other.

Further, onium salt-based acid generators in which the anion moiety in general formula (b-1) or (b-2) is replaced by an anion moiety represented by general formula (b-3) or (b-4) shown below (the cation moiety is the same as (b-1) or (b-2)) may be used.

[Chemical Formula 67]

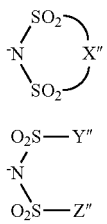

(b-3)

(b-4)

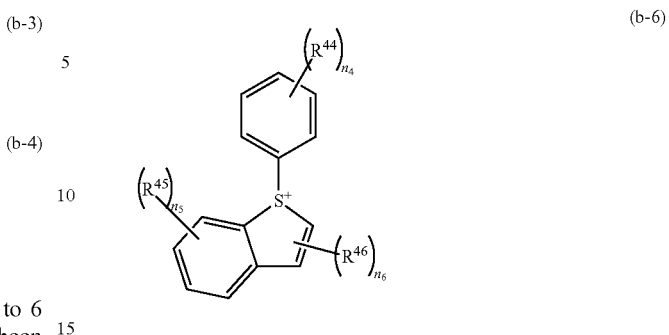

(b-6)

In the formulas, X" represents an alkylene group of 2 to 6 carbon atoms in which at least one hydrogen atom has been substituted with a fluorine atom, and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and more preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible, because the acid strength increases and the transparency to high energy radiation of 200 nm or less and electron beams is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (b-5) or (b-6) shown below may also be used.

[Chemical Formula 68]

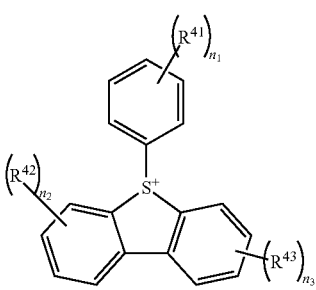

(b-5)

In the formulas, each of $R^{41}$ to $R^{46}$ independently represents an alkyl group, an acetyl group, an alkoxy group, a carboxy group, a hydroxyl group or a hydroxyalkyl group; each of n1 to n5 independently represents an integer of 0 to 3; and n6 represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of n1 to n6, then the two or more of the individual $R^{41}$ to $R^{46}$ group may be the same or different from each other.

n1 is preferably 0 to 2, more preferably 0 or 1, and still more preferably 0.

It is preferable that each of n2 and n3 independently represents 0 or 1, and more preferably 0.

n4 is preferably 0 to 2, and more preferably 0 or 1.

n5 is preferably 0 or 1, and more preferably 0.

n6 is preferably 0 or 1, and more preferably 1.

The anion moiety of the sulfonium salt having a cation moiety represented by general formula (b-5) or (b-6) is not particularly limited, and the same anion moieties for onium salt-based acid generators which have been proposed may be used. Examples of such anion moieties include fluorinated alkylsulfonic acid ions such as anion moieties ($R^{4"}SO_3^-$) for onium salt-based acid generators represented by general formula (b-1) or (b-2) shown above; and anion moieties represented by general formula (b-3) or (b-4) shown above.

In the present description, an oxime sulfonate-based acid generator is a compound having at least one group represented by general formula (B-1) shown below, and has a feature of generating acid by irradiation. Such oxime sulfonate-based acid generators are widely used for a chemically amplified resist composition, and can be appropriately selected.

[Chemical Formula 69]

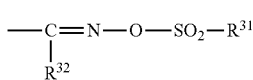

(B-1)

In the formula, each of $R^{31}$ and $R^{32}$ independently represents an organic group.

The organic group for $R^{31}$ and $R^{32}$ refers to a group containing a carbon atom, and may also include atoms other than the carbon atom (such as a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or an aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression that the alkyl group or aryl group "may have a substituent" means that some or all of the hydrogen atoms of the alkyl group or aryl group may be substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 70]

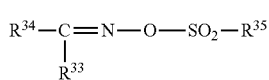

(B-2)

In the formula, $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 71]

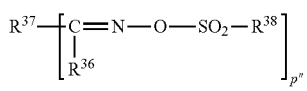

(B-3)

In the formula, $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms have been substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 86) may be preferably used.

Furthermore, as preferable examples, the following can be used.

[Chemical Formula 72]

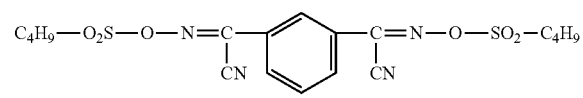

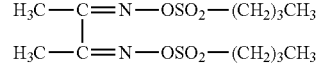

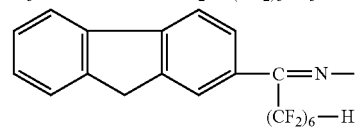

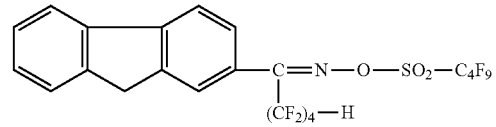

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may also be used favorably.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (B), one type of acid generator may be used alone, or two or more types of acid generators may be used in combination. When using two or more types of acid generators in combination, it is preferable to use an acid generator having an anion moiety represented by any one of the aforementioned formulas (b1) to (b8) in combination with an acid generator containing an alkyl sulfonate such as d-camphor-10-sulfonate.

In the resist composition 1 of the present invention, as the component (B), it is preferable to use an onium salt-based acid generator having a fluorinated alkylsulfonic acid ion as the anion moiety, or an onium salt-based acid generator having an alkyl sulfonate such as d-camphor-10-sulfonate as the anion moiety.

In the positive resist composition of the present invention, the amount of the component (B) relative to 100 parts by weight of the component (A') is preferably 0.5 to 50 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Component—Component (D)>

It is preferable that the resist composition 1 of the present invention further includes a nitrogen-containing organic compound (D) (hereafter referred to as the component (D)) as an optional component.

As the component (D), there is no particular limitation as long as it functions as an acid diffusion control agent, i.e., a quencher which traps the acid generated from the component (A') upon exposure. A multitude of these components (D) have already been proposed, and any of these known compounds may be used. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (that is, alkylamines or alkyl alcohol amines), and cyclic amines.

Specific examples of alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are more preferable, and tri-n-pentylamine or tri-n-octylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonyl pyrrolidine.

As the component (D), one type of compound may be used alone, or two or more types may be used in combination.

The component (D) is typically used in an amount within a range from 0.01 to 5.0 parts by weight, relative to 100 parts by weight of the component (A'). When the amount of the component (D) is within the above-mentioned range, the shape of the resist pattern and the post exposure stability of the latent image formed by the pattern-wise exposure of the resist layer are improved.

<Component (E)>

Furthermore, in the resist composition 1, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids include phosphoric acid, phosphonic acid and phosphinic acid, and among these, phosphonic acid is particularly desirable.

Examples of the phosphorus oxo acid derivatives include esters in which a hydrogen atom within an aforementioned oxo acid is substituted with a hydrocarbon group. Examples of the hydrocarbon group include alkyl groups of 1 to 5 carbon atoms and aryl groups of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one compound may be used alone, or two or more different compounds may be used in combination.

As the component (E), an organic carboxylic acid is preferred, and salicylic acid is particularly desirable.

The component (E) is typically used in an amount within a range from 0.01 to 5.0 parts by weight, relative to 100 parts by weight of the component (A').

<Component (F)>

The resist composition may further include a fluorine additive (hereafter, referred to as "component (F)") for imparting water repellency to the resist film. As the component (F), for example, a fluorine-containing polymeric compound described in Japanese Unexamined Patent Application, First Publication No. 2010-002870 can be used.

Specific examples of the component (F) include polymers having a structural unit represented by formula (f1-1) shown below. The component (F) is preferably a polymer (homopolymer) consisting of a structural unit represented by formula (f1-1) shown below; a copolymer of a structural unit represented by formula (f1-1) shown below and the aforementioned structural unit (a1); or a copolymer of a structural unit represented by formula (f1-1) shown below, a structural unit derived from acrylic acid or methacrylic acid and the aforementioned structural unit (a1). As the structural unit (a1) to be copolymerized with a structural unit represented by formula (f1-1) shown below, a structural unit represented by the aforementioned formula (a1-1-32) is preferable.

[Chemical Formula 73]

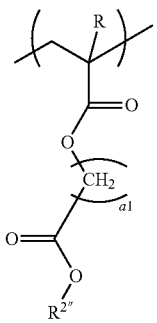

(f1-1)

In the formula, R is the same as defined above; a1 represents an integer of 1 to 5; and $R^{2''}$ represents an organic group containing a fluorine atom.

In formula (f1-1), $R^{2''}$ represents an organic group containing a fluorine atom, and is preferably a hydrocarbon group containing a fluorine atom. Examples of the hydrocarbon group containing a fluorine atom include groups in which part or all of the hydrogen atoms within a linear or branched alkyl group (preferably a linear alkyl group) has been substituted with a fluorine atom.

Among these, as $R^{2''}$, a group represented by the formula "—$(CH_2)_o$—$CF_3$" is preferable (in the formula, o represents an integer of 1 to 3).

In formula (f1-1), a1 represents an integer of 1 to 5, preferably an integer of 1 to 3, and more preferably 1 or 2.

In formula (f1-1), R is the same as defined above. As R, a hydrogen atom or a methyl group is preferable.

As the component (F), one type may be used alone, or two or more types may be used in combination.

The component (F) is typically used in an amount within a range from 0.1 to 10 parts by weight, relative to 100 parts by weight of the component (A').

If desired, other miscible additives can also be added to the resist composition. Examples of such miscible additives include additive resins for improving the performance of the resist film, surfactants for improving the applicability, dissolution inhibitors, plasticizers, stabilizers, colorants, halation prevention agents, and dyes.

<Component (S)>

The resist composition 1 can be prepared by dissolving the components to be added to the resist composition in an organic solvent (hereafter, referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples of the component (S) include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

The component (S) can be used individually, or as a mixed solvent containing two or more different solvents.

Among these, γ-butyrolactone, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range from 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably from 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of PGMEA and cyclohexanone is also preferable. The mixing ratio of such a mixed solvent is preferably PGMEA:cyclohexanone=95:5 to 10:90.

The resist composition according to the third aspect of the present invention described above (i.e., the resist composition 1) exhibits excellent lithography properties (such as resolution, LWR and EL margin) and resist pattern shape.

The reason why these effects can be achieved has not been elucidated yet, but it is presumed as follows. In the resist composition 1, because the structural unit (a0) which generates acid upon exposure is included within the component (A') serving as a base material, the structural unit (a0) is uniformly distributed in the resist film together with the component (A'). Further, in the exposed portions, because acid is generated uniformly from the structural unit (a0), the acid decomposable group within the component (A') in the exposed portions is cleaved uniformly.

<<Acid Generator>>

The acid generator (B1) according to the fourth aspect of the present invention includes the aforementioned compound according to the first aspect in which $M^+$ represents an organic cation. The description for the acid generator according to the fourth aspect of the present invention is the same as the description provided for the aforementioned compound according to the first aspect in which $M^+$ represents an organic cation.

The acid generator (B1) according to the fourth aspect of the present invention can be used favorably as an acid generator for a resist composition.

<<Resist Composition 2>>

The resist composition according to the fifth aspect of the present invention (hereafter, sometimes referred to as "resist composition 2") contains a base component (A) which exhibits changed solubility in a developing solution under the action of acid (hereafter, referred to as "component (A)") and an acid generator component (B) which generates acid upon exposure (hereafter, referred to as "component (B)"), wherein the acid generator component (B) contains an acid generator (B1) according to the aforementioned fourth aspect, i.e., an acid generator (B1) including the aforementioned compound according to the first aspect in which $M^+$ represents an organic cation.

<Component (A)>

As the component (A), an organic compound typically used as a base component for a chemically amplified resist composition can be used alone, or two or more of such organic compounds can be mixed together.

When the resist composition 2 of the present invention is a "negative resist composition for alkali developing process" which forms a negative pattern in an alkali developing process, for example, as the component (A), a base component that is soluble in an alkali developing solution is used, and a cross-linker component is further blended in the negative resist composition.

In the negative resist composition for alkali developing process, when acid is generated from the component (B) upon exposure, the action of this acid causes cross-linking between the base component and the cross-linker component, and the cross-linked portion becomes substantially insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition for alkali developing process, a resin that is soluble in an alkali developing solution (hereafter, referred to as "alkali-soluble resin") is used.

Examples of the alkali-soluble resin include a resin having a structural unit derived from at least one of an α-(hydroxyalkyl)acrylic acid and an alkyl ester of α-(hydroxyalkyl) acrylic acid (preferably an alkyl ester having 1 to 5 carbon atoms), as disclosed in Japanese Unexamined Patent Application, First Publication No. 2000-206694; an acrylic resin or polycycloolefin resin having a sulfonamide group, and in which an atom other than a hydrogen atom or a substituent may be bonded to the carbon atom on the α-position, as disclosed in U.S. Pat. No. 6,949,325; an acrylic resin containing a fluorinated alcohol, and in which an atom other than a hydrogen atom or a substituent may be bonded to the carbon atom on the α-position, as disclosed in U.S. Pat. No. 6,949,325, Japanese Unexamined Patent Application, First Publication No. 2005-336452 or Japanese Unexamined Patent Application, First Publication No. 2006-317803; and a polycycloolefin resin having a fluorinated alcohol, as disclosed in Japanese Unexamined Patent Application, First Publication No. 2006-259582. These resins are preferable in that a resist pattern can be formed with minimal swelling.

The term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (and preferably a hydroxyalkyl group of 1 to 5 carbon atoms) is bonded to the carbon atom on the α-position.

As the cross-linker component, typically, an amino-based cross-linker, such as a glycoluril having a methylol group or alkoxymethyl group; or a melamine-based cross-linker is preferable, as it enables formation of a favorable resist pattern with minimal swelling. The amount of the cross-linker component added is preferably within the range from 1 to 50 parts by weight, relative to 100 parts by weight of the alkali-soluble resin.

In the case where the resist composition 2 of the present invention is a resist composition which forms a positive pattern in an alkali developing process and a negative pattern in a solvent developing process, it is preferable to use a base component (A0) (hereafter, referred to as "component (A0)") which exhibits increased polarity by the action of acid. By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the component (B) upon exposure, the action of this acid causes an increase in the polarity of the base component, thereby increasing the solubility of the component (A0) in an alkali developing solution. Therefore, in the formation of a resist pattern, by conducting selective exposure of a resist film formed by applying the resist composition onto a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, in the case of applying a solvent developing process, the component (A0) exhibits high solubility in an organic developing solution prior to exposure, and when acid is generated from the component (B) upon exposure, the polarity of the component (A0) is increased by the action of the generated acid, thereby decreasing the solubility of the component (A0) in an organic developing solution. Therefore, in the formation of a resist pattern, by conducting selective exposure of a resist film formed by applying the resist composition onto a substrate, the exposed portions changes from a soluble state to an insoluble state in an organic developing solution, whereas the unexposed portions remain soluble in an organic developing solution. As a result, by conducting development using an organic developing solution, a contrast can be made between the exposed portions and the unexposed portions, thereby enabling the formation of a negative resist pattern.

In the resist composition 2 of the present invention, the component (A) is preferably a base component which exhibits increased polarity by the action of acid (namely, the component (A0)). That is, the resist composition 2 of the present invention is preferably a chemically amplified resist composition which becomes a positive type in the case of an alkali developing process, and a negative type in the case of a solvent developing process.

The component (A0) may be a resin component (A1) that exhibits increased polarity under the action of acid (hereafter, frequently referred to as "component (A1)"), a low molecular weight compound component (A2) that exhibits increased polarity under the action of acid (hereafter, frequently referred to as "component (A2)"), or a mixture thereof

[Component (A1)]

As the component (A1), a resin component (base resin) typically used as a base component for a chemically amplified resist composition can be used alone, or two or more of such resin components can be mixed together.

In the present invention, the component (A1) preferably has a structural unit derived from an acrylate ester which may have an atom other than hydrogen or a substituent bonded to the carbon atom on the α position.

In the resist composition 2 of the present invention, it is particularly desirable that the component (A1) has a structural unit (a1) derived from an acrylate ester which may have an atom other than hydrogen or a substituent bonded to the carbon atom on the α position and contains an acid decomposable group which exhibits increased polarity by the action of acid.

Further, the component (A1) preferably includes, in addition to the structural unit (a1), at least one structural unit (a2) selected from the group consisting of a structural unit derived from an acrylate ester containing an —$SO_2$— containing cyclic group and which may have an atom other than hydrogen or a substituent bonded to the carbon atom on the α position and a structural unit derived from an acrylate ester containing a lactone-containing cyclic group and which may have an atom other than hydrogen or a substituent bonded to the carbon atom on the α position.

Furthermore, it is preferable that the component (A1) also include a structural unit (a3) derived from an acrylate ester containing a polar group-containing aliphatic hydrocarbon group and which may have an atom other than hydrogen or a substituent bonded to the carbon atom on the α position, as well as the structural unit (a1), or the structural unit (a1) and the structural unit (a2).

Also, the component (A1) may further include a structural unit (a4) which does not fall under the definition of any of the above-mentioned structural units (a1) to (a3).

The structural units (a1) to (a4) are respectively the same as defined above for the structural units (a1) to (a4) in the resist composition 1 according to the third aspect of the present invention. Further, the component (A1) is the same as defined above for the component (A1'), with the exception that the structural unit (a0) is not included as an essential structural unit.

[Component (A2)]

The component (A2) is the same as defined above for the component (A1') in the resist composition 1 according to the third aspect of the present invention.

<Component (B)>

[Component (B1)]

In the resist composition 2 of the present invention, the component (B) includes the aforementioned acid generator (B1) according to the fourth aspect (hereafter, referred to as "component (B1)").

The component (B1) is the same as defined above in the first and fourth aspects of the present invention.

As the component (B1), one type of acid generator may be used alone, or two or more types may be used in combination.

In the resist composition of the present invention, the amount of the component (B1) within the component (B) is preferably 40% by weight or more, still more preferably 60% by weight or more, and may be even 100% by weight.

When the component (B2) described below is used in combination, the amount of the component (B1) within the component (B) is preferably in the range of 50 to 95% by weight, and more preferably 60 to 85% by weight, based on the total weight of the component (B). As the component (B), it is preferable to use an onium salt-based acid generator having a fluorinated alkylsulfonic acid ion as the anion moiety, or an onium salt-based acid generator having an alkyl sulfonate such as d-camphor-10-sulfonate as the anion moiety.

[Component (B2)]

In the resist composition of the present invention, if desired, the component (B) may further include an acid generator component which cannot be classified as the component (B1) (hereafter, referred to as "component (B2)"), in addition to the component (B1).

The component (B2) is not particularly limited, and examples thereof include the same acid generators as those listed above for the component (B) as an optional component in the resist composition 1 according to the third aspect of the present invention which do not fall under the definition of the component (B1).

As the component (B2), one type of acid generator described above may be used alone, or two or more types of acid generators may be used in combination.

In the resist composition 2 of the present invention, the total amount of the component (B) relative to 100 parts by weight of the component (A) is preferably 1 to 70 parts by weight, more preferably 3 to 60 parts by weight, and most preferably 5 to 50 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

The resist composition 2 of the present invention may contain the component (D), the component (E) and/or the component (F) as optional components, or may be dissolved in the component (S) for production, as in the above-mentioned resist composition 1 according to the third aspect of the present invention. The components (D), (E), (F) and (S) are the same as those defined above in the above-mentioned resist composition 1 according to the third aspect of the present invention.

The resist composition according to the fifth aspect of the present invention described above (i.e., the resist composition 2) exhibits excellent lithography properties, such as resolution, LWR and EL margin, and pattern shape.

The reason why these effects can be achieved has not been elucidated yet, but it is presumed as follows. In the resist composition 2, because of the solubility of the acid generator according to the fourth aspect in the component (S) and favorable interactions thereof with the component (A), uniformity within the resist film can be improved, and the diffusion length of the acid generated upon exposure can be controlled, thereby improving various lithography properties.

<<Method of Forming a Resist Pattern>>

The method of forming a resist pattern according to the sixth aspect of the present invention is a method of forming a resist pattern, including: forming a resist film on a substrate using the aforementioned resist composition according to the third aspect (namely, the resist composition 1) or the aforementioned resist composition according to the fifth aspect (namely, the resist composition 2); conducting exposure of the resist film; and developing the resist film to form a resist pattern.

More specifically, using the resist composition as described above, for example, a resist pattern can be formed by a method as described below.

Firstly, the aforementioned resist composition is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, using an electron beam exposure apparatus or the like, the resist film is selectively exposed to an electron beam (EB) through a desired mask pattern, followed by post exposure bake (PEB) under temperature conditions of 80 to 150° C. for 40 to 120 seconds, preferably 60 to 90 seconds. Subsequently, the resist film is subjected to a developing treatment.

In the case of an alkali developing process, an alkali developing solution such as a 0.1 to 10% by weight aqueous solution of tetramethylammonium hydroxide (TMAH) is used to perform an alkali developing treatment.

Alternatively, in the case of a solvent developing process, an organic solvent is used to perform a developing treatment. This organic solvent may be any organic solvent which can dissolve the component (A) (namely, the component (A) prior to exposure), and can be selected appropriately from amongst the known organic solvents. More specifically, polar solvents such as ketone-based solvents, ester-based solvents, alcohol-based solvents, amide-based solvents or ether-based solvents; and hydrocarbon-based solvents can be used, and among these, ester-based solvents are particularly desirable. As an ester-based solvent, butyl acetate is preferable.

As described above, when the resist composition of the present invention is used as a negative resist composition in a solvent developing process which is particularly desirable in the formation of a contact hole pattern, the shape of the contact hole pattern can be effectively prevented from becoming reverse-tapered. Therefore, the resist composition of the present invention is preferably used in a solvent developing process.

A rinse treatment is preferably performed following the developing treatment. In the case of an alkali developing process, it is preferable to conduct a water rinse using pure water. In the case of a solvent developing process, it is preferable to use a rinse liquid containing the aforementioned organic solvent.

Thereafter, drying is carried out. Further, in some cases, a bake treatment (post bake) may be performed following the above developing treatment. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum, as well as glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) can be used.

The wavelength to be used for exposure is not particularly limited and the exposure can be conducted using radiation such as ArF excimer laser, KrF excimer laser, $F_2$ excimer laser, extreme ultraviolet rays (EUV), vacuum ultraviolet rays (VUV), electron beam (EB), X-rays, and soft X-rays. The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (an immersion medium) that has a larger refractive index than the refractive index of air.

More specifically, in immersion lithography, the region between the resist film formed in the above-described manner and lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point: 102° C.), and one example of a suitable perfluoroalkylamine compound is perfluorotributylamine (boiling point: 174° C.).

As the immersion medium, water is preferable in terms of cost, safety, environmental issues and versatility.

EXAMPLES

As follows is a more detailed description of the present invention based on a series of examples, although the scope of the present invention is in no way limited by these examples.

In the NMR analysis of the present examples, the chemical shift standard for $^1$H-NMR was tetramethylsilane (TMS).

Synthesis Example 1

Synthesis of Compound (O)

Under a nitrogen atmosphere, 10 g of a compound (i) and 100 g of dichloromethane were added to a three-necked flask. Then, 14.74 g of triethylamine was dropwise added thereto. After stirring the resulting mixture for 5 minutes, 8.25 g of thionyl chloride was dropwise added thereto. Thereafter, the resulting mixture was stirred for 2 hours, and a solution composed of 9.50 g of a compound (ii) and 9.50 g of dichloromethane was then added thereto. After stirring the resulting mixture for 14 hours at room temperature, the resultant was washed with 100 g of a 1% HCl solution, and dried. The resulting mixture was then purified by silica gel column chromatography to yield 8.33 g of a compound (iii).

5 g of the compound (iii) obtained by the above reaction was dissolved in 15 g of methanol, and a solution containing 0.83 g of NaOH and 50 g of water was then added thereto. After stirring the resulting mixture for 2 hours, 4.17 g of 20% HCl was then added thereto. 50 g of dichloromethane was added to the resulting solution, and after stirring the resulting mixture for 10 minutes, the organic solvent layer was recovered. Thereafter, washing was repeated four times with 50 g of water. 500 g of hexane was added dropwise to the organic layer, followed by filtration to obtain a powder, and the resulting powder was dried, thereby yielding 3.76 g of a compound (iv).

3 g of the compound (iv) obtained by the above reaction was dissolved in 30 g of dichloromethane, and 2.68 g of a compound (v) was then added thereto. 3.2 g of diisopropyl carbodiimide was then added to the resulting suspension. The reaction was allowed to proceed at room temperature for 26 hours, followed by filtration of the reaction liquid. The obtained powder was then washed with methyl ethyl ketone and dried to yield 6.25 g of a mixture containing a compound (O). In the formula shown below, M$^+$ represents Nat

[Chemical Formula 74]

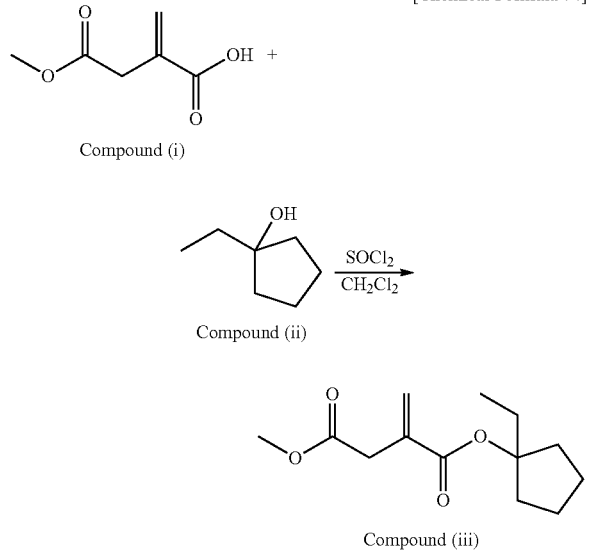

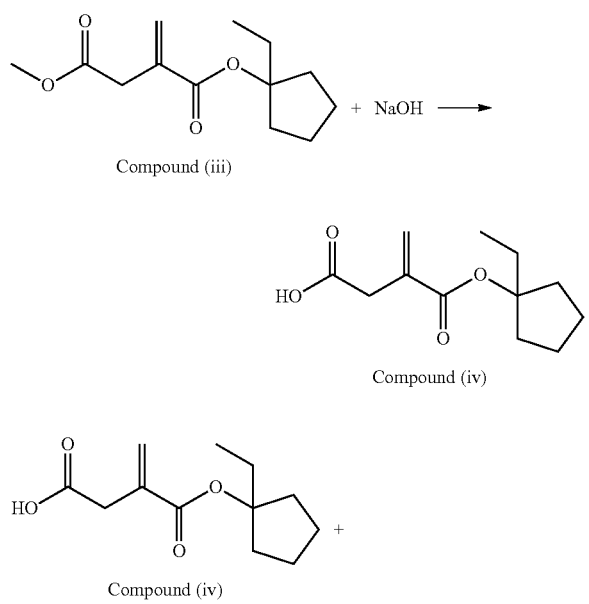

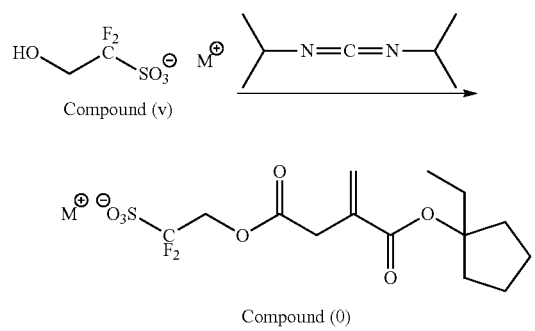

Synthesis Example 2

Synthesis of Compound (1)

3 g of triphenylsulfonium bromide, 15 g of dichloromethane and 15 g of pure water were added to a recovery flask. Then, 3.77 g of the compound (0) obtained in the above-mentioned Synthesis Example 1 was added thereto, and the resulting mixture was stirred for 2 hours. Subsequently, the dichloromethane layer was washed with 1% by weight aqueous solution of hydrochloric acid, and was then washed repeatedly with pure water (20.0 g) until the resultant was neutralized. The organic layer was then concentrated under reduced pressure, thereby yielding 0.47 g of a compound (1) in the form of a white solid. The obtained compound (1) was analyzed by NMR, and the structure was identified on the basis of the results shown below.

$^1$H-NMR (400 MHz, DMSO-d6): δ (ppm)=7.74-7.90 (m, 15H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl)

From the results of the above analysis, it was confirmed that the obtained compound (1) had a structure shown below.

[Chemical Formula 75]

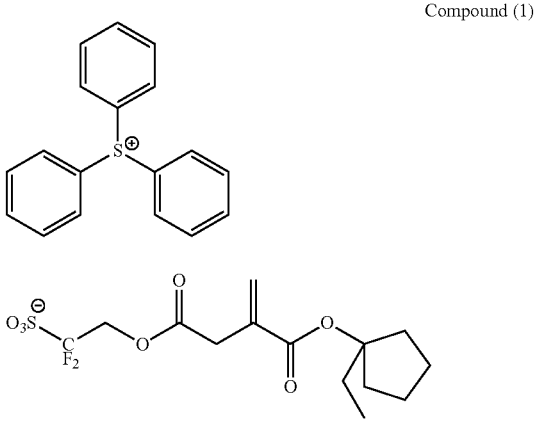

Synthesis Examples 3 to 102

Synthesis of Compounds 2 to 101

The same operations as described above in the Synthesis Example 2 were carried out, with the exception that the compound (0) was changed to anions (in an equimolar amount) indicated in Tables 1 to 26 shown below which were synthesized in the same manner as described above in the Synthesis Example 1, and the cation was changed to cations (in an equimolar amount) indicated in Tables 1 to 26 shown below. As a result, compounds 2 to 101 shown in Tables 1 to 26 were obtained. The symbol "↑" in the tables indicates that the same cation or anion shown above was used.

Each of the obtained compounds was analyzed by NMR. The results were also shown in Tables 1 to 26.

TABLE 1

| Compound | NMR | Cation |
|---|---|---|
| 2 | 7.74-7.90 (m, 15H, ArH), 6.69 (s, 1H, CH), 5.45 (s, 1H, CH), 4.97-5.04 (t, 2H, CH2), 3.36 (s, 2H, CH2), 0.91-2.20 (m, 15H, isopropyl cyclopentyl) | 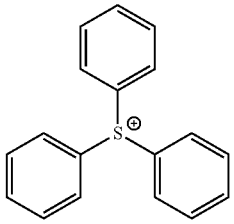 [SMILES: c1ccc([S+](c2ccccc2)c2ccccc2)cc1] |
| 3 | 7.74-7.90 (m, 15H, ArH), 6.71 (s, 1H, CH), 5.76 (s, 1H, CH), 4.80-4.87 (t, 2H, CH2), 3.44 (s, 2H, CH2), 1.36-2.05 (m, 17H, Methyl adamantan) | ↑ |
| 4 | 6.72 (s, 1H, CH), 5.76 (s, 1H, CH), 4.80-4.87 (t, 2H, CH2), 3.43 (s, 2H, CH2), 1.05-2.16 (m, 21H, isopropyl Adamantan) | ↑ |
| 5 | 7.74-7.90 (m, 15H, ArH), 6.74 (s, 1H, CH), 5.50 (s, 1H, CH), 4.97-5.04 (t, 2H, CH2), 4.49 (s, 2H, CH2), 3.40 (s, 2H, CH2), 1.59-2.21 (m, 17H, Adamantan) | ↑ |

| Compound | Anion | Product |
|---|---|---|
| 2 | 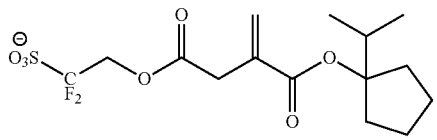 | 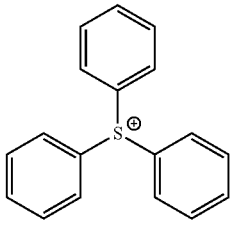 |
| 3 | 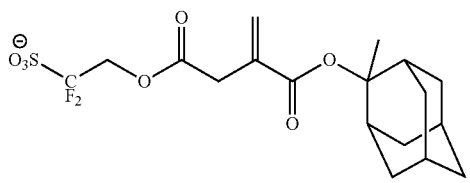 | 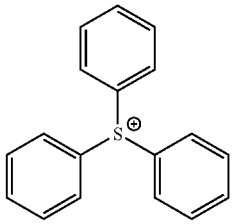 [SMILES: c1ccc([S+](c2ccccc2)c2ccccc2)cc1] |

TABLE 1-continued
| | | |
|---|---|---|
| 4 | 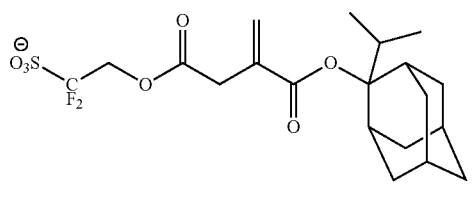 | 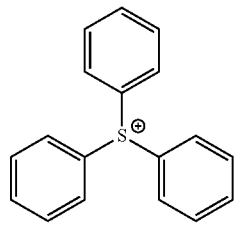 [SMILES: c1ccc([S+](c2ccccc2)c2ccccc2)cc1] |
| | | 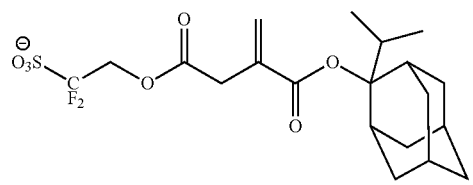 |
| 5 | 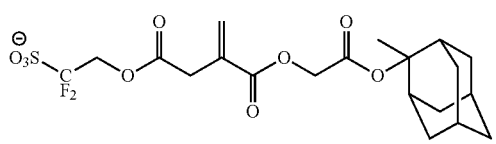 | 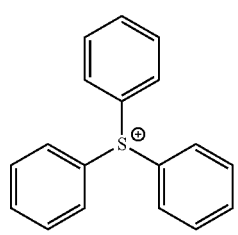 [SMILES: c1ccc([S+](c2ccccc2)c2ccccc2)cc1] |
| | | 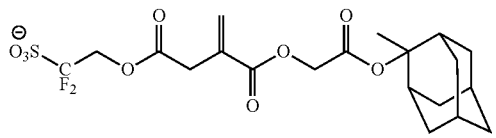 |
TABLE 2
| Compound | NMR | Cation |
|---|---|---|
| 6 | 7.74-7.90 (m, 15H, ArH), 6.74 (s, 1H, CH), 5.81 (s, 2H, CH2), 5.53 (s, 1H, CH), 4.97-5.04 (t, 2H, CH2), 3.48 (m, 1H, CH), 3.38 (s, 2H, CH2), 1.00-2.81 (m, 10H, Cyclohexyl) | 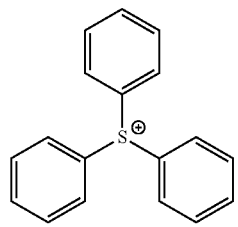 [SMILES: c1ccc([S+](c2ccccc2)c2ccccc2)cc1] |
| 7 | 7.74-7.90 (m, 15H, ArH), 6.72 (s, 1H, CH), 5.86 (m, 1H, CH), 5.52 (s, 1H, CH), 4.97-5.07 (m, 2H, CH2), 3.56 (m, 1H, CH), 3.38 (s, 2H, CH2), 1.00-1.88 (m, 13H, Cyclohexyl + CH3) | ↑ |
| 8 | 7.74-7.90 (m, 15H, ArH), 6.74 (s, 1H, CH), 5.72 (s, 2H, CH2), 5.53 (s, 1H, CH), 4.97-5.04 (t, 2H, CH2), 3.32-3.38 (m, 3H, CH2 + CH), 1.62-2.30 (m, 14H, Adamantyl) | ↑ |
| 9 | 7.74-7.90 (m, 15H, ArH), 6.72 (s, 1H, CH), 5.79 (m, 1H, CH2), 5.52 (s, 1H, CH), 4.97-5.04 (m, 2H, CH2), 3.32-3.38 (m, 3H, CH2 + CH), 1.73-2.30 (m, 14H, Adamantyl), 1.13 (d, 3H, CH3) | ↑ |

TABLE 2-continued
| Compound | Anion | Product |
|---|---|---|
| 6 | 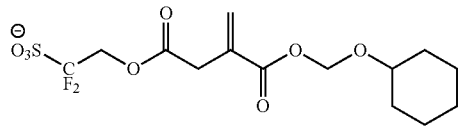 | 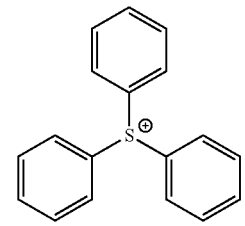 [SMILES: c1ccc([S+](c2ccccc2)c2ccccc2)cc1] |
| 7 | 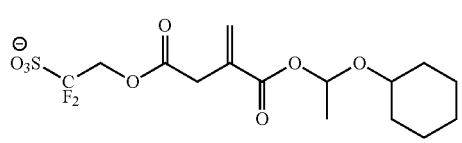 | 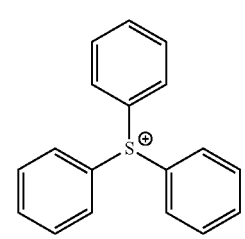 [SMILES: c1ccc([S+](c2ccccc2)c2ccccc2)cc1] |
| 8 | 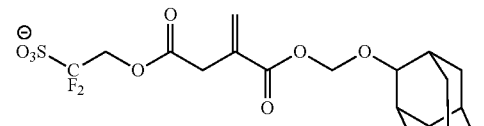 | 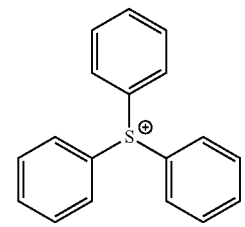 [SMILES: c1ccc([S+](c2ccccc2)c2ccccc2)cc1] |
| 9 | 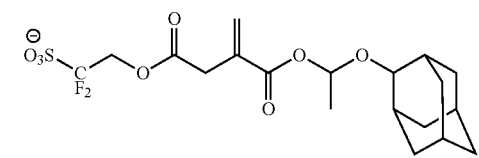 | 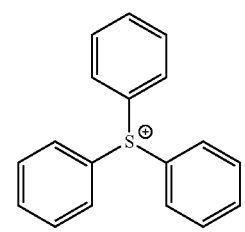 [SMILES: c1ccc([S+](c2ccccc2)c2ccccc2)cc1] |

TABLE 3
| Compound | NMR | Cation |
|---|---|---|
| 10 | 7.74-7.90 (m, 15H, ArH), 6.78 (s, 1H, CH), 5.50 (s, 1H, CH), 5.35 (s, 1H, CH), 5.23 (s, 1H, CH), 4.97-5.04 (t, 2H, CH2), 4.57 (s, 1H, CH), 4.27 (s, 1H, CH), 3.42 (s, 2H, CH2), 2.79 (s, 1H, CH), 1.75-1.91 (m, 2H, CH, CH) | 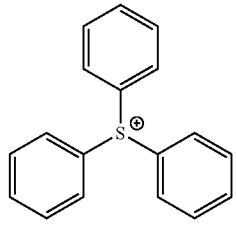 |
| 11 | 7.74-7.90 (m, 15H, ArH), 6.74 (s, 1H, CH), 5.51 (s, 1H, CH), 4.97-5.04 (m, 3H, CH2 + CH), 4.83 (s, 1H, CH), 3.38 (s, 2H, CH2), 3.27 (s, 1H, CH), 1.44-2.66 (m, 6H, CH + CH + CH2 + CH2) | ↑ |
| 12 | 7.74-7.90 (m, 15H, ArH), 6.74 (s, 1H, CH), 5.51 (s, 1H, CH), 4.91-5.19 (m, 4H, CH2 + CH2), 4.08 (s, 1H, CH), 3.41 (s, 2H, CH2), 1.53-3.31 (m, 6H, CH + CH2) | ↑ |
| 13 | 7.74-7.90 (m, 15H, ArH), 6.78 (s, 1H, CH), 5.50 (s, 1H, CH), 5.41-5.47 (m, 4H, CH + CH), 4.97-5.04 (m, 3H, CH2 + CH), 4.80 (m, 2H, CH2), 4.09 (m, 1H, CH), 2.46-3.42 (m, 4H, CH2 + CH + CH) | ↑ |
| Compound | Anion | Product |
|---|---|---|
| 10 | 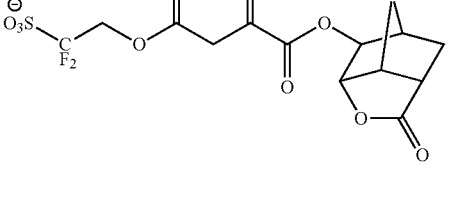 | 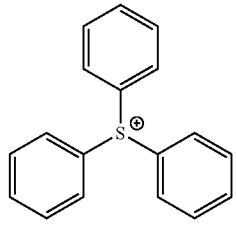 |
| 11 | 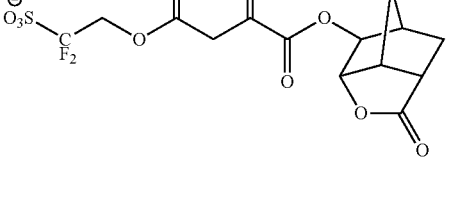 | 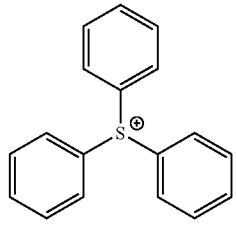 |

TABLE 3-continued
| 12 | 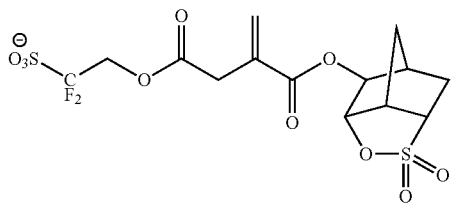 | 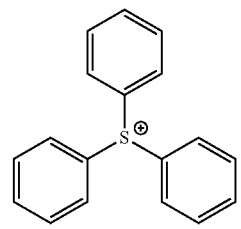 [SMILES: c1ccc([S+](c2ccccc2)c2ccccc2)cc1] |
|---|---|---|
| | 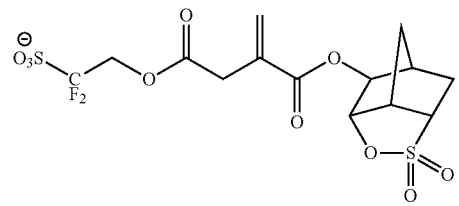 | |
| 13 | 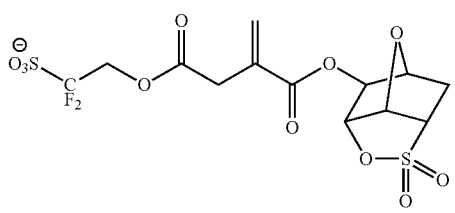 | 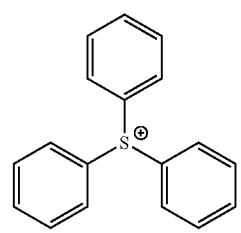 |
| | 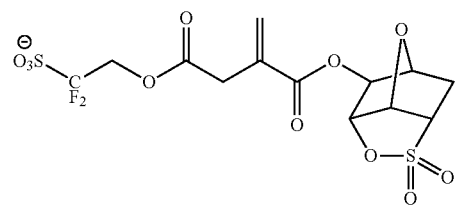 | |
TABLE 4
| Compound | NMR | Cation |
|---|---|---|
| 14 | 7.74-7.90 (m, 15H, ArH), 6.81 (s, 1H, CH), 5.97 (s, 1H, CH), 5.58 (s, 1H, CH), 4.97-5.04 (t, 2H, CH2), 4.24-4.48 (m, 2H, CH + CH), 3.38 (s, 2H, CH2), 2.51-2.93 (m, 2H, CH + CH) | 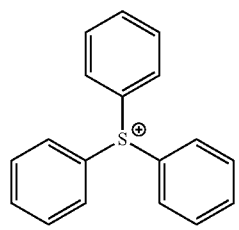 [SMILES: c1ccc([S+](c2ccccc2)c2ccccc2)cc1] |
| 15 | 7.74-7.90 (m, 15H, ArH), 6.74 (s, 1H, CH), 5.50 (s, 1H, CH), 5.17 (s, 1H, CH), 4.97-5.04 (t, 2H, CH2), 4.74 (s, 1H, CH), 4.39 (s, 1H, CH), 3.96 (s, 1H, CH), 1.56-3.40 (m, 9H, Sulton + CH2) | ↑ |
| 16 | 7.74-7.90 (m, 15H, ArH), 6.74-6.75 (s, 1H, CH), 5.45 (s, 1H, CH), 4.97-5.04 (t, 2H, CH2), 4.34 (s, 1H, OH), 3.35 (s, 2H, CH2), 1.71-2.88 (m, 14H, Adamantan) | ↑ |
| 17 | 7.74-7.90 (m, 15H, ArH), 6.74 (s, 1H, CH), 6.16 (m, 1H, OH), 5.53 (s, 1H, CH), 4.93-5.10 (m, 2H, CH2), 4.59-4.61 (m, 2H, CH2), 3.91-3.97 (m, 2H, CH2), 3.39 (s, 2H, CH2) | ↑ |

TABLE 4-continued

| Compound | Anion | Product |
|---|---|---|
| 14 | [structure: ⁻O₃S-CF₂-CH₂-O-C(O)-CH₂-C(=CH₂)-C(O)-O-(γ-butyrolactone)] | [triphenylsulfonium cation with anion structure below] |
| 15 | [structure: ⁻O₃S-CF₂-CH₂-O-C(O)-CH₂-C(=CH₂)-C(O)-O-CH₂-C(O)-O-(sultone bicyclic)] | [triphenylsulfonium cation with anion structure below] |
| 16 | [structure: ⁻O₃S-CF₂-CH₂-O-C(O)-CH₂-C(=CH₂)-C(O)-O-adamantyl-OH] | [triphenylsulfonium cation with anion structure below] |
| 17 | [structure: ⁻O₃S-CF₂-CH₂-O-C(O)-CH₂-C(=CH₂)-C(O)-O-CH₂CH₂-OH] | [triphenylsulfonium cation with anion structure below] |

TABLE 5
| Compound | NMR | Cation |
|---|---|---|
| 18 | 7.14-7.90 (m, 15H, ArH), 6.59 (s, 1H, CH), 5.47 (s, 1H, CH), 4.17-4.22 (t, 2H, CH2), 3.50-3.54 (t, 2H, CH2), 3.29 (s, 2H, CH2), 0.91-2.34 (m, 13H, Ethylcyclopentyl) | 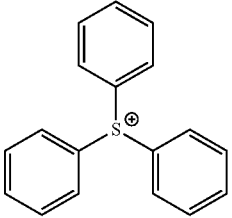 [SMILES: c1ccc([S+](c2ccccc2)c2ccccc2)cc1] |
| 19 | 7.74-7.90 (m, 15H, ArH), 6.64 (s, 1H, CH), 5.79-5.83 (m, 2H, CH2), 5.58 (s, 1H, CH), 4.17-4.22 (t, 2H, CH2), 3.50-3.54 (m, 3H, CH2 + CH), 3.30 (s, 2H, CH2), 1.00-1.81 (m, 10H, cyclohexyl) | .. |
| 20 | 7.74-7.90 (m, 15H, ArH), 6.45 (s, 1H, CH), 5.52 (s, 1H, CH), 3.95-3.99 (m, 2H, CH2), 3.19 (s, 2H, CH2), 1.91-3.04 (m, 17H, Ethylcyclopentyl + CH2 + CH2) | ↑ |
| 21 | 7.74-7.90 (m, 15H, ArH), 6.45 (s, 1H, CH), 5.53 (s, 1H, CH), 4.85 (m, 1H, CH), 3.35 (s, 2H, CH2), 0.91-3.26 (m, 26H, Ethylcyclopentyl + camphor) | ↑ |
| Compound | Anion | Product |
|---|---|---|
| 18 | 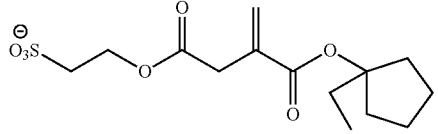 | 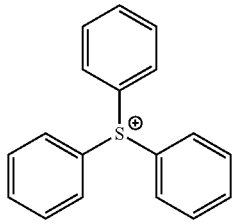 [SMILES: c1ccc([S+](c2ccccc2)c2ccccc2)cc1] |
| 19 | 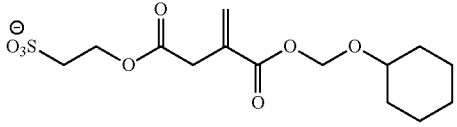 | 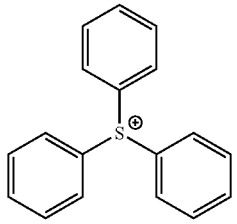 [SMILES: c1ccc([S+](c2ccccc2)c2ccccc2)cc1] |

TABLE 5-continued
| | | |
|---|---|---|
| 20 | 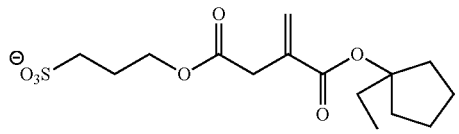 | 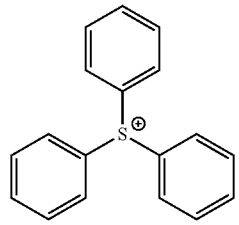 [SMILES: c1ccc([S+](c2ccccc2)c2ccccc2)cc1] 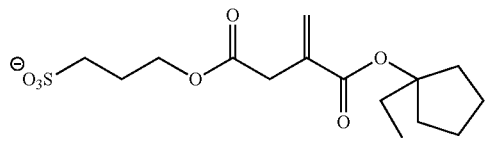 |
| 21 | 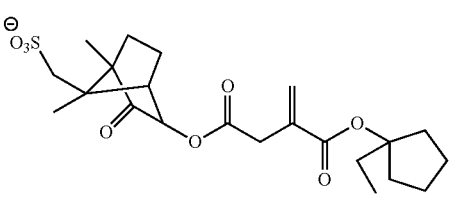 | 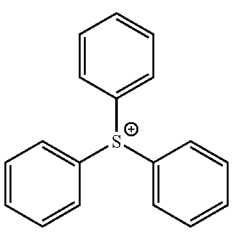 [SMILES: c1ccc([S+](c2ccccc2)c2ccccc2)cc1] 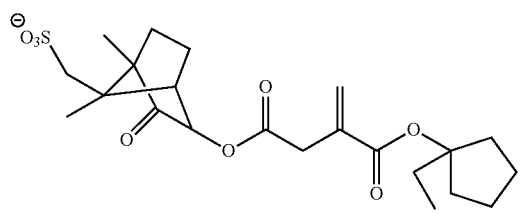 |
TABLE 6
| Compound | NMR | Cation |
|---|---|---|
| 22 | 7.74-7.90 (m, 19H, Phenyl), 6.43 (s, 1H, CH), 5.42 (s, 1H, CH), 4.15-4.18 (t, 2H, CH2), 3.34-3.36 (s, 2H, CH2), 3.23-3.27 (t, 2H, CH2), 0.91-2.38 (m, 13H, Ethylcyclopentyl) | 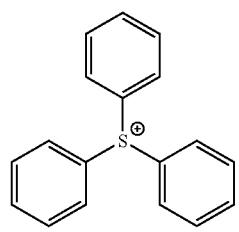 [SMILES: c1ccc([S+](c2ccccc2)c2ccccc2)cc1] |
| 23 | 7.74-7.94 (d, 17H, Phenyl), 7.49-7.51 (d, 2H, Phenyl), 6.61 (s, 1H, CH), 5.62 (s, 1H, CH), 3.69 (s, 2H, CH2), 0.91-2.38 (m, 13H, Ethylcyclopentyl) | ↑ |
| 24 | 7.28-8.62 (m, 21H, Phenyl), 6.61 (s, 1H, CH), 5.62 (s, 1H, CH), 3.76 (s, 2H, CH), 0.93-2.38 (m, 13H, Ethylcyclopentyl) | ↑ |
| 25 | 7.02-8.20 (m, 21H, Phenyl), 6.61 (s, 1H, CH), 5.62 (s, 1H, CH), 3.62 (s, 2H, CH2), 0.91-2.38 (m, 13H, Ethylcyclopentyl) | ↑ |

TABLE 6-continued
| Compound | Anion | Product |
|---|---|---|
| 22 | 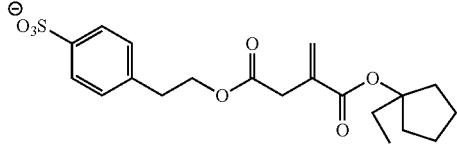 | 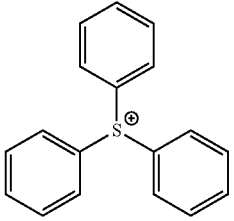 [SMILES: c1ccc([S+](c2ccccc2)c2ccccc2)cc1] |
| 23 | 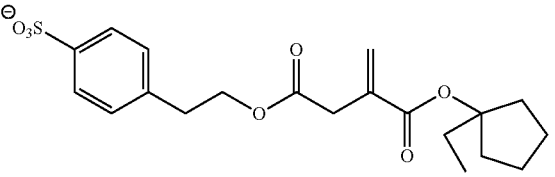 | 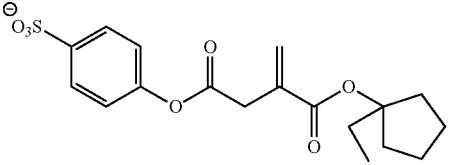 |
| 24 | 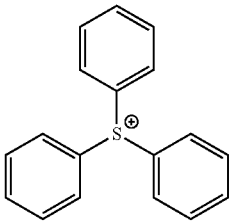 [SMILES: c1ccc([S+](c2ccccc2)c2ccccc2)cc1] | 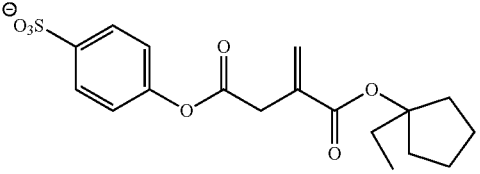 |

TABLE 6-continued
25 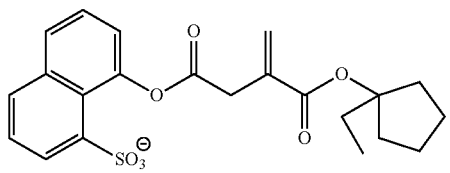 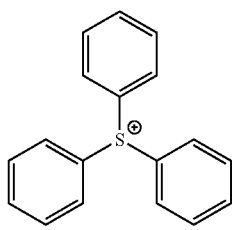 [SMILES: c1ccc([S+](c2ccccc2)c2ccccc2)cc1]
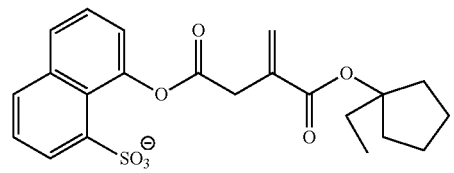
TABLE 7
| Compound | NMR | Cation |
|---|---|---|
| 26 | 7.46-8.43 (m, 21H, Phenyl), 6.61 (s, 1H, CH), 5.62 (s, 1H, CH), 3.73 (s, 2H, CH2), 0.91-2.38 (m, 13H, Ethylcyclopentyl) | 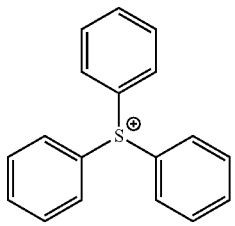 [SMILES: c1ccc([S+](c2ccccc2)c2ccccc2)cc1] |
| 27 | 7.74-8.46 (m, 21H, Phenyl), 6.61 (s, 1H, CH), 5.62 (s, 1H, CH), 3.73 (s, 2H, CH2), 0.91-2.38 (m, 13H, Ethylcyclopentyl) | ↑ |
| 28 | 7.57-8.51 (m, 21H, Phenyl), 6.61 (s, 1H, CH), 5.62 (s, 1H, CH), 3.62 (s, 2H, CH2), 0.91-2.38 (m, 13H, Ethylcyclopentyl) | ↑ |
| 29 | 7.05-8.46 (m, 21H, Phenyl), 6.66 (s, 1H, CH), 5.79-5.81 (m, 2H, CH2), 5.73 (s, 1H, CH), 3.74 (s, 2H, CH2), 1.00-3.48 (m, 11H, cyclohexyl) | ↑ |
| Compound | Anion | Product |
|---|---|---|
| 26 | 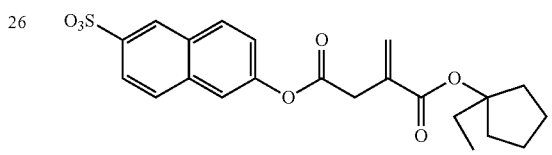 | 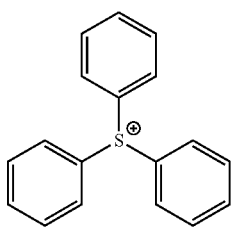 [SMILES: c1ccc([S+](c2ccccc2)c2ccccc2)cc1] |
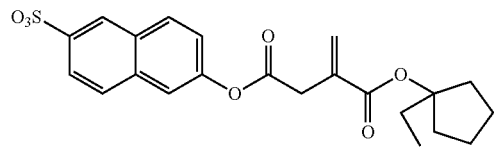

TABLE 7-continued
27 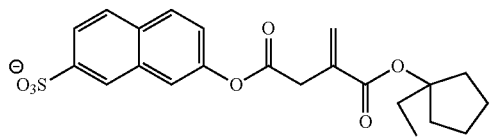 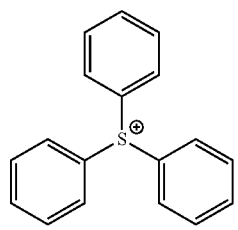 [SMILES: c1ccc([S+](c2ccccc2)c2ccccc2)cc1]
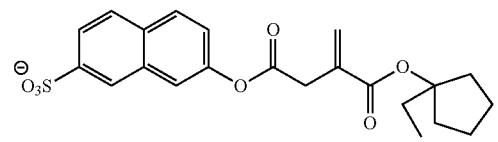
28 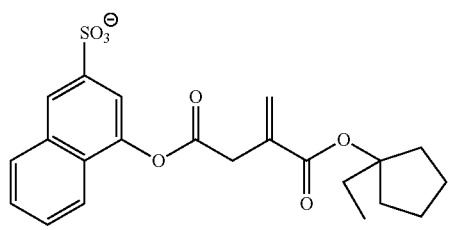 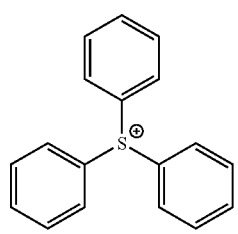 [SMILES: c1ccc([S+](c2ccccc2)c2ccccc2)cc1]
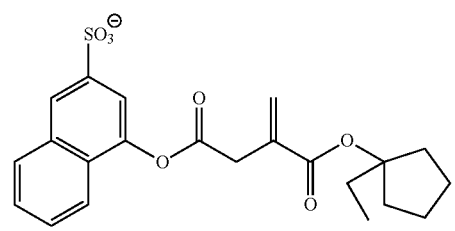
29 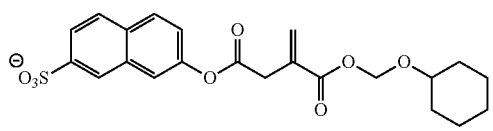 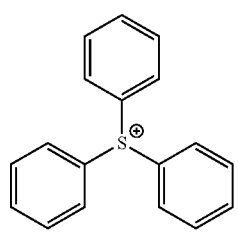 [SMILES: c1ccc([S+](c2ccccc2)c2ccccc2)cc1]
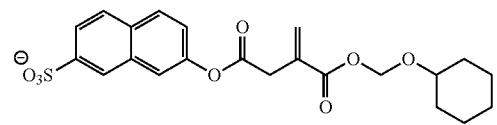

TABLE 8
| Compound | NMR | Cation |
|---|---|---|
| 30 | 7.74-7.90 (m, 15H, ArH), 6.50 (s, 1H, CH), 5.79-5.81 (m, 2H, CH2), 5.63 (s, 1H, CH), 3.97 (s, 2H, CH2), 1.17-3.48 (m, 17H, cyclohexyl + CH2 + CH2 + CH2) | 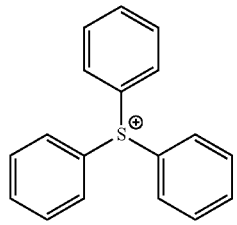 |
| 31 | 7.74-7.90 (m, 15H, ArH), 6.50 (s, 1H, CH), 5.81 (s, 2H, CH2), 5.64 (s, 1H, CH), 4.85 (s, 1H, CH), 0.91-3.48 (m, 26H, Ethylcyclopentyl + camphor) | ↑ |
| 32 | 7.74-7.90 (m, 15H, ArH), 6.61 (s, 1H, CH), 5.62 (s, 1H, CH), 3.67 (s, 2H, CH), 0.91-2.38 (m, 13H, Ethylcyclopentyl) | ↑ |
| 33 | 7.74-7.90 (m, 15H, ArH), 6.66 (s, 1H, CH), 5.81 (m, 2H, CH2), 5.73 (s, 1H, CH), 3.68 (s, 2H, CH2), 3.48 (s, 1H, CH), 0.96-1.81 (m, 10H, cyclohexyl) | ↑ |
| Compound | Anion | Product |
|---|---|---|
| 30 | 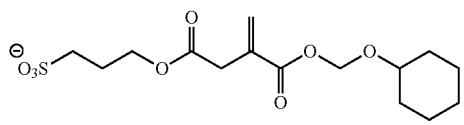 | 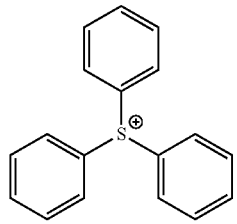 [SMILES: c1ccc([S+](c2ccccc2)c2ccccc2)cc1]<br />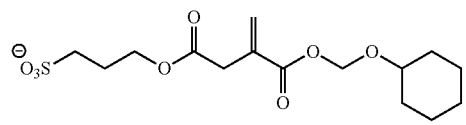 |
| 31 | 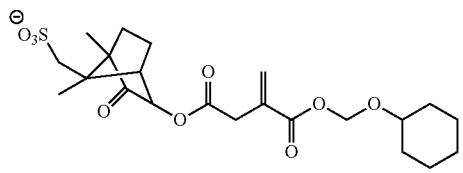 | 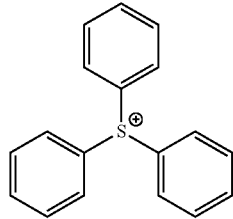<br />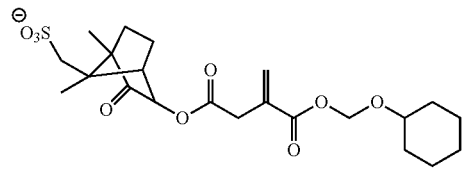 |

TABLE 8-continued
| 32 | 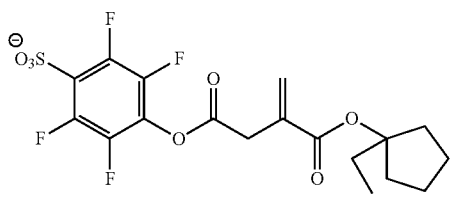 | 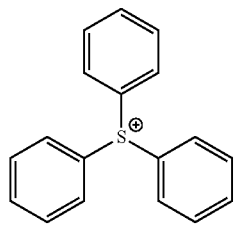 [SMILES: c1ccc([S+](c2ccccc2)c2ccccc2)cc1] |
| --- | --- | --- |
|  | 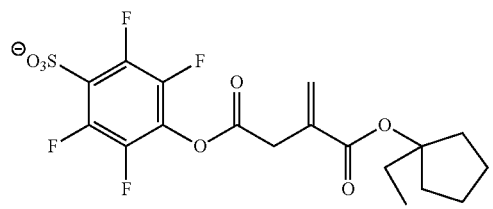 |  |
| 33 | 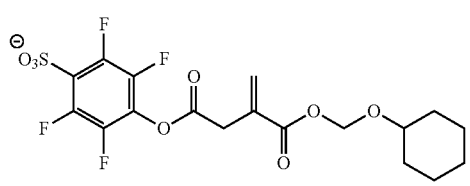 | 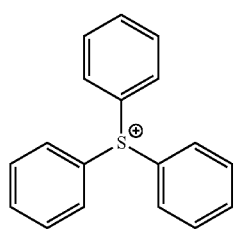 [SMILES: c1ccc([S+](c2ccccc2)c2ccccc2)cc1] |
|  | 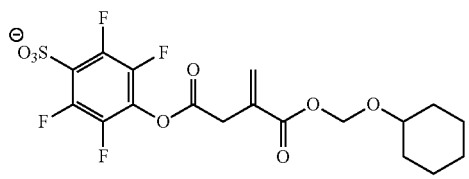 |  |
TABLE 9
| Compound | NMR | Cation |
| --- | --- | --- |
| 34 | 7.74-7.90 (m, 15H, ArH), 6.59 (s, 1H, CH), 5.47 (s, 1H, CH), 4.47-4.49 (m, 2H, CH2), 3.53-3.57 (m, 2H, CH2), 3.28 (s, 2H, CH2), 0.91-2.38 (m, 13H, EthylCyclopentyl) | 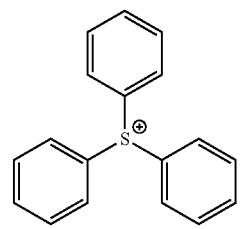 [SMILES: c1ccc([S+](c2ccccc2)c2ccccc2)cc1] |
| 35 | 7.74-7.90 (m, 15H, ArH), 6.47 (s, 1H, CH), 5.47 (s, 1H, CH), 4.24-4.29 (m, 2H, CH2), 3.53-3.57 (m, 2H, CH2), 3.27 (s, 2H, CH2), 0.91-2.38 (m, 13H, EthylCyclopentyl) | ↑ |
| 36 | 7.74-7.90 (m, 15H, ArH), 6.69 (s, 1H, CH), 5.42 (s, 1H, CH), 4.87-4.94 (m, 2H, CH2), 3.39 (s, 2H, CH2), 0.91-2.38 (m, 13H, EthylCyclopentyl) | ↑ |

TABLE 9-continued

| Compound | Anion | Product |
|---|---|---|
| 34 | (structure: F₃C-S(O₂)-N⁻-S(O₂)-CH₂CH₂-O-C(O)-C(=CH₂)-CH₂-C(O)-O-ethylcyclopentyl) | triphenylsulfonium cation; and anion (F₃C-S(O₂)-N⁻-S(O₂)-CH₂CH₂-O-C(O)-C(=CH₂)-CH₂-C(O)-O-ethylcyclopentyl) |
| 35 | (structure: F₃C-S(O₂)-N⁻-CH₂CH₂-O-C(O)-C(=CH₂)-CH₂-C(O)-O-ethylcyclopentyl) | triphenylsulfonium cation; and anion (F₃C-S(O₂)-N⁻-CH₂CH₂-O-C(O)-C(=CH₂)-CH₂-C(O)-O-ethylcyclopentyl) |
| 36 | (structure: F₃C-S(O₂)-N⁻-S(O₂)-CF₂-CH₂-O-C(O)-C(=CH₂)-CH₂-C(O)-O-ethylcyclopentyl) | triphenylsulfonium cation; and anion (F₃C-S(O₂)-N⁻-S(O₂)-CF₂-CH₂-O-C(O)-C(=CH₂)-CH₂-C(O)-O-ethylcyclopentyl) |

TABLE 10

| Compound NMR | Cation |
|---|---|
| 37    7.74-7.90 (m, 15H, ArH), 6.51 (s, 1H, CH), 5.51 (s, 1H, CH), 3.57 (s, 1H, CH), 1.69-2.38 (m, 10H, EthylCyclopentyl), 0.91-0.95 (t, 3H, CH3) | triphenylsulfonium cation |
| 38    7.74-7.90 (m, 15H, ArH), 6.63 (s, 1H, CH), 5.56 (s, 1H, CH), 4.64 (s, 2H, CH2), 3.47 (s, 1H, CH), 1.69-2.38 (m, 10H, EthylCyclopentyl), 0.91-0.95 (t, 3H, CH3) | ↑ |

TABLE 10-continued
| | | |
|---|---|---|
| 39 | 7.74-7.90 (m, 15H, ArH), 6.41 (s, 1H, CH), 5.53 (s, 1H, CH), 3.34 (s, 2H, CH2), 1.65-2.38 (m, 25H, EthylCyclopentyl + Adamantan), 0.91-0.95 (t, 3H, CH3) | ↑ |
| 40 | 7.75-7.86 (m, 10H, ArH), 7.61 (s, 2H, ArH), 6.61 (s, 1H, CH), 5.65 (s, 1H, CH), 4.80-4.87 (t, 2H, CH2), 4.62 (s, 2H, CH2), 3.41 (s, 2H, CH2), 0.90-2.34 (m, 33H, Ethylcyclopentyl + Adamantan + CH3) | 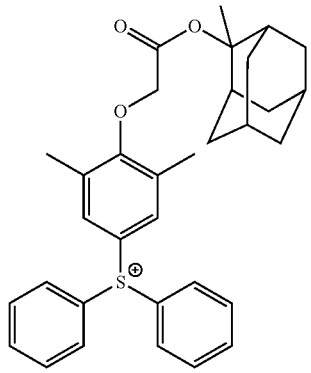 [SMILES: Cc1cc([S+](c2ccccc2)c2ccccc2)cc(C)c1OCC(=O)OC1(C)C2CC3CC(C2)CC1C3] |
| Compound | Anion | Product |
|---|---|---|
| 37 | 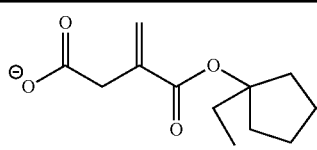 | 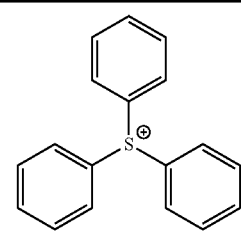<br>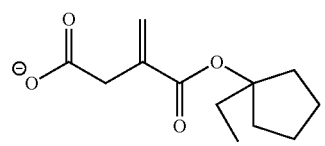 [SMILES: C=C(CC(=O)[O-])C(=O)OC1(CC)CCCC1] |
| 38 | 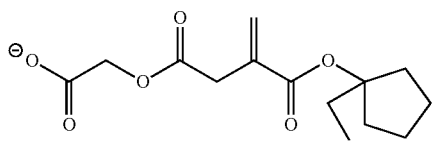 [SMILES: C=C(CC(=O)OCC(=O)[O-])C(=O)OC1(CC)CCCC1] | 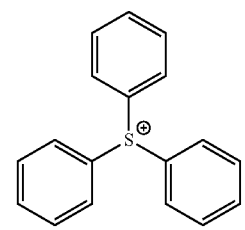 [SMILES: c1ccc([S+](c2ccccc2)c2ccccc2)cc1]<br>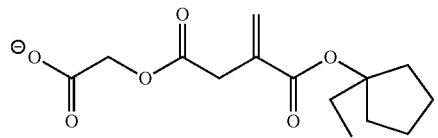 [SMILES: C=C(CC(=O)OCC(=O)[O-])C(=O)OC1(CC)CCCC1] |
| 39 | 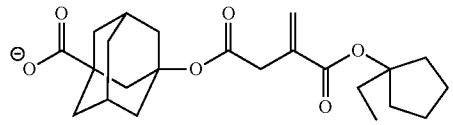 [SMILES: C=C(CC(=O)OC12CC3CC(C1)CC(C(=O)[O-])(C3)C2)C(=O)OC1(CC)CCCC1] | 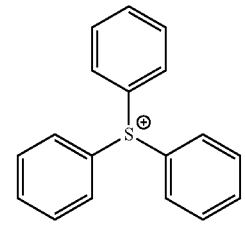 [SMILES: c1ccc([S+](c2ccccc2)c2ccccc2)cc1]<br>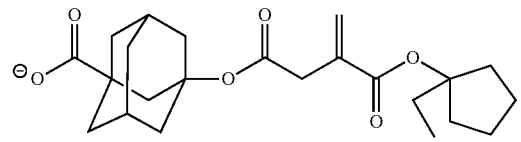 [SMILES: C=C(CC(=O)OC12CC3CC(C1)CC(C(=O)[O-])(C3)C2)C(=O)OC1(CC)CCCC1] |

TABLE 10-continued
| | | |
|---|---|---|
| 40 | 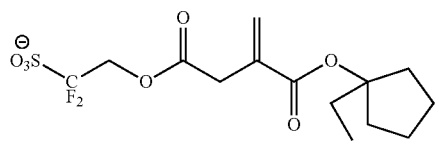 | 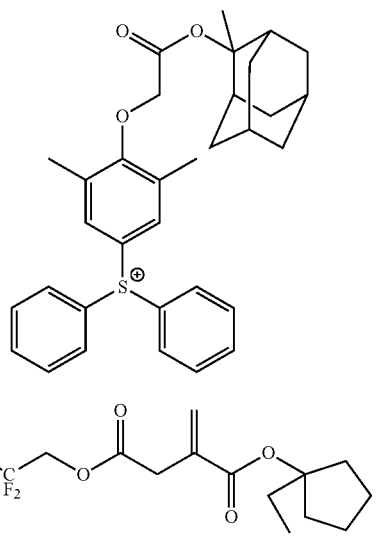 |
| | 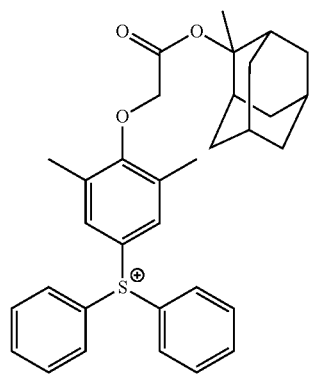 [SMILES: Cc1cc([S+](c2ccccc2)c2ccccc2)cc(C)c1OCC(=O)OC1(C)C2CC3CC(C2)CC1C3] | |
TABLE 11
| Compound | NMR | Cation |
|---|---|---|
| 41 | 7.75-7.86 (m, 10H, ArH), 7.61 (s, 2H, ArH), 6.69 (s, 1H, CH), 5.45 (s, 1H, CH), 4.97-5.04 (t, 2H, CH2), 4.62 (s, 2H, CH2), 3.36 (s, 2H, CH2), 2.31 (s, 6H, CH3), 0.91-2.20 (m, 32H, isopropyl cyclopentyl + Adamantan) | |
| 42 | 7.75-7.86 (m, 10H, ArH), 7.61 (s, 2H, ArH), 6.71 (s, 1H, CH), 5.76 (s, 1H, CH), 4.80-4.87 (t, 2H, CH2), 4.62 (s, 2H, CH2), 3.44 (s, 2H, CH2), 2.31 (s, 6H, CH3), 1.36-2.05 (m, 34H, CH3 + Adamantan) | ↑ |
| 43 | 7.75-7.86 (m, 10H, ArH), 7.61 (s, 2H, ArH), 6.72 (s, 1H, CH), 5.76 (s, 1H, CH), 4.80-4.87 (t, 2H, CH2), 4.62 (s, 2H, CH2), 3.43 (s, 2H, CH2), 2.31 (s, 6H, CH3), 1.05-2.16 (m, 38H, Isopropyl + Adamantan) | ↑ |
| 44 | 7.75-7.86 (m, 10H, ArH), 7.61 (s, 2H, ArH), 6.74 (s, 1H, CH), 5.50 (s, 1H, CH), 4.97-5.04 (t, 2H, CH2), 4.62 (s, 2H, CH2), 4.49 (s, 2H, CH2), 3.40 (s, 2H, CH2), 2.31 (s, 6H, CH3), 1.49-2.21 (m, 34H, Adamantan) | ↑ |

TABLE 11-continued

| Compound | Anion | Product |
|---|---|---|
| 41 | | |
| 42 | | |

TABLE 11-continued
| 43 | 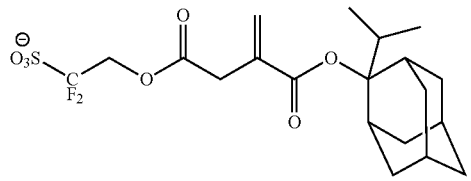 | 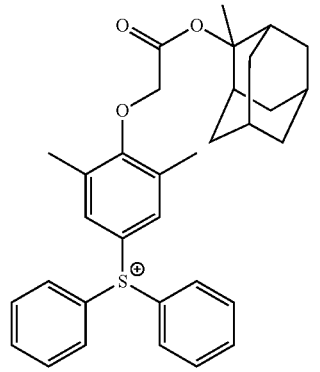 [SMILES: Cc1cc([S+](c2ccccc2)c2ccccc2)cc(C)c1OCC(=O)OC1(C)C2CC3CC(C2)CC1C3] |
|---|---|---|
| | | 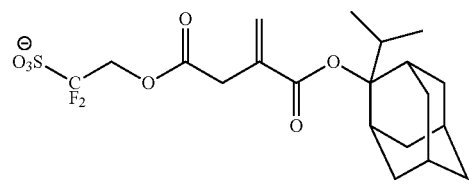 |
| 44 | 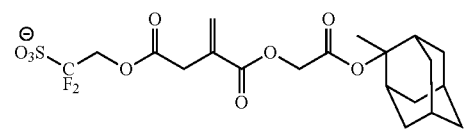 | 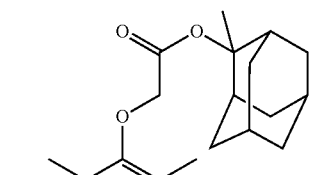 |
| | | 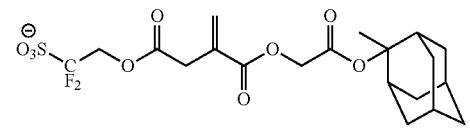 |
TABLE 12
| Compound | NMR | Cation |
|---|---|---|
| 45 | 7.75-7.86 (m, 10H, ArH), 7.61 (s, 2H, ArH), 6.74 (s, 1H, CH), 5.81 (s, 2H, CH2), 5.53 (s, 1H, CH), 4.97-5.04 (t, 2H, CH2), 4.62 (s, 2H, CH2), 3.48 (m, 1H, CH), 3.38 (s, 2H, CH2), 1.00-2.81 (m, 33H, Cyclohexyl + Adamantan + CH3) | 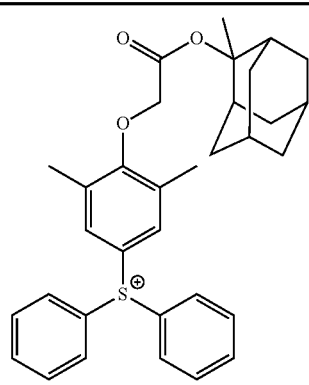 |

TABLE 12-continued
| | | | |
|---|---|---|---|
| 46 | 7.75-7.86 (m, 10H, ArH), 7.61 (s, 2H, ArH), 6.72 (s, 1H, CH), 5.86 (m, 1H, CH), 5.52 (s, 1H, CH), 4.97-5.07 (m, 2H, CH2), 4.62 (s, 2H, CH2), 3.56 (m, 1H, CH), 3.38 (s, 2H, CH2), 2.31 (s, 6H, CH3), 1.00-2.97 (m, 30H, Cyclohexyl + CH3 + Adamantan) | | ↑ |
| 47 | 7.75-7.86 (m, 10H, ArH), 7.61 (s, 2H, ArH), 6.74 (s, 1H, CH), 5.72 (s, 2H, CH2), 5.53 (s, 1H, CH), 4.97-5.04 (t, 2H, CH2), 4.62 (s, 2H, CH2), 3.32-3.38 (m, 3H, CH2 + CH), 1.49-2.31 (m, 37 H, Adamantan + CH3) | | ↑ |
| 48 | 7.75-7.86 (m, 10H, ArH), 7.61 (s, 2H, ArH), 6.72 (s, 1H, CH), 5.79 (m, 1H, CH2), 5.52 (s, 1H, CH), 4.97-5.04 (m, 2H, CH2), 4.62 (s, 2H, CH2), 3.32- 3.38 (m, 3H, CH2 + CH), 1.49-2.31 (m, 37H, Adamantan + CH3), 1.13 (d, 3H, CH3) | | ↑ |
| Compound | Anion | Product |
|---|---|---|
| 45 | 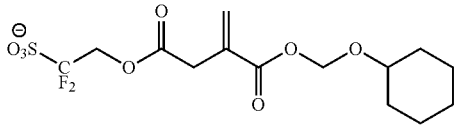 | 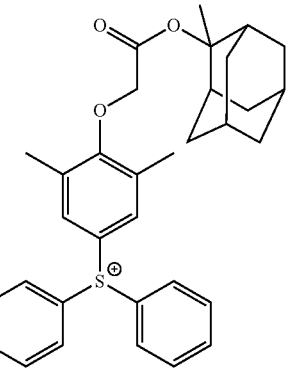 |
| 46 | 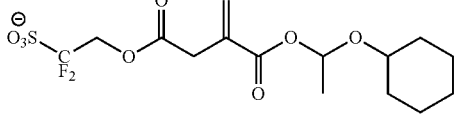 | 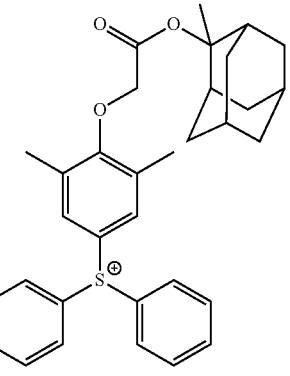 |

TABLE 12-continued
| | | |
|---|---|---|
| 47 | 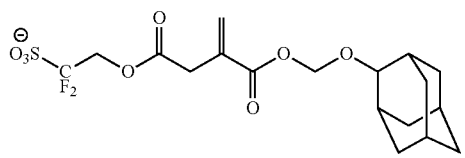 | 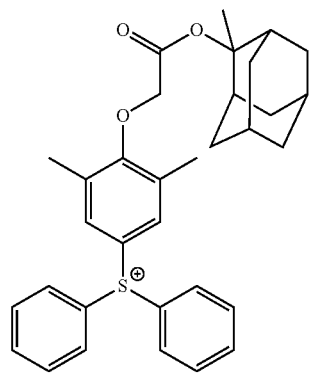 [SMILES: Cc1cc([S+](c2ccccc2)c2ccccc2)cc(C)c1OCC(=O)OC1(C)C2CC3CC(C2)CC1C3] |
| | | 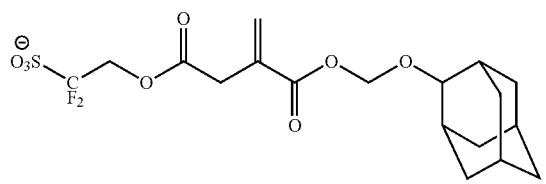 |
| 48 | 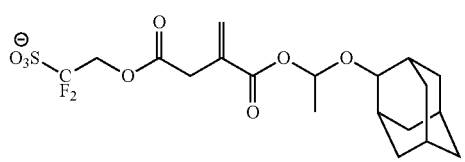 | 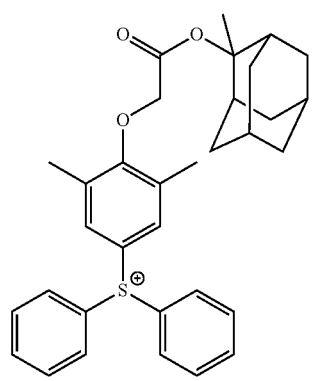 [SMILES: Cc1cc([S+](c2ccccc2)c2ccccc2)cc(C)c1OCC(=O)OC1(C)C2CC3CC(C2)CC1C3] |
| | | 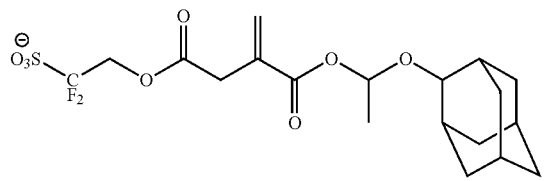 |
TABLE 13
| Compound | NMR | Cation |
|---|---|---|
| 49 | 7.75-7.86 (m, 10H, ArH), 7.61 (s, 2H, ArH), 6.78 (s, 1H, CH), 5.50 (s, 1H, CH), 5.35 (s, 1H, CH), 5.23 (s, 1H, CH), 4.97-5.04 (t, 2H, CH2), 4.62 (s, 2H, CH2), 4.57 (s, 1H, CH), 4.27 (s, 1H, CH), 3.42 (s, 2H, CH2), 2.79 (s, 1H, CH), 2.31 (s, 6H, CH3), 1.75-1.91 (m, 19H, CH + CH + Adamantan) | 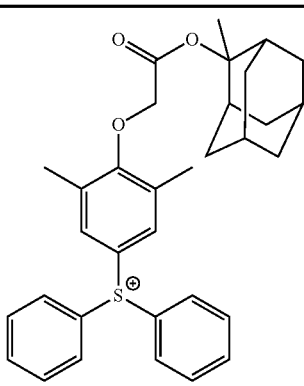 |

TABLE 13-continued

| | |
|---|---|
| 50 | 7.75-7.86 (m, 10H, ArH), 7.61 (s, 2H, ArH), 6.74 (s, 1H, CH), 5.51 (s, 1H, CH), 4.97-5.04 (m, 3H, CH2 + CH), 4.83 (s, 1H, CH), 4.62 (s, 2H, CH2), 3.38 (s, 2H, CH2), 3.27 (s, 1H, CH), 1.44-2.66 (m, 29H, CH + CH + CH2 + CH2 + CH3 + Adamantan) |
| 51 | 7.75-7.86 (m, 10H, ArH), 7.61 (s, 2H, ArH), 6.74 (s, 1H, CH), 5.51 (s, 1H, CH), 4.91-5.19 (m, 4H, CH2 + CH2), 4.62 (s, 2H), CH2), 4.08 (s, 1H, CH), 3.41 (s, 2H, CH2), 1.49-3.31 (m, 29H, CH + CH2 + CH3 + Adamantan) |
| 52 | 7.75-7.86 (m, 10H, ArH), 7.61 (s, 2H, ArH), 6.78 (s, 1H, CH), 5.50 (s, 1H, CH), 5.41-5.47 (m, 4H, CH + CH), 4.97-5.04 (m, 3H, CH2 + CH), 4.80 (m, 2H, CH2), 4.62 (s, 2H, CH2), 4.09 (m, 1H, CH), 2.46-3.42 (m, 4H, CH2 + CH + CH), 2.31 (s, 6H, CH3), 1.49-1.97 (m, 17H, Adamantane) |

| Compound | Anion | Product |
|---|---|---|
| 49 | | |
| 50 | | |

TABLE 13-continued
51 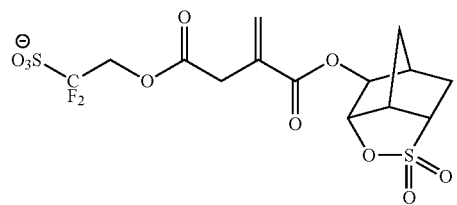 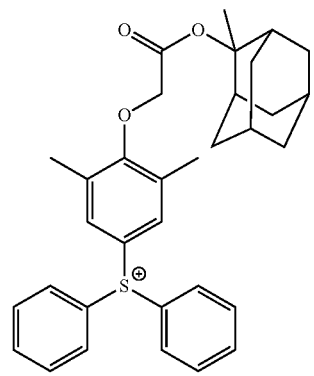 [SMILES: Cc1cc([S+](c2ccccc2)c2ccccc2)cc(C)c1OCC(=O)OC1(C)C2CC3CC(C2)CC1C3]
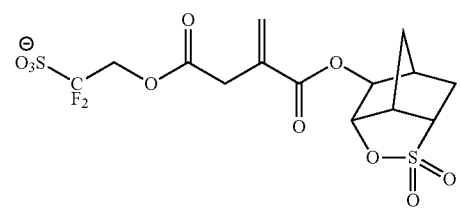
52 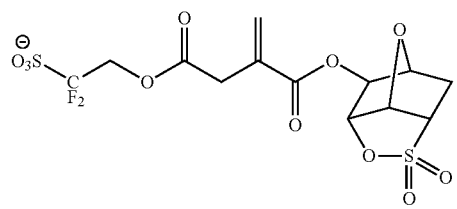 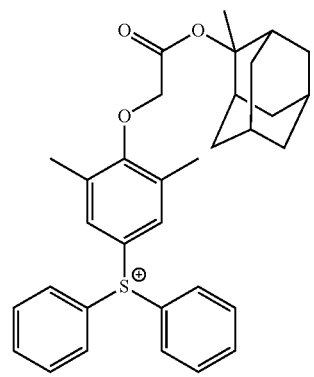 [SMILES: Cc1cc([S+](c2ccccc2)c2ccccc2)cc(C)c1OCC(=O)OC1(C)C2CC3CC(C2)CC1C3]
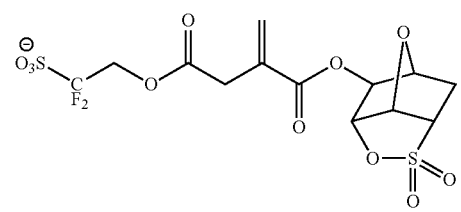

TABLE 14
| Compound | NMR | Cation |
|---|---|---|
| 53 | 7.75-7.86 (m, 10H, ArH), 7.61 (s, 2H, ArH), 6.81 (s, 1H, CH), 5.97 (s, 1H, CH), 5.58 (s, 1H, CH), 4.97-5.04 (t, 2H, CH2), 4.62 (s, 2H, CH2), 4.24-4.48 (m, 2H, CH + CH), 3.38 (s, 2H, CH2), 2.51-2.93 (m, 2H, CH + CH), 2.31 (s, 6H, CH3), 1.49-1.97 (m, 17H, Adamantane) | |
| 54 | 7.75-7.86 (m, 10H, ArH), 7.61 (s, 2H, ArH), 6.74-6.75 (s, 1H, CH), 5.45 (s, 1H, CH), 4.97-5.04 (t, 2H, CH2), 4.62 (s, 2H, CH2), 4.34 (s, 1H, OH), 3.35 (s, 2H, CH2), 1.49-2.88 (m, 37H, Adamantan + CH3) | ↑ |
| 55 | 7.75-7.86 (m, 10H, ArH), 7.61 (s, 2H, ArH), 6.74 (s, 1H, CH), 6.16 (m, 1H, OH), 5.53 (s, 1H, CH), 4.93-5.10 (m, 2H, CH2), 4.59-4.62 (m, 4H, CH2 + CH2), 3.91-3.97 (m, 2H, CH2), 3.39 (s, 2H, CH2), 2.31 (s, 6H, CH3), 1.49-1.97 (m, 17H, Adamantane) | ↑ |
| 56 | 7.75-7.86 (m, 10H, ArH), 7.61 (s, 2H, ArH), 6.59 (s, 1H, CH), 5.47 (s, 1H, CH), 4.62 (s, 2H, CH2), 4.17-4.22 (t, 2H, CH2), 3.50-3.54 (t, 2H, CH2), 3.29 (s, 2H, CH2), 0.91-2.34 (m, 36H, Ethylcyclopentyl + Adamantan + CH3) | ↑ |
| Compound | Anion | Product |
|---|---|---|
| 53 | | 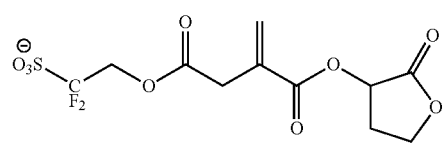 |

TABLE 14-continued
| | | |
|---|---|---|
| 54 | 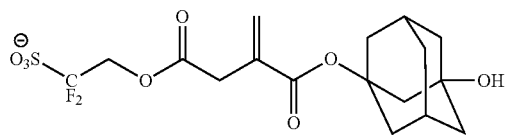 | 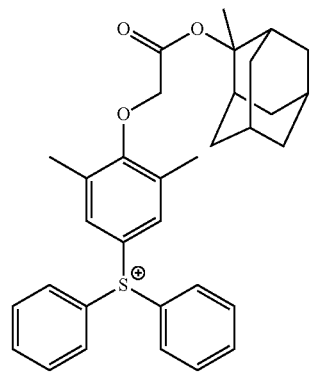 [SMILES: Cc1cc([S+](c2ccccc2)c2ccccc2)cc(C)c1OCC(=O)OC1(C)C2CC3CC(C2)CC1C3]<br>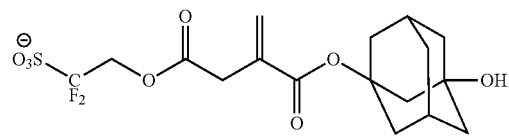 |
| 55 | 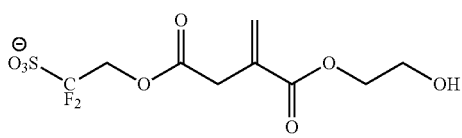 | 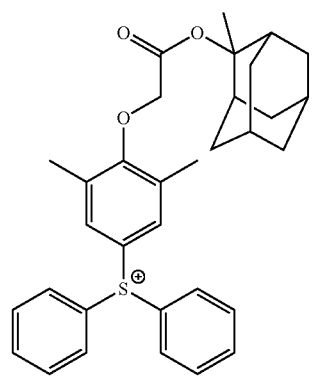 [SMILES: Cc1cc([S+](c2ccccc2)c2ccccc2)cc(C)c1OCC(=O)OC1(C)C2CC3CC(C2)CC1C3]<br>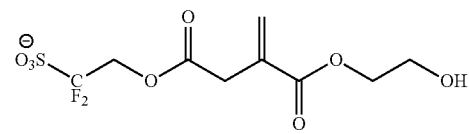 |
| 56 | 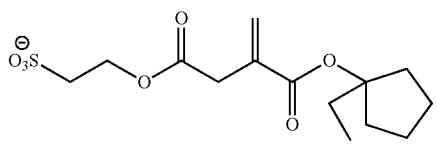 | 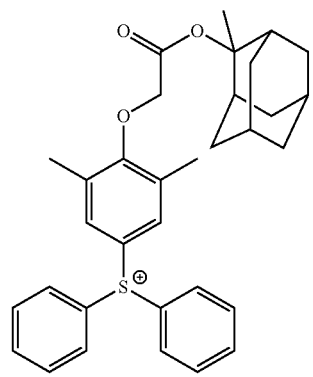 [SMILES: Cc1cc([S+](c2ccccc2)c2ccccc2)cc(C)c1OCC(=O)OC1(C)C2CC3CC(C2)CC1C3]<br>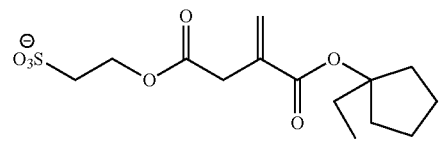 |

TABLE 15

| Compound | NMR | Cation |
|---|---|---|
| 57 | 7.75-7.86 (m, 10H, ArH), 7.61 (s, 2H, ArH), 6.64 (s, 1H, CH) 5.79-5.83 (m, 2H, CH2), 5.58 (s, 1H, CH), 4.62 (s, 2H, CH2), 4.17-4.22 (t, 2H, CH2), 3.50-3.54 (m, 3H, CH2 + CH), 3.30 (s, 2H, CH2), 2.31 (s, 6H, CH3), 1.00-1.97 (m, 27H, cyclohexyl + Adamantan) | (structure shown) |
| 58 | 7.75-7.86 (m, 10H, ArH), 7.61 (s, 2H,, ArH), 6.45 (s, 1H, CH), 5.52 (s, 1H, CH), 4.62 (s, 2H, CH2), 3.95-3.99 (m, 2H, CH2), 3.19 (s, 2H, CH2), 1.49-3.04 (m, 40H, Ethylcyclopentyl + Adamantan + CH2 + CH2 + CH3) | ↑ |
| 59 | 7.75-7.86 (m, 10H, ArH), 7.61 (s, 2H, ArH), 6.45 (s, 1H, CH), 5.53 (s, 1H, CH), 4.85 (m, 1H, CH), 4.62 (s, 2H, CH2), 3.35 (s, 2H, CH2), 0.91-3.26 (m, 49H, Ethylcyclopentyl + camphor + Adamantan + CH3) | ↑ |
| 60 | 7.75-7.86 (m, 14H, Phenyl), 7.61 (s, 2H, ArH), 6.43 (s, 1H, CH), 5.42 (s, 1H, CH), 4.62 (s, 2H, CH2), 4.15-4.18 (t, 2H, CH2), 3.34-3.36 (s, 2H, CH2), 3.23-3.27 (t, 2H, CH2), 0.91-2.38 (m, 36H, Ethylcyclopentyl + CH3 + Adamantan) | ↑ |

| Compound | Anion | Product |
|---|---|---|
| 57 | (structure shown) | (structure shown)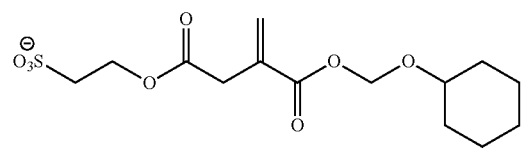 |

TABLE 15-continued
58 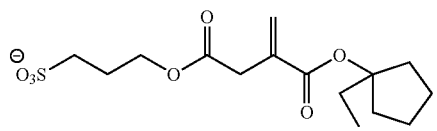 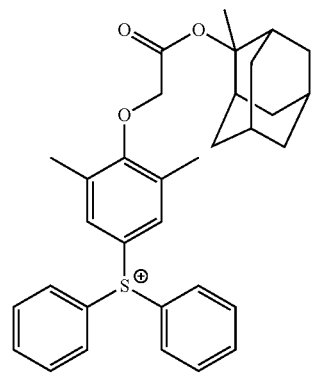
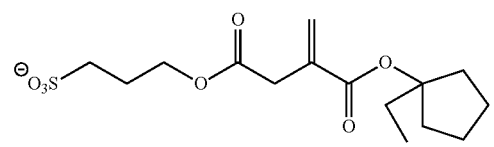
59 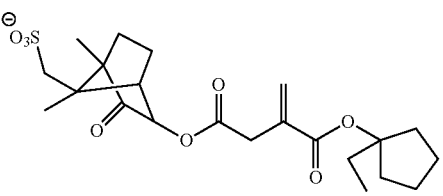 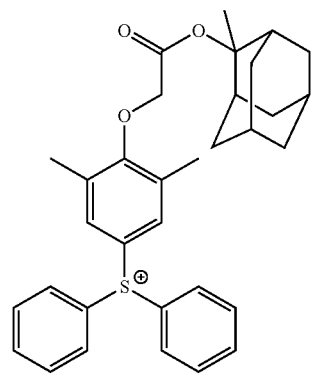
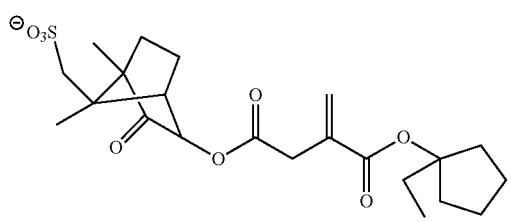

TABLE 15-continued
| 60 | 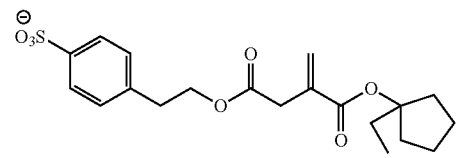 | 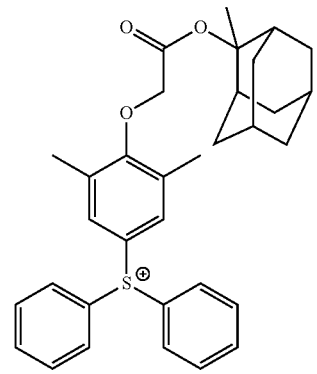 |
|---|---|---|
| | 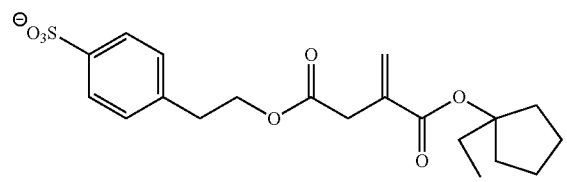 | |
TABLE 16
| Compound | NMR | Cation |
|---|---|---|
| 61 | 7.92-7.94 (d, 2H, Phenyl), 7.75-7.86 (m, 10H, ArH), 7.61 (s, 2H, ArH), 7.49-7.51 (d, 2H, Phenyl), 6.61 (s, 1H, CH), 5.62 (s, 1H, CH), 4.62 (s, 2H, CH2), 3.69 (s, 2H, CH2), 0.91-2.38 (m, 36H, Ethylcyclopentyl + Adamantan + CH3) | 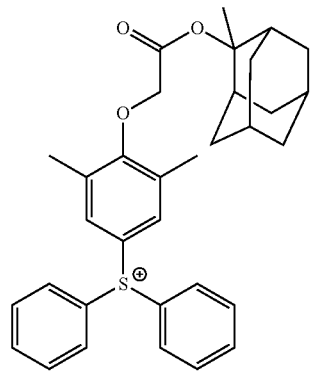 [SMILES: Cc1cc([S+](c2ccccc2)c2ccccc2)cc(C)c1OCC(=O)OC1(C)C2CC3CC(C2)CC1C3] |
| 62 | 7.28-8.62 (m, 18H, Phenyl), 6.61 (s, 1H, CH), 5.62 (s, 1H, CH), 4.62 (s, 2H, CH2), 3.76 (s, 2H, CH), 0.93-2.38 (m, 36H, Ethylcyclopentyl + Adamantan + CH3) | ↑ |
| 63 | 7.02-8.20 (m, 18H, Phenyl), 6.61 (s, 1H, CH), 5.62 (s, 1H, CH), 4.62 (s, 2H, CH2), 3.62 (s, 2H, CH2), 0.91-2.38 (m, 36H, Ethylcyclopentyl + Adamantan + CH3) | ↑ |
| 64 | 7.46-8.43 (m, 18H, Phenyl), 6.61 (s, 1H, CH), 5.62 (s, 1H,CH), 4.62 (s, 2H, CH2), 3.73 (s, 2H, CH2), 0.91-2.38 (m, 36H, Ethylcyclopentyl + Adamantan + CH3) | ↑ |

TABLE 16-continued

| Compound | Anion | Product |
|---|---|---|
| 61 | | |
| 62 | | |

TABLE 16-continued
| | | |
|---|---|---|
| 63 | 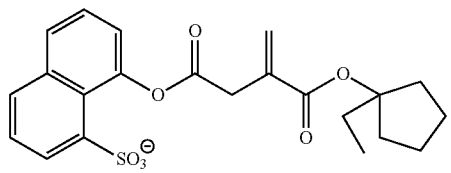 | 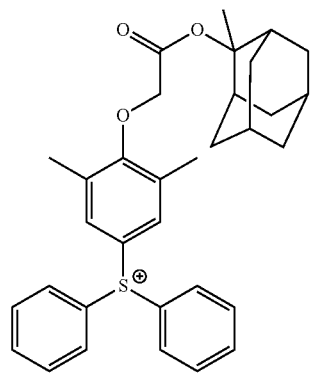 [SMILES: Cc1cc([S+](c2ccccc2)c2ccccc2)cc(C)c1OCC(=O)OC1(C)C2CC3CC(C2)CC1C3] |
| 64 | 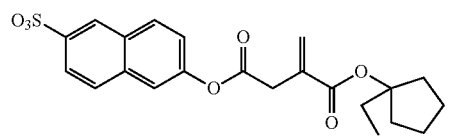 | 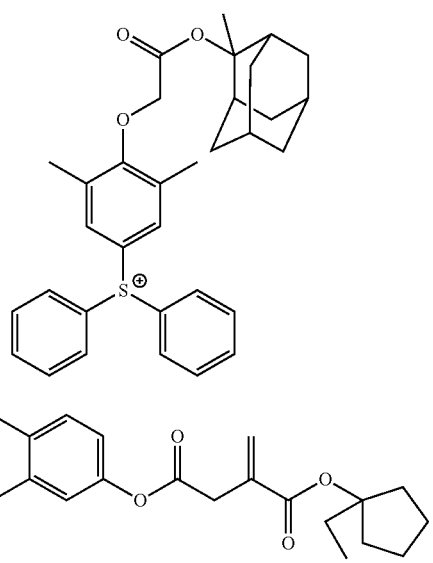 |
TABLE 17
| Compound | NMR | Cation |
|---|---|---|
| 65 | 7.75-8.46 (m, 16H, Phenyl), 7.61 (s, 2H, ArH), 6.61 (s, 1H, CH), 5.62 (s, 1H, CH), 4.62 (s, 2H, CH2), 3.73 (s, 2H, CH2), 0.91-2.38 (m, 36H, Ethylcyclopentyl + Adamantan + CH3) | 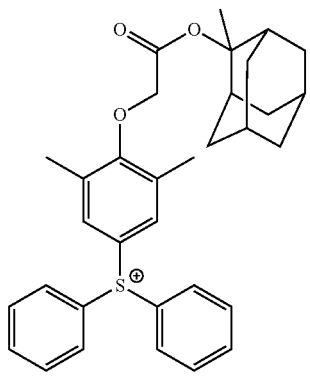 [SMILES: Cc1cc([S+](c2ccccc2)c2ccccc2)cc(C)c1OCC(=O)OC1(C)C2CC3CC(C2)CC1C3] |

TABLE 17-continued
| | | |
|---|---|---|
| 66 | 7.57-8.51 (m, 18H, Phenyl), 6.61 (s, 1H, CH), 5.62 (s, 1H, CH), 4.62 (s, 2H, CH2), 3.62 (s, 2H, CH2), 0.91-2.38 (m, 13H, Ethylcyclopentyl + Adamantan + CH3) | ↑ |
| 67 | 7.05-8.46 (m, 18H, Phenyl), 6.66 (s, 1H, CH), 5.79-5.81 (m, 2H, CH2), 5.73 (s, 1H, CH), 4.62 (s, 2H, CH2), 3.74 (s, 2H, CH2), 1.00-3.48 (m, 34H, cyclohexyl + Adamantan + CH3) | ↑ |
| 68 | 7.75-7.86 (m, 10H, ArH), 7.61 (s, 2H, ArH), 6.50 (s, 1H, CH), 5.79-5.81 (m, 2H, CH2), 5.63 (s, 1H, CH), 4.62 (s, 2H, CH2), 3.97 (s, 2H, CH2), 1.17-3.48 (m, 40H, cyclohexyl + CH2 + CH2 + CH2 + CH3 + Adamantan) | ↑ |
| Compound | Anion | Product |
|---|---|---|
| 65 | 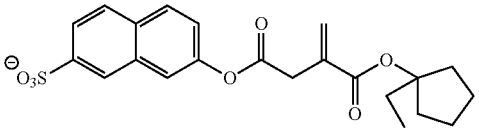 | 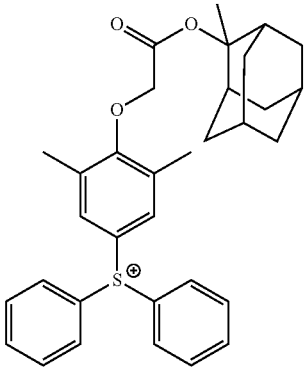 [SMILES: Cc1cc([S+](c2ccccc2)c2ccccc2)cc(C)c1OCC(=O)OC1(C)C2CC3CC(C2)CC1C3] |
| 66 | 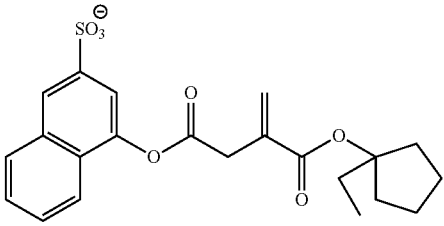 | 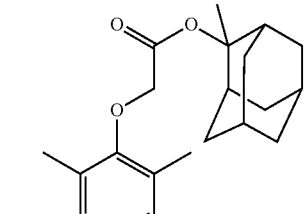 |
| | | 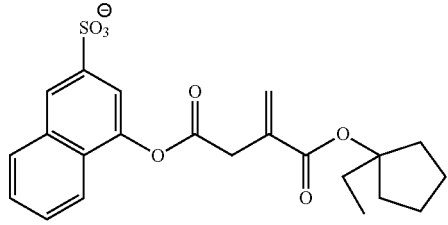 |

TABLE 17-continued
| | | |
|---|---|---|
| 67 | 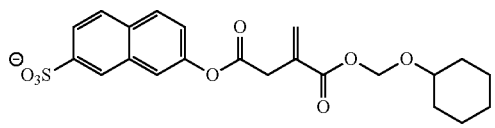 | 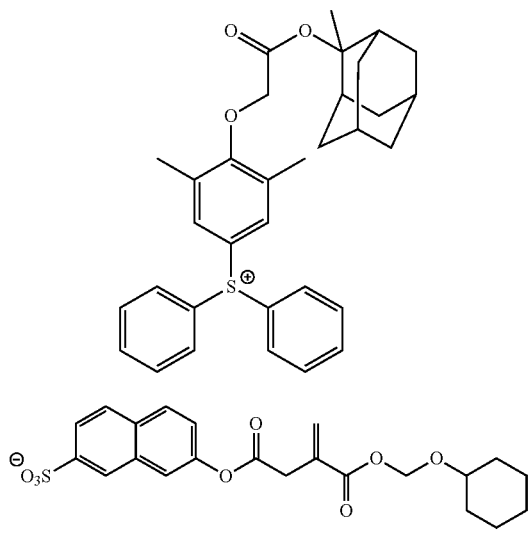 |
| 68 | 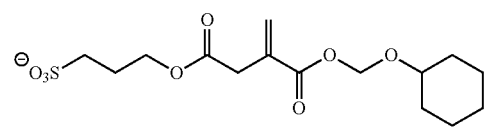 | 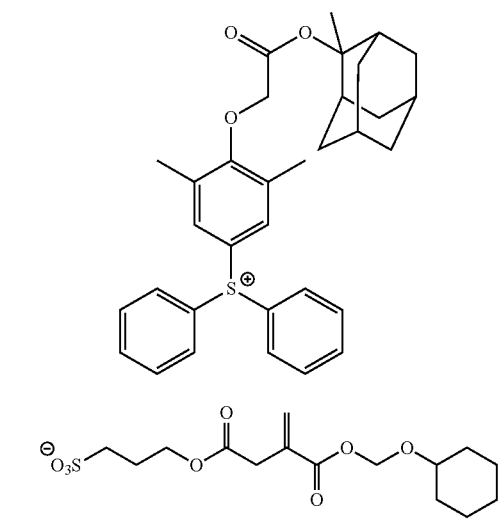 |
TABLE 18
| Compound | NMR | Cation |
|---|---|---|
| 69 | 7.75-7.86 (m, 10H, ArH), 7.61 (s, 2H, ArH), 6.50 (s, 1H, CH), 5.81 (s, 2H, CH2), 5.64 (s, 1H, CH), 4.85 (s, 1H, CH), 4.62 (s, 2H, CH2), 0.91-3.48 (m, 49H, CH3 + Adamantan + Ethylcyclopentyl + camphor) | 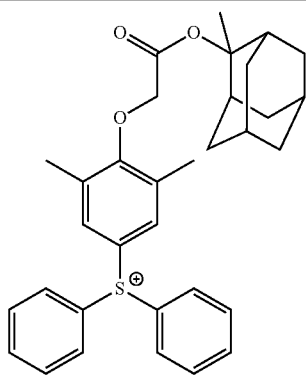 [SMILES: Cc1cc([S+](c2ccccc2)c2ccccc2)cc(C)c1OCC(=O)OC1(C)C2CC3CC(C2)CC1C3] |
| 70 | 7.75-7.86 (m, 10H, ArH), 7.61 (s, 2H, ArH), 6.61 (s, 1H, CH), 5.62 (s, 1H, CH), 4.62 (s, 2H, CH2), 3.67 (s, 2H, CH), 0.91-2.38 (m, 36H, Ethylcyclopentyl + Adamantan + CH3) | ↑ |

TABLE 18-continued
| 71 | 7.75-7.86 (m 10H, ArH), 7.61 (s, 2H, ArH), 6.66 (s, 1H, CH), 5.81 (m, 2H, CH2), 5.73 (s, 1H, CH), 4.62 (s, 2H, CH2), 3.68 (s, 2H, CH2), 3.48 (s, 1H, CH), 2.31 (s, 6H, CH3), 0.96-1.97 (m, 27H, cyclohexyl + Adamantan) | ↑ |
| Compound | Anion | Product |
|---|---|---|
| 69 | 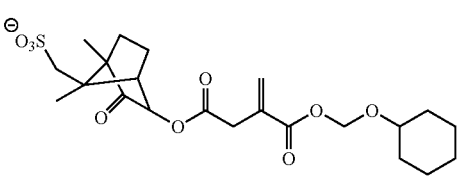 | 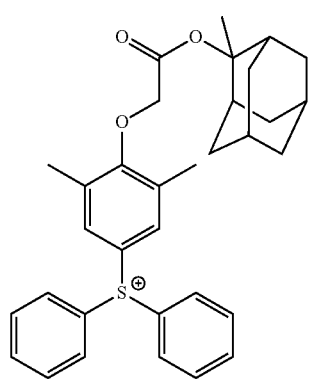 [SMILES: Cc1cc([S+](c2ccccc2)c2ccccc2)cc(C)c1OCC(=O)OC1(C)C2CC3CC(C2)CC1C3] |
| | | 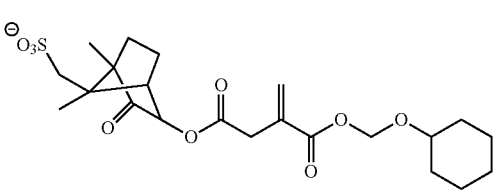 |
| 70 | 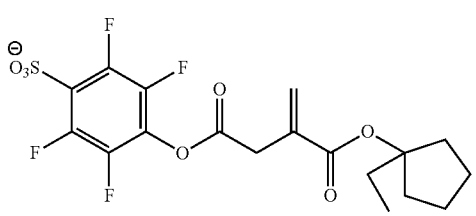 | 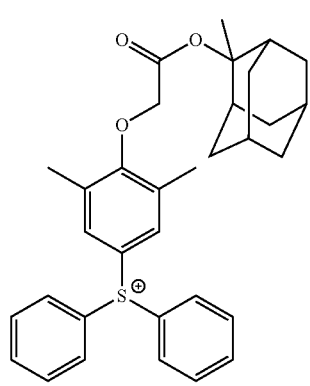 [SMILES: Cc1cc([S+](c2ccccc2)c2ccccc2)cc(C)c1OCC(=O)OC1(C)C2CC3CC(C2)CC1C3] |
| | | 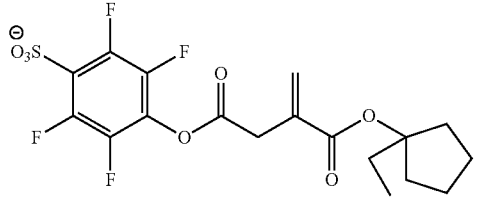 |

TABLE 18-continued
71 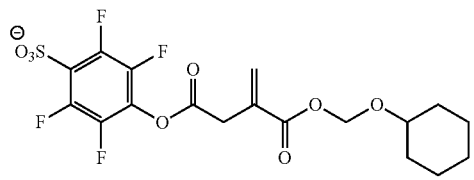 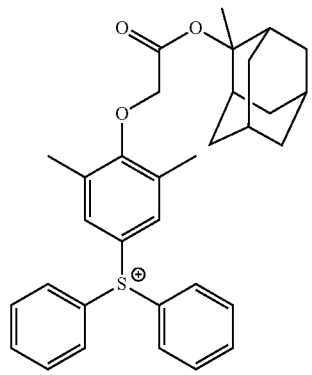 [SMILES: Cc1cc([S+](c2ccccc2)c2ccccc2)cc(C)c1OCC(=O)OC1(C)C2CC3CC(C2)CC1C3]
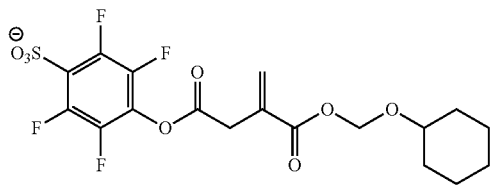
TABLE 19
| Compound | NMR | Cation |
|---|---|---|
| 72 | 7.75-7.86 (m, 10H, ArH), 7.61 (s, 2H, ArH), 6.59 (s, 1H, CH), 5.47 (s, 1H, CH), 4.62 (s, 2H, CH2), 4.47-4.49 (m, 2H, CH2), 3.53-3.57 (m, 2H, CH2), 3.28 (s, 2H, CH2), 0.91-2.38 (m, 36H, EthylCyclopentyl + Adamantan + CH3) | 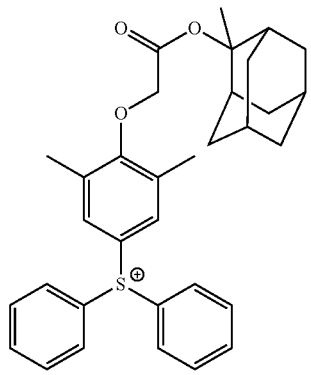 [SMILES: Cc1cc([S+](c2ccccc2)c2ccccc2)cc(C)c1OCC(=O)OC1(C)C2CC3CC(C2)CC1C3] |
| 73 | 7.75-7.86 (m, 10H, ArH), 7.61 (s, 2H, ArH), 6.47 (s, 1H, CH), 5.47 (s, 1H, CH), 4.62 (s, 2H, CH2), 4.24-4.29 (m, 2H, CH2), 3.53-3.57 (m, 2H, CH2), 3.27 (s, 2H, CH2), 0.91-2.38 (m, 36H, EthylCyclopentyl + Adamantan + CH3) | ↑ |
| 74 | 7.75-7.86 (m, 10H, ArH), 7.61 (s, 2H, ArH), 6.69 (s, 1H, CH), 5.42 (s, 1H, CH), 4.87-4.94 (m, 2H, CH2), 4.62 (s, 2H, CH2), 3.39 (s, 2H, CH2), 0.91-2.38 (m, 36H, EthylCyclopentyl + Adamantan + CH3) | ↑ |

TABLE 19-continued

| Compound | Anion | Product |
|---|---|---|
| 72 | | |
| 73 | | |
| 74 | | |

TABLE 20
| Compound | NMR | Cation |
|---|---|---|
| 75 | 7.75-7.86 (m, 10H, ArH), 7.61 (s, 2H, ArH), 6.51 (s, 1H, CH), 5.51 (s, 1H, CH), 4.62 (s, 2H, CH2), 3.57 (s, 1H, CH), 1.49-2.38 (m, 33H, EthylCyclopentyl + Adamantan + CH3), 0.91-0.95 (t, 3H, CH3) | |
| 76 | 7.75-7.86 (m, 10H, ArH), 7.61 (s, 2H, ArH), 6.63 (s, 1H, CH), 5.56 (s, 1H, CH), 4.62-4.64 (m, 4H, CH2 + CH2), 3.47 (s, 1H, CH), 1.49-2.38 (m, 33H, EthylCyclopentyl + Adamantan + CH3), 0.91-0.95 (t, 3H, CH3) | ↑ |
| 77 | 7.75-7.86 (m, 10H, ArH), 7.61 (s, 2H, ArH), 6.41 (s, 1H, CH), 5.53 (s, 1H, CH), 4.62 (s, 2H, CH2), 3.34 (s, 2H, CH2), 1.49-2.38 (m, 48H, EthylCyclopentyl + Adamantan + CH3), 0.91-0.95 (t, 3H, CH3) | ↑ |
| Compound | Anion | Product |
|---|---|---|
| 75 | | 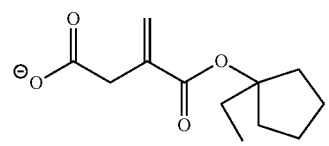 [SMILES: C=C(CC(=O)[O-])C(=O)OC1(CC)CCCC1] |

TABLE 20-continued
| | | |
|---|---|---|
| 76 | 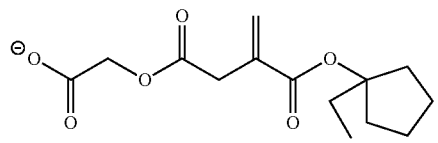 [SMILES: C=C(CC(=O)OCC(=O)[O-])C(=O)OC1(CC)CCCC1] | 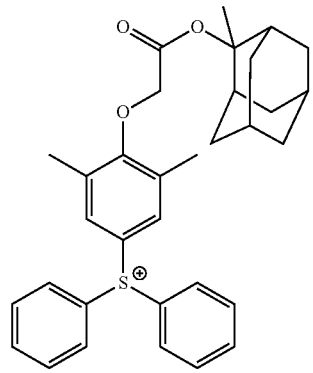 [SMILES: Cc1cc([S+](c2ccccc2)c2ccccc2)cc(C)c1OCC(=O)OC1(C)C2CC3CC(C2)CC1C3] |
| | | 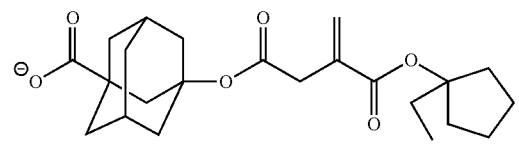 |
| 77 | 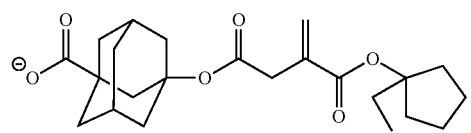 [SMILES: C=C(CC(=O)OC12CC3CC(C1)CC(C(=O)[O-])(C3)C2)C(=O)OC1(CC)CCCC1] | 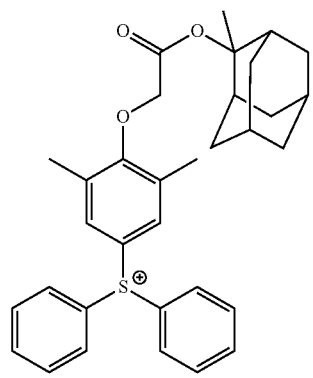 [SMILES: Cc1cc([S+](c2ccccc2)c2ccccc2)cc(C)c1OCC(=O)OC1(C)C2CC3CC(C2)CC1C3] |
TABLE 21
| Compound NMR | Cation |
|---|---|
| 78   8.50 (d, 2H, ArH), 8.37 (d, 2H, ArH), 7.93 (t, 2H, ArH), 7.55-7.75 (m, 7H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl) | 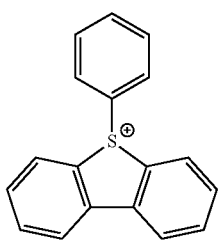 [SMILES: c1ccc(-[s+]2c3ccccc3c3ccccc32)cc1] |

| | |
|---|---|
| 79 | 7.72-7.84 (m, 12H, ArH), 7.56 (d, 2H, ArH), 6.61 (s, 1H, CH), 5.65 (s, 1H, CH), 4.80-4.87 (t, 2H, CH2), 3.41 (s, 2H, CH2), 3.35 (s, 3H, CH3), 0.90-2.34 (m, 13H, Ethylcyclopentyl) |
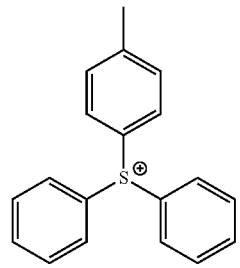 [SMILES: Cc1ccc([S+](c2ccccc2)c2ccccc2)cc1]
| | |
|---|---|
| 80 | 7.76-7.82 (m, 10H, ArH), 7.59 (s, 2H, ArH), 6.61 (s, 1H, CH), 5.65 (s, 1H, CH), 4.80-4.87 (t, 2H, CH2), 4.55 (s, 2H, CH2), 3.41 (s, 2H, CH2), 0.77-2.34 (m, 26H, Ethyl + CH3+ cyclopentyl) |
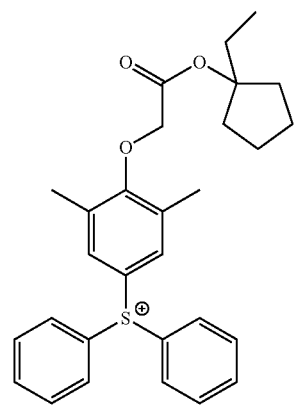 [SMILES: CCC1(OC(=O)COc2c(C)cc([S+](c3ccccc3)c3ccccc3)cc2C)CCCC1]
| | |
|---|---|
| 81 | 10.05 (s, 1H, OH), 7.64-7.87 (m, 10H, ArH), 7.56 (s, 2H, ArH), 7.56 (s, 2H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl + CH3) |
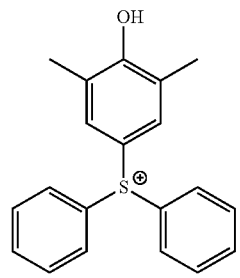 [SMILES: Cc1cc([S+](c2ccccc2)c2ccccc2)cc(C)c1O]
| Compound | Anion | Product |
|---|---|---|
| 78 | 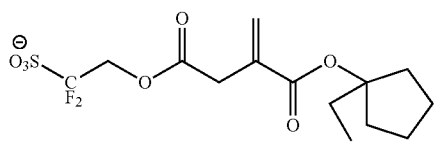 | 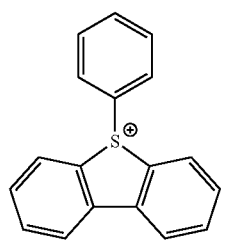 [SMILES: c1ccc(-[s+]2c3ccccc3c3ccccc32)cc1] |
| | | 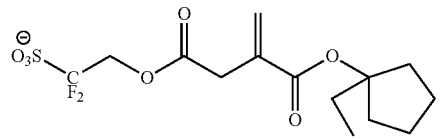 |

TABLE 21-continued
| 79 | ↑ | 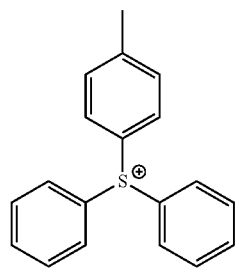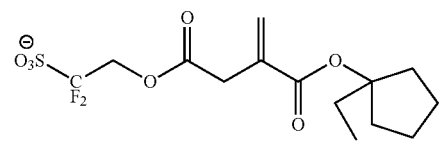 |
| 80 | ↑ | 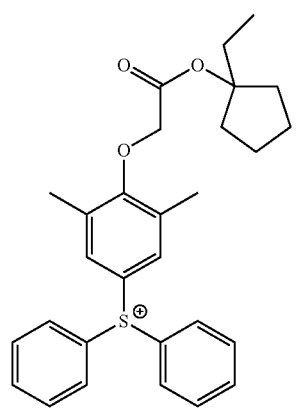 [SMILES: CCC1(OC(=O)COc2c(C)cc([S+](c3ccccc3)c3ccccc3)cc2C)CCCC1]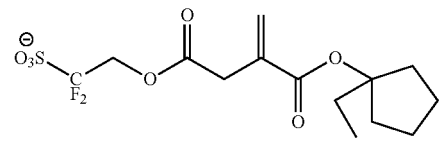 |
| 81 | ↑ | 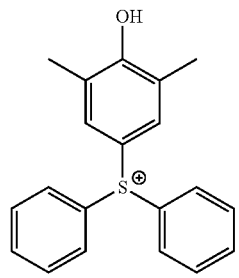 [SMILES: Cc1cc([S+](c2ccccc2)c2ccccc2)cc(C)c1O]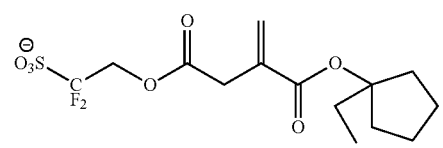 |

TABLE 22

| Compound | NMR | Cation |
|---|---|---|
| 82 | 7.71-7.89 (m, 10H, ArH), 7.59 (s, 2H, ArH), 6.61 (s, 1H, CH), 5.65 (s, 1H, CH), 4.80-4.87 (t, 2H, CH2), 4.53 (s, 2H, CH2), 3.41 (s, 2H, CH2), 0.90-2.34 (m, 19H, Ethylcyclopentyl + CH3) | |
| 83 | 7.75-7.86 (m, 10H, ArH), 7.63 (s, 2H, ArH), 6.61 (s, 1H, CH), 5.65 (s, 1H, CH), 4.80-4.87 (t, 2H, CH2), 4.55 (s, 2H, CH2), 3.41 (s, 2H, CH2), 0.90-2.34 (m, 28H, Ethylcyclopentyl + CH3) | |
| 84 | 7.75-7.87 (m, 10H, ArH), 7.63 (s, 2H, ArH), 6.61 (s, 1H, CH), 5.65 (s, 1H, CH), 4.94 (t, 2H, OCH2CF2), 4.80-4.87 (t, 4H, CH2), 3.41 (s, 2H, CH2), 0.90-2.37 (m, 19H, Ethylcyclopentyl + CH3) | |
| 85 | 7.72-7.83 (m, 10H, ArH), 7.59 (s, 2H, ArH), 6.61 (s, 1H, CH), 5.65 (s, 1H, CH), 4.80-4.90 (t, 3H, CH2 + CH), 4.62-4.68 (m, 3H, CH2O + sultone), 3.83-3.89 (m, 1H, sultone), 3.41-3.43 (m, 3H, CH2 + CH), 0.90-2.49 (m, 24H, Ethylcyclopentyl + sultone + CH3) | |

TABLE 22-continued
| Compound | Anion | Product |
|---|---|---|
| 82 | 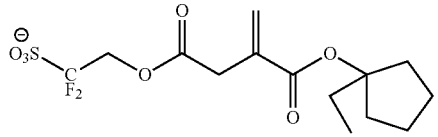 | 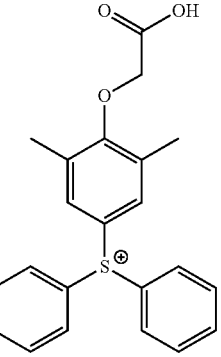 |
| 83 | ↑ | 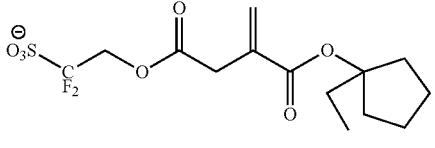 |
| 84 | ↑ | 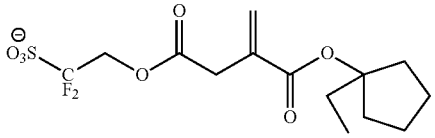 |

TABLE 22-continued
| | | |
|---|---|---|
| 85 | ↑ | 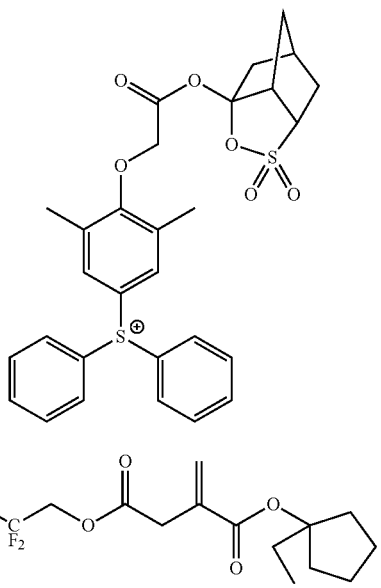 |
TABLE 23
| Compound | NMR | Cation |
|---|---|---|
| 86 | 7.99-8.01 (d, 2H, Ar), 7.73-7.76 (t, 1H, Ar), 7.58-7.61 (t, 2H, Ar), 6.61 (s, 1H, CH), 5.65 (s, 1H, CH), 5.31 (s, 2H, SCH2C=O), 4.80-4.87 (t, 2H, CH2), 3.49-3.62 (m, 4H, CH2), 3.41 (s, 2H, CH2), 0.90-2.49 (m, 17H, Ethylcyclopentyl + CH2) | 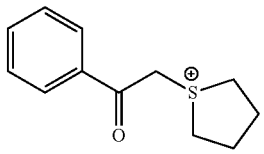 [SMILES: O=C(C[S+]1CCCC1)c1ccccc1] |
| 87 | 8.02-8.05 (m, 2H, Phenyl), 7.61-7.73 (m, 3H, Phenyl), 6.61 (s, 1H, CH), 5.65 (s, 1H, CH), 4.80-4.87 (t, 2H, CH2), 3.76-3.86 (m, 4H, SCH2), 3.41 (s, 2H, CH2), 0.90-2.34 (m, 19H, Ethylcyclopentyl + CH2) | 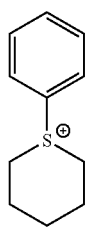 [SMILES: c1ccc([S+]2CCCCC2)cc1] |
| 88 | 8.04-8.09 (m, 2H, Phenyl), 7.69-7.79 (m, 3H, Phenyl), 6.61 (s, 1H, CH), 5.65 (s, 1H, CH), 4.80-4.87 (t, 2H, CH2), 3.41 (s, 2H, CH2), 3.29 (s, 6H, CH3) 0.90-2.34 (m, 13H, Ethylcyclopentyl) | 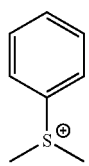 |
| 89 | 8.07 (d, 2H, Phenyl), 7.81 (d, 2H, Phenyl), 6.61 (s, 1H, CH), 5.65 (s, 1H, CH), 4.80-4.87 (t, 2H, CH2), 4.10 (t, 2H, CH2), 3.59 (d, 2H, CH2), 3.41 (s, 2H, CH2), 0.90-2.34 (m, 28H, Ethylcyclopentyl + CH2 + tBu) | 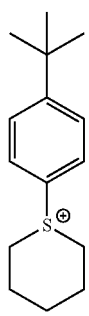 [SMILES: CC(C)(C)c1ccc([S+]2CCCCC2)cc1] |

TABLE 23-continued
| Compound | Anion | Product |
|---|---|---|
| 86 | 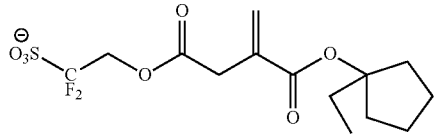 | 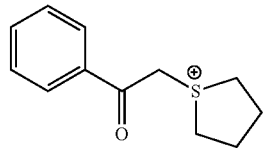 [SMILES: O=C(C[S+]1CCCC1)c1ccccc1] |
| 87 | ↑ | 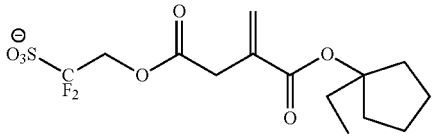 |
| 88 | ↑ | 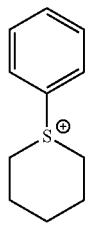 [SMILES: c1ccc([S+]2CCCCC2)cc1] |
| 89 | ↑ | 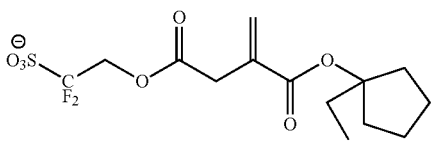 |

TABLE 24
| Compound | NMR | Cation |
|---|---|---|
| 90 | 7.76-7.87 (m, 10H, ArH), 7.69 (s, 2H, ArH), 6.61 (s, 1H, CH), 5.65 (s, 1H, CH), 4.80-4.87 (t, 2H, CH2), 3.41 (s, 2H, CH2), 0.90-2.34 (m, 34H, Ethylcyclopentyl + Adamantan + CH3) | 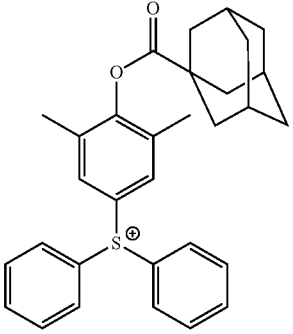 [SMILES: Cc1cc([S+](c2ccccc2)c2ccccc2)cc(C)c1OC(=O)C12CC3CC(CC(C3)C1)C2] |
| 91 | 7.79-7.93 (m, 12H, ArH), 6.61 (s, 1H, CH), 5.65 (s, 1H, CH), 4.80-4.87 (t, 2H, CH2), 3.41 (s, 2H, CH2), 2.73 (t, 2H, CO—CH2), 0.85-2.34 (m, 38H, Ethylcyclopentyl + CH2 + CH3) | 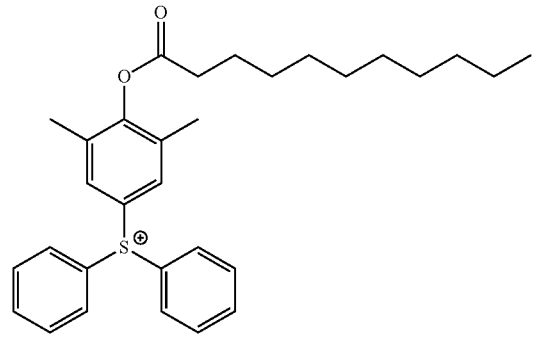 [SMILES: CCCCCCCCCCC(=O)Oc1c(C)cc([S+](c2ccccc2)c2ccccc2)cc1C] |
| 92 | 8.76 (s, 1H, ArH), 8.59-8.64 (m, 1H, ArH), 8.42 (t, 2H, ArH), 8.03-8.19 (m, 5H, ArH), 7.81 (t, 1H, ArH), 7.69 (t, 2H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl) | 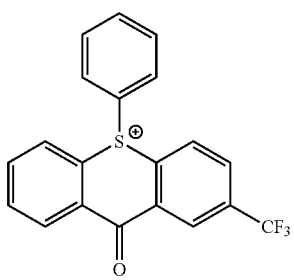 [SMILES: O=c1c2ccccc2[s+](-c2ccccc2)c2ccc(C(F)(F)F)cc12] |
| 93 | 6.61 (s, 1H, CH), 5.65 (s, 1H, CH), 4.80-4.87 (t, 2H, CH2), 3.41 (s, 2H, CH2), 3.36 (t, 6H, CH2), 0.81-2.34 (m, 34H, Ethylcyclopentyl + CH2 + CH3) | 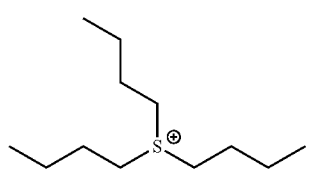 |

TABLE 24-continued

| Compound | Anion | Product |
|---|---|---|
| 90 | (structure) | (structure) |
| 91 | ↑ | (structure) |
| 92 | ↑ | (structure) |

TABLE 24-continued
| 93 | ↑ | 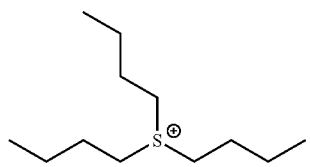<br>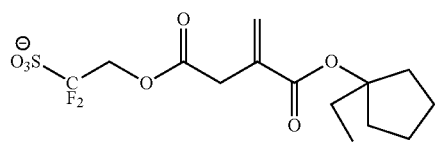 |
TABLE 25
| Compound | NMR | Cation |
|---|---|---|
| 94 | 8.29 (d, 4H, ArH), 7.93-8.09 (m, 6H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl) | 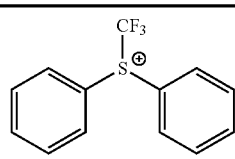 |
| 95 | 7.75-7.87 (m, 10H, ArH), 7.62 (s, 2H, ArH), 6.61 (s, 1H, CH), 5.65 (s, 1H, CH), 4.80-4.87 (t, 2H, CH2), 3.97-3.41 (m, 4H, CH2), 2.56 (m, 10H, CH2, CH3), 0.90-2.34 (m, 13H, Ethylcyclopentyl) | 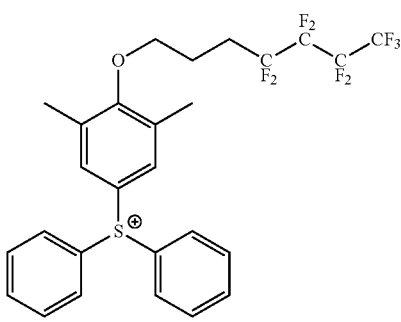 [SMILES: Cc1cc([S+](c2ccccc2)c2ccccc2)cc(C)c1OCCCC(F)(F)C(F)(F)C(F)(F)C(F)(F)F] |
| 96 | 8.24 (d, 4H, ArH), 7.59 (t, 2H, ArH), 7.47 (t, 4H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl) | 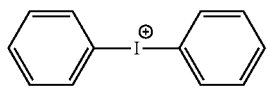 [SMILES: c1ccc([I+]c2ccccc2)cc1] |
| 97 | 6.61 (s, 1H, CH), 5.65 (s, 1H, CH), 4.80-4.87 (t, 2H, CH2), 4.46 (s, 2H, CH2(C=O)), 3.38-3.58 (m, 6H, CH2), 0.90-2.34 (m, 34H, Adamantan + Ethylcyclopentyl + CH2) | 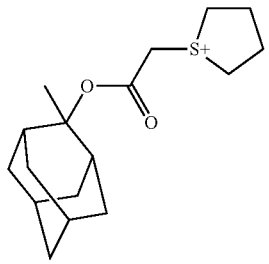 [SMILES: CC1(OC(=O)C[S+]2CCCC2)C2CC3CC(C2)CC1C3] |
| Compound | Anion | Product |
|---|---|---|
| 94 | 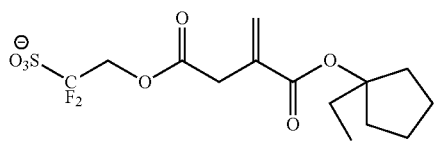 | 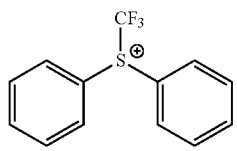 [SMILES: FC(F)(F)[S+](c1ccccc1)c1ccccc1]<br>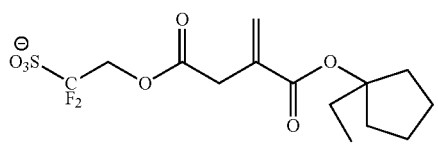 |

TABLE 25-continued
| 95 | ↑ | 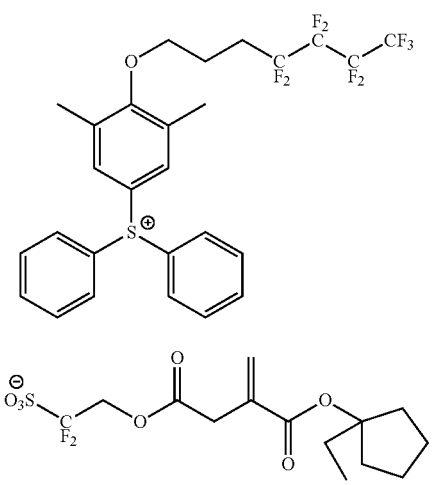 |
| 96 | ↑ | 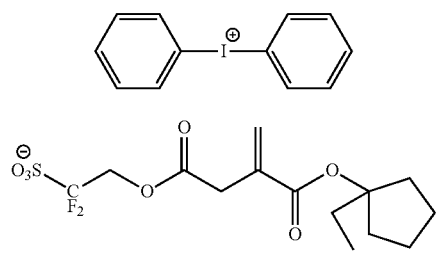 |
| 97 | ↑ | 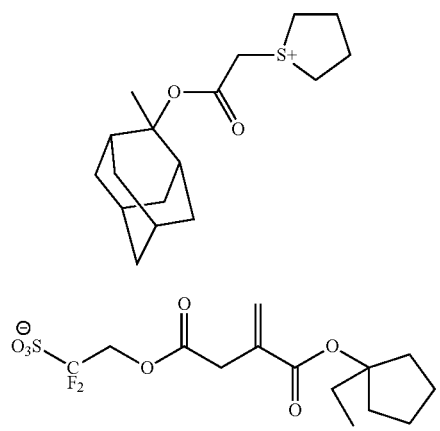 |

TABLE 26

| Compound | NMR | Cation |
|---|---|---|
| 98 | 7.75 (s, 2H, Ar), 6.61 (s, 1H, CH), 5.65 (s, 1H, CH), 4.80-4.87 (t, 2H, CH2), 3.91-3.96 (m, 2H, CH2), 3.72-3.79 (m, 2H, CH2), 3.41 (s, 2H, CH2), 0.90-2.41 (m, 38H, Ethylcyclopentyl + Adamantan + CH2 + CH3) | |
| 99 | 7.77-7.89 (m, 10H, ArH), 7.64 (s, 2H, ArH), 6.61 (s, 1H, CH), 5.65-70 (m, 2H, CH), 4.80-4.87 (m, 4H, CH2), 4.46-4.30 (m, 2H, OCOCH2), 3.41 (s, 2H, CH2), 2.71-2.64 (m, 1H, OCH2CH2), 0.90-2.34 (m, 20H, Ethylcyclopentyl + CH3 + CH2) | |
| 100 | 8.28 (d, 2H, ArH), 8.11 (d, 1H, ArH), 7.86 (t, 1H, ArH), 7.63-7.81 (m, 7H, ArH), 6.61 (s, 1H, CH), 5.65 (s, 1H, CH), 4.80-4.87 (t, 2H, CH2), 3.41 (s, 2H, CH2), 0.90-2.34 (m, 13H, Ethylcyclopentyl) | |
| 101 | 8.41 (m, 2H, ArH), 8.12 (d, 1H, ArH), 7.37-7.93 (m, 2H, ArH), 7.19 (d, 1H, ArH), 6.61 (s, 1H, CH), 5.65 (s, 1H, CH), 5.23 (s, 2H, CH2), 4.80-4.95 (t, 3H, CH2 + Adamantan), 4.03 (m, 2H, CH2S), 3.75 (m, 2H, CH2S), 3.41 (s, 2H, CH2), 0.90-2.43 (m, 31H, Ethylcyclopentyl + Adamantan + CH2) | |

TABLE 26-continued
| Compound | Anion | Product |
|---|---|---|
| 98 | 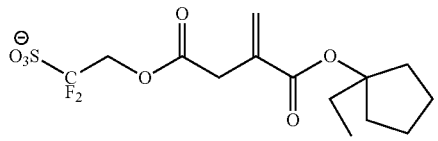 | 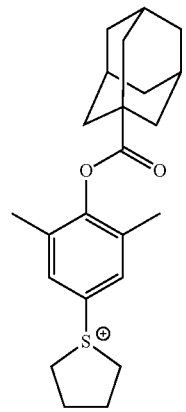 [SMILES: Cc1cc([S+]2CCCC2)cc(C)c1OC(=O)C12CC3CC(CC(C3)C1)C2] |
| 99 | ↑ | 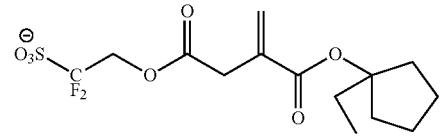 |
| 100 | ↑ | 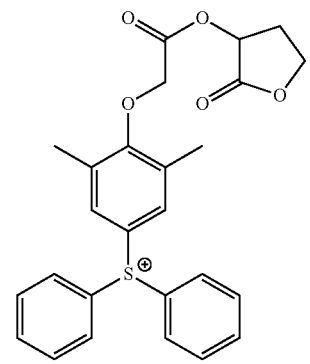 [SMILES: Cc1cc([S+](c2ccccc2)c2ccccc2)cc(C)c1OCC(=O)OC1CCOC1=O] |

TABLE 26-continued

| 101 | ↑ | 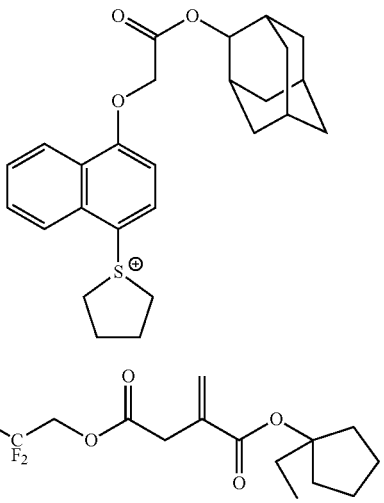 |

Examples 1 to 3, Comparative Examples 1 to 2

The components shown in Table 27 were mixed together and dissolved to obtain positive resist compositions.

TABLE 27

| | Component (A) | Component (B) | | Component (D) | Component (E) | Component (S) |
|---|---|---|---|---|---|---|
| Ex. 1 | (A)-1 | (B)-1 | (B)-6 | (D)-1 | (E)-1 | (S)-1 |
| | [100] | [9.02] | [3.11] | [0.38] | [0.47] | [2,400] |
| Ex. 2 | (A)-1 | (B)-2 | (B)-6 | (D)-1 | (E)-1 | (S)-1 |
| | [100] | [10.10] | [3.11] | [0.38] | [0.47] | [2,400] |
| Ex. 3 | (A)-1 | (B)-3 | (B)-6 | (D)-1 | (E)-1 | (S)-1 |
| | [100] | [9.79] | [3.11] | [0.38] | [0.47] | [2,400] |
| Comp. Ex. 1 | (A)-1 | (B)-4 | (B)-6 | (D)-1 | (E)-1 | (S)-1 |
| | [100] | [6.99] | [3.11] | [0.38] | [0.47] | [2,400] |
| Comp. Ex. 2 | (A)-1 | (B)-5 | (B)-6 | (D)-1 | (E)-1 | (S)-1 |
| | [100] | [8.00] | [3.11] | [0.38] | [0.47] | [2,400] |

In Table 27, the reference characters indicate the following. Further, the values in brackets [ ] indicate the amount (in terms of parts by weight) of the component added.

(A)-1: a copolymer represented by chemical formula (A)-1 shown below (A)-1 (Mw: 7,000; Mw/Mn: 1.75. In the chemical formula, the subscript numerals shown on the bottom right of the parentheses ( ) indicate the percentage (mol %) of the respective structural units.)

(B)-1: the aforementioned compound 1

(B)-2: the aforementioned compound 12

(B)-3: the aforementioned compound 16

(B)-4: a compound (B)-4 shown below (B)-5: tripehnylsulfonium nonafluorobutanesulfonate (B)-6: tripehnylsulfonium d-camphor-10-sulfonate (D)-1: tri-n-pentylamine (E)-1: salicylic acid (S)-1: a mixed solvent of PGMEA/PGME=6/4 (weight ratio)

[Chemical Formula 76]

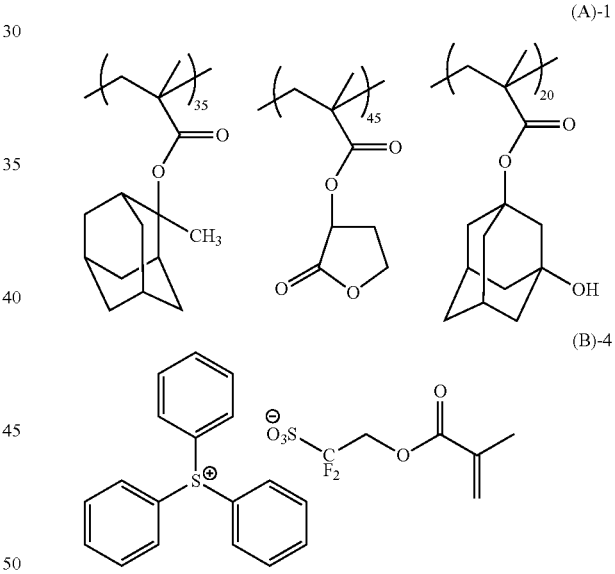

[Formation of Resist Pattern (1)]

An organic antireflection film composition (product name: ARC29A, manufactured by Brewer Science Ltd.) was applied onto an 12-inch silicon wafer using a spinner, and the composition was then baked and dried on a hotplate at 205° C. for 60 seconds, thereby forming an organic antireflection film having a film thickness of 89 nm.

Subsequently, each of the resist compositions obtained above was applied onto the organic antireflection film using a spinner, and was then prebaked (PAB) on a hotplate at 110° C. for 60 seconds and dried, thereby forming a resist film having a film thickness of 90 nm.

Then, a coating solution for forming a protection film (product name: TILC-057; manufactured by Tokyo Ohka Kogyo Co., Ltd.) was applied onto the resist film using a spinner, and then heated at 90° C. for 60 seconds, thereby forming a top coat with a film thickness of 35 nm.

Thereafter, using an ArF exposure apparatus for immersion lithography (product name: NSR-S609B, manufactured by Nikon Corporation, NA (numerical aperture)=1.07), the resist film having a top coat formed thereon was selectively irradiated with an ArF excimer laser (193 nm) through a mask.

Then, a post exposure bake (PEB) treatment was conducted at 110° C. for 60 seconds, followed by alkali development for 10 seconds at 23° C. in a 2.38% by weight aqueous solution of tetramethylammonium hydroxide (TMAH) (product name: NMD-3; manufactured by Tokyo Ohka Kogyo Co., Ltd.). Then, the resist was washed for 30 seconds with pure water, followed by drying by shaking.

Further, a post bake was conducted at 100° C. for 45 seconds.

As a result, in each of the examples, a line and space resist pattern (hereafter, referred to as an "LS pattern") in which lines having a line width of 49 nm were spaced at equal intervals (pitch: 98 nm) was formed on the resist film.

[Evaluation of Resist Pattern (1)]
[Evaluation of Mask Error Factor (MEF)]

In accordance with the same procedure and the same exposure dose as those used for forming the above LS pattern, LS patterns having a pitch of 98 nm were formed using mask patterns targeting line pattern sizes of 45 nm to 54 nm (a total of 10 targets at intervals of 1 nm). The value of the mask error factor (MEF) was determined as the gradient of a linear graph obtained by plotting the target size (nm) on the horizontal axis and plotting the actual size (nm) of the line patterns formed on the resist film using the respective mask patterns on the vertical axis. A MEF value (gradient of the plotted line) closer to 1 indicates that a resist pattern faithful to the mask pattern was formed. The results are shown in Table 28.

[Evaluation of Line Width Roughness (LWR)]

With respect to the above LS patterns, the space width at 400 points in the lengthwise direction of the space were measured using a measuring scanning electron microscope (SEM) (product name: S-9380, manufactured by Hitachi High-Technologies Corporation; acceleration voltage: 300V). From the results, the value of 3 times the standard deviation s (i.e., 3s) was determined, and the average of the 3s values at 400 points was calculated as a yardstick of LWR. The results are shown in Table 28.

The smaller this 3s value is, the lower the level of roughness of the line width, indicating that a LS pattern with a uniform width was obtained.

[Evaluation of Exposure Latitude (EL Margin)]

With respect to the exposure dose for forming the above LS patterns, the exposure dose with which the lines of LS patterns were able to be formed within a dimensional variation of ±5% from the target dimension was determined, and the EL margin (unit: %) was determined by the following formula. The results are shown in Table 28.

EL margin (%)=(|E1−E2|/EOP)×100

E1: Exposure dose (mJ/cm$^2$) with which an LS pattern having a hole diameter of 46.5 nm was formed; E2: Exposure dose (mJ/cm$^2$) with which an LS pattern having a hole diameter of 51.5 nm was formed The larger the value of EL margin, the smaller the fluctuation in the pattern size accompanied by the variation in the exposure dose.

[Evaluation of Pattern Shape]

With respect to the (1:1) LS patterns formed with the above optimum exposure dose Eop, the cross sectional shape was observed using a scanning electron microscope (product name: SU-8000, manufactured by Hitachi High-Technologies Corporation) to evaluate the cross sectional shape. The results are shown in Table 28.

TABLE 28

|  | MEF | LWR (nm) | EL (%) | Shape |
| --- | --- | --- | --- | --- |
| Ex. 1 | 2.50 | 5.4 | 7.35 | Vertical |
| Ex. 2 | 2.48 | 6.3 | 7.14 | Vertical |
| Ex. 3 | 2.61 | 5.9 | 7.44 | Vertical |
| Comp. Ex. 1 | 3.13 | 8.0 | 5.37 | T-Top |
| Comp. Ex. 2 | 3.42 | 7.2 | 4.99 | Top round |

From the above results, it was confirmed that the resist compositions of Examples 1 to 3 were superior compared to the resist compositions of Comparative Examples 1 and 2 in that they exhibited excellent lithography properties (such as MEF, LWR and EL margin) and pattern shape.

Polymer Synthesis Example 1

Synthesis of Polymeric Compound 1

20 g (117.5 mmol) of a monomer 1, 27.5 g (117.5 mmol) of a monomer 2, 13.9 g (58.8 mmol) of a monomer 3 and 5.51 g (8.73 mmol) of a monomer 4 were dissolved in 80 g of cyclohexanone in a three-necked flask equipped with a thermometer and a reflux tube. Subsequently, 7.77 g of dimethyl azobisisobutyrate (V-601) was added and dissolved in the resulting solution as a polymerization initiator.

The resulting solution was added dropwise, over a period of four hours and under a nitrogen atmosphere, to 30 g of cyclohexanone which was heated to 80° C. Following completion of the dropwise addition, the reaction solution was stirred for one hour under heat, and was then cooled to room temperature.

The thus obtained polymerization reaction solution was added dropwise to a large volume of methanol to precipitate a polymer, and the precipitated white powder was separated by filtration, washed with methanol and heptane, and subsequently dried, thereby yielding 53.1 g of a polymeric compound 1 as the target compound.

For this polymeric compound, the polystyrene-equivalent weight average molecular weight (Mw) determined by GPC measurement was 7,500, and the molecular weight dispersity (Mw/Mn) was 1.76.

Further, the compositional ratio of the copolymer (the percentage (molar ratio) of each of the structural units within the structural formula) determined by $^{13}$C-NMR was l/m/n/o=40.1/36.9/19.3/3.7.

[Chemical Formula 77]
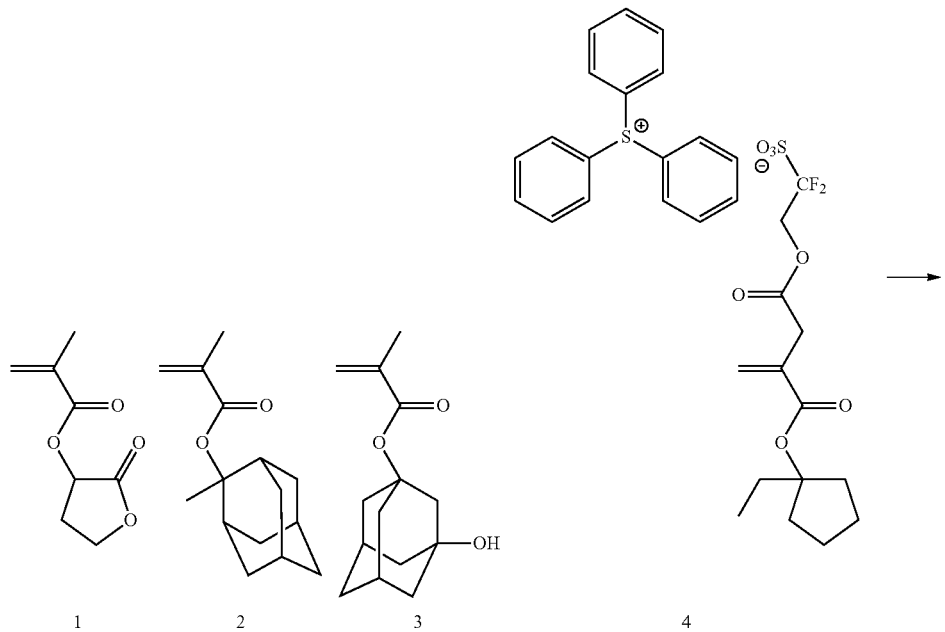
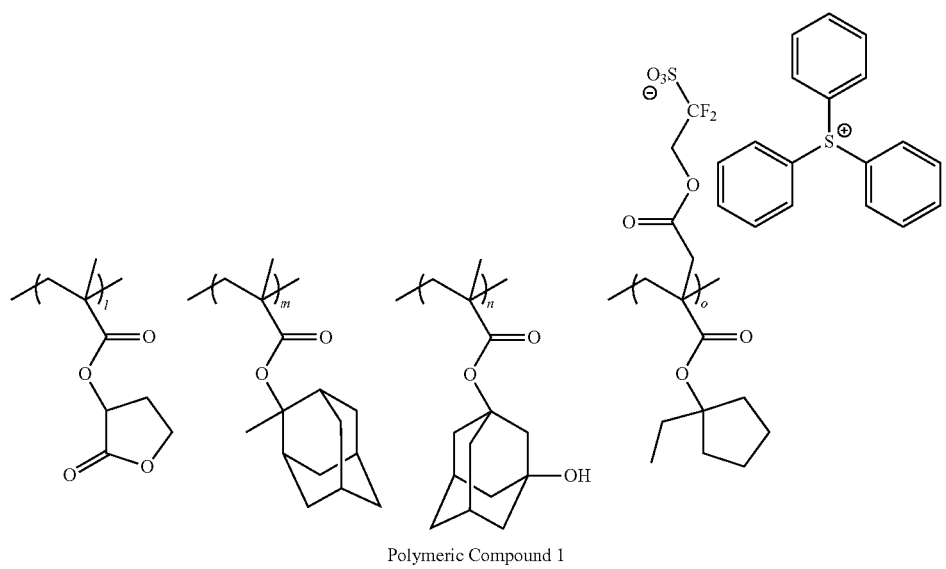
Polymeric Compound 1
Polymer Synthesis Examples 2 to 9
Synthesis of Polymeric Compounds 2 to 9
Polymeric compounds 2 to 9 shown below were synthesized in the same manner as in Polymer Synthesis Example 1 described above with the exception that the type and compositional ratio of monomers were changed.
[Chemical Formula 78]
Polymeric Compound 2
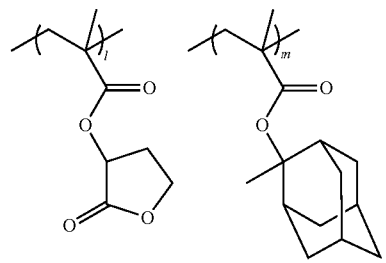

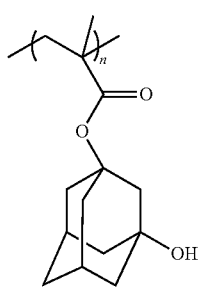
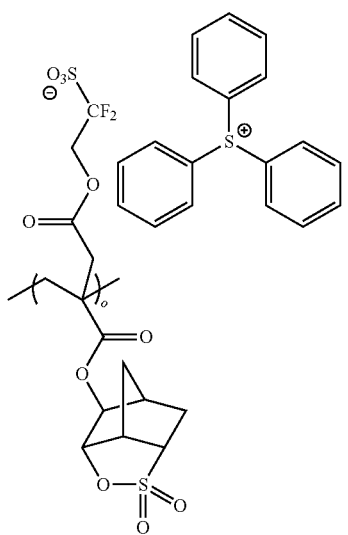
Polymeric Compound 3
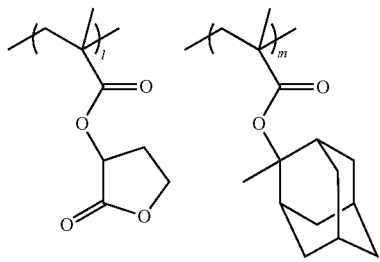
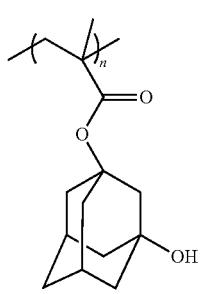
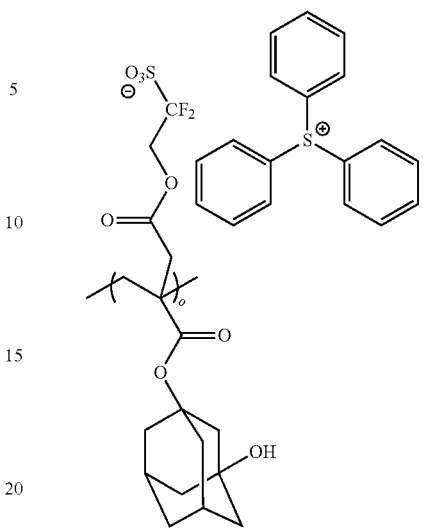
Polymeric Compound 4
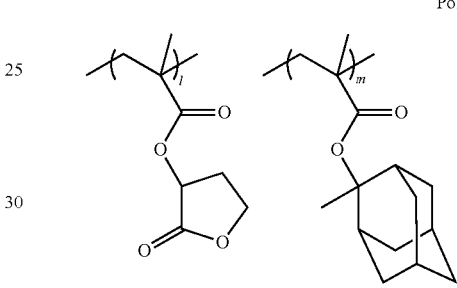
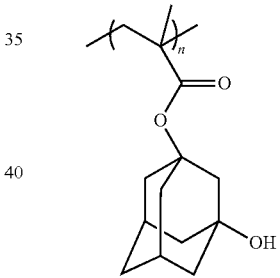
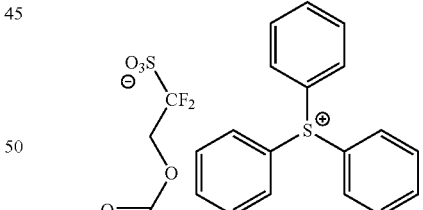
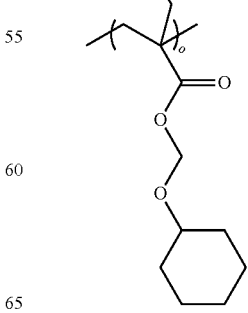

[Chemical Formula 79]
Polymeric Compound 5
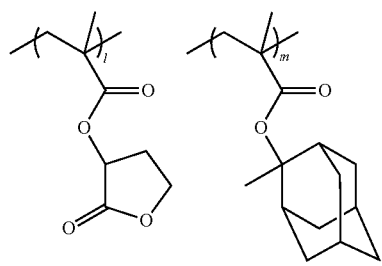
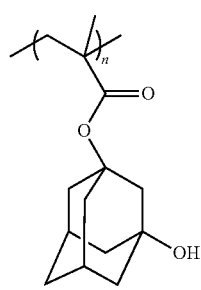
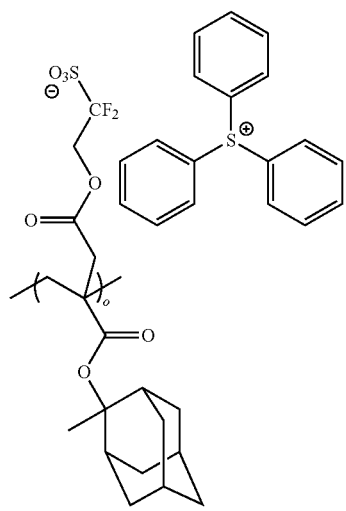
Polymeric Compound 6
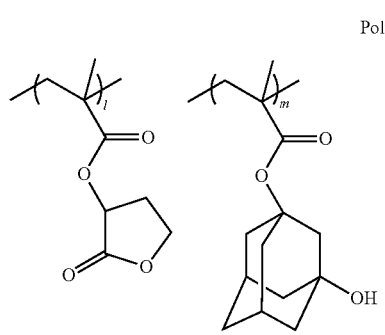
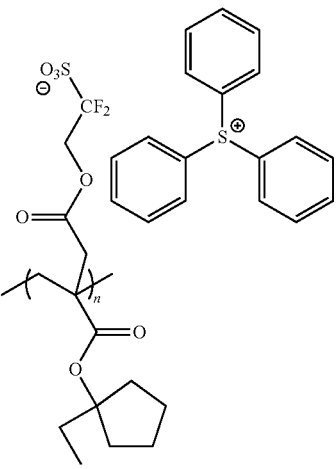
Polymeric Compound 7
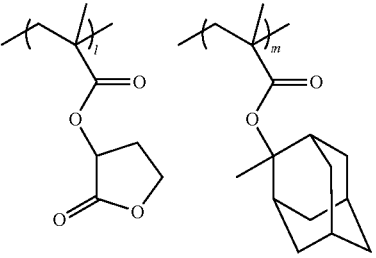
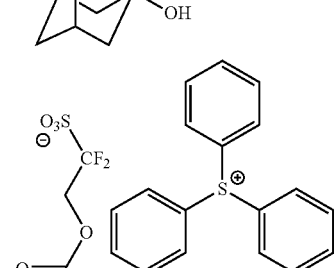

-continued

[Chemical Formula 80]

Polymeric Compound 8

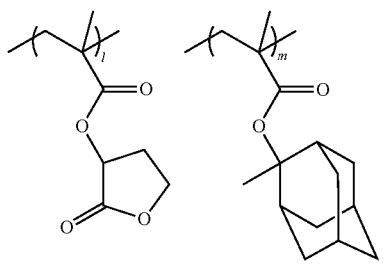

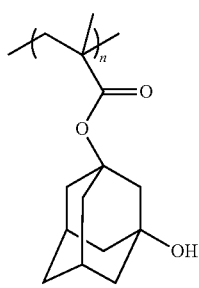

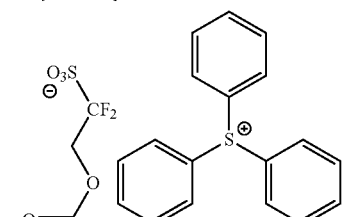

Polymeric Compound 9

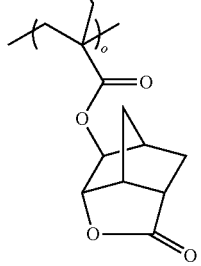

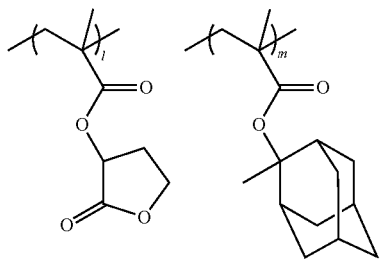

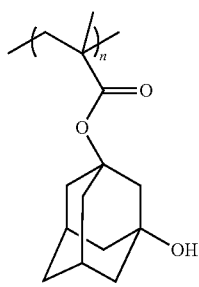

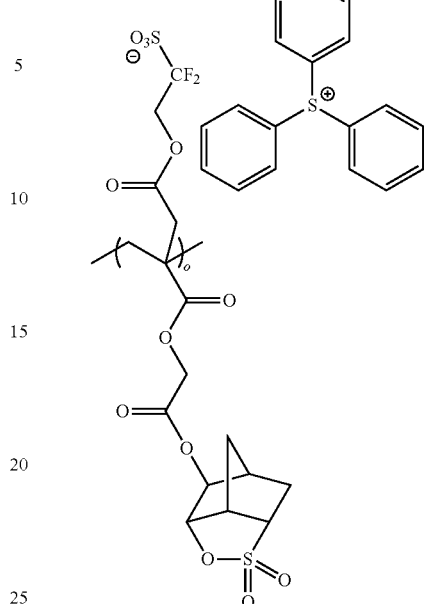

Examples 4 to 11, Comparative Examples 3 to 6

The components shown in Table 29 were mixed together and dissolved to obtain positive resist compositions.

TABLE 29

|  | Component (A) | Component (B) | Component (D) | Component (E) | Component (S) |
|---|---|---|---|---|---|
| Ex. 4 | (A)-2 [100] |  | (D)-1 [0.38] | (E)-1 [0.47] | (S)-1 [2,400] |
| Ex. 5 | (A)-3 [100] |  | (D)-1 [0.38] | (E)-1 [0.47] | (S)-1 [2,400] |
| Ex. 6 | (A)-4 [100] |  | (D)-1 [0.38] | (E)-1 [0.47] | (S)-1 [2,400] |
| Ex. 7 | (A)-5 [100] | (B)-7 [3.20] | (D)-1 [0.38] | (E)-1 [0.47] | (S)-1 [2,400] |
| Comp. Ex. 3 | (A)-6 [100] | (B)-7 [8.34] | (D)-1 [0.38] | (E)-1 [0.47] | (S)-1 [2,400] |
| Comp. Ex. 4 | (A)-7 [100] |  | (D)-1 [0.38] | (E)-1 [0.47] | (S)-1 [2,400] |
| Ex. 8 | (A)-2 [100] | (B)-6 [3.11] | (D)-1 [0.38] | (E)-1 [0.47] | (S)-1 [2,400] |
| Ex. 9 | (A)-3 [100] | (B)-6 [3.11] | (D)-1 [0.38] | (E)-1 [0.47] | (S)-1 [2,400] |
| Ex. 10 | (A)-4 [100] | (B)-6 [3.11] | (D)-1 [0.38] | (E)-1 [0.47] | (S)-1 [2,400] |
| Ex. 11 | (A)-5 [100] | (B)-7 [3.20] (B)-6 [3.11] | (D)-1 [0.38] | (E)-1 [0.47] | (S)-1 [2,400] |
| Comp. Ex. 5 | (A)-6 [100] | (B)-7 [8.34] (B)-6 [3.11] | (D)-1 [0.38] | (E)-1 [0.47] | (S)-1 [2,400] |
| Comp. Ex. 6 | (A)-7 [100] | (B)-6 [3.11] | (D)-1 [0.38] | (E)-1 [0.47] | (S)-1 [2,400] |

In Table 29, the reference characters indicate the following. Note that components (B)-6, (D)-1, (E)-1 and (S)-1 are the same as defined above. Further, the values in brackets [ ] indicate the amount (in terms of parts by weight) of the component added.

(A)-2: the abovementioned polymeric compound 1

(A)-3: the abovementioned polymeric compound 2 (Mw: 7,800; Mw/Mn: 1.81; l/m/n/o=36.8/40.4/19.5/3.3 (molar ratio))

(A)-4: a polymeric compound 3 (Mw: 6,800; Mw/Mn: 1.85; l/m/n/o=39.3/41.5/15.1/4.1 (molar ratio))

(A)-5: a polymeric compound which is the abovementioned polymeric compound 1 (in which Mw: 7,500; Mw/Mn: 1.76; l/m/n/o=40.5/37.1/20.5/1.9 (molar ratio))

(A)-6: a polymeric compound represented by the above formula (A)-1 (in which Mw: 7,000; Mw/Mn: 1.70; compositional ratio (molar ratio) is the same as that of (A)-1)

(A)-7: a polymeric compound (A)-7 shown below (Mw: 7,600; Mw/Mn: 1.79. In the chemical formula, the subscript numerals shown on the bottom right of the parentheses ( ) indicate the percentage (mol %) of the respective structural units.)

(B)-7: a compound (B)-7 shown below

[Chemical Formula 81]

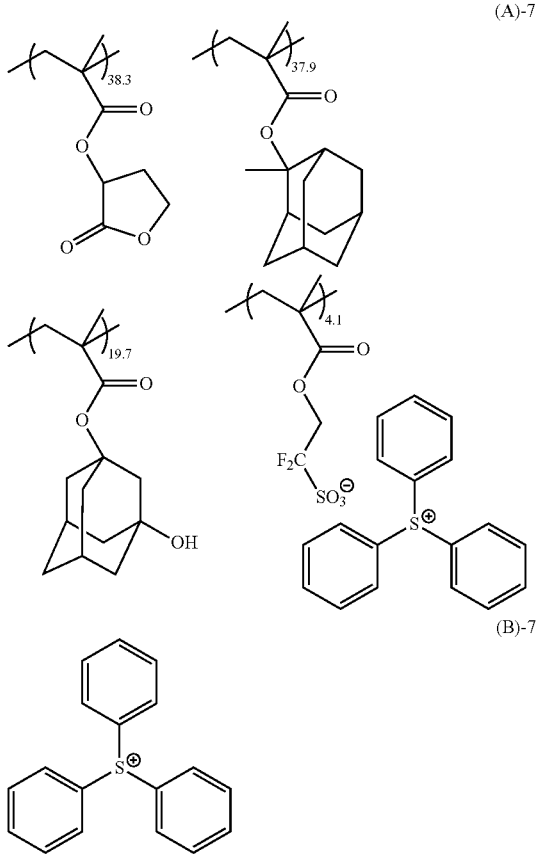

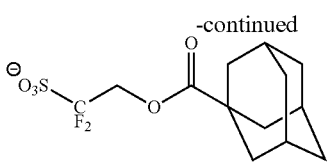

[Formation of Resist Pattern (2)]

A line and space resist pattern (hereafter, referred to as an "LS pattern") in which lines having a line width of 49 nm were spaced at equal intervals (pitch: 98 nm) was formed in the same manner as described above in the section [Formation of resist pattern (1)], with the exception that the resist compositions of Examples 4 to 11 and Comparative Examples 3 to 6 were used, and the PEB treatment was conducted at temperatures indicated in Table 30.

[Evaluation of Resist Pattern (2)]

The values of MEF, LWR and EL margin as well as the pattern shape were evaluated in the same manner as described above in the section [Evaluation of resist pattern (1)]. The results are shown in Table 30.

TABLE 30

|  | PEB (° C.) | MEF | LWR (nm) | EL (%) | Shape |
| --- | --- | --- | --- | --- | --- |
| Ex. 4 | 120 | 2.28 | 6.2 | 7.49 | Vertical |
| Ex. 5 | 130 | 2.38 | 6.4 | 7.35 | Vertical |
| Ex. 6 | 130 | 2.68 | 6.3 | 7.21 | Vertical |
| Ex. 7 | 100 | 2.31 | 6.6 | 7.87 | Vertical |
| Comp. Ex. 3 | 90 | 3.23 | 8.5 | 4.56 | Taper |
| Comp. Ex. 4 | 130 | 3.31 | 8.9 | 5.43 | T-Top |
| Ex. 8 | 120 | 2.30 | 6.3 | 7.45 | Vertical |
| Ex. 9 | 130 | 2.49 | 6.1 | 7.23 | Vertical |
| Ex. 10 | 130 | 2.81 | 6.1 | 7.32 | Vertical |
| Ex. 11 | 100 | 2.41 | 6.2 | 7.42 | Vertical |
| Comp. Ex. 5 | 90 | 3.32 | 8.0 | 4.12 | Taper |
| Comp. Ex. 6 | 130 | 3.42 | 8.0 | 5.34 | T-Top |

From the above results, it was confirmed that the resist compositions of Examples 4 to 11 were superior compared to the resist compositions of Comparative Examples 3 to 6 in that they exhibited excellent lithography properties (such as MEF, LWR and EL margin) and pattern shape.

Examples 12 to 15, Comparative Examples 7 and 8

The components shown in Table 31 were mixed together and dissolved to obtain positive resist compositions.

TABLE 31

|  | Component (A) | Component (B) | Component (D) | Component (E) | Component (F) | Component (S) |
| --- | --- | --- | --- | --- | --- | --- |
| Ex. 12 | (A)-2 [100] |  | (B)-6 [3.11] | (D)-1 [0.38] | (E)-1 [0.47] | (F)-1 [3.0] | (S)-1 [2,400] |
| Ex. 13 | (A)-3 [100] |  | (B)-6 [3.11] | (D)-1 [0.38] | (E)-1 [0.47] | (F)-1 [3.0] | (S)-1 [2,400] |
| Ex. 14 | (A)-4 [100] |  | (B)-6 [3.11] | (D)-1 [0.38] | (E)-1 [0.47] | (F)-1 [3.0] | (S)-1 [2,400] |
| Ex. 15 | (A)-5 [100] | (B)-7 [3.2] | (B)-6 [3.11] | (D)-1 [0.38] | (E)-1 [0.47] | (F)-1 [3.0] | (S)-1 [2,400] |
| Comp. Ex. 7 | (A)-6 [100] | (B)-7 [8.34] | (B)-6 [3.11] | (D)-1 [0.38] | (E)-1 [0.47] | (F)-1 [3.0] | (S)-1 [2,400] |
| Comp. Ex. 8 | (A)-7 [100] |  | (B)-6 [3.11] | (D)-1 [0.38] | (E)-1 [0.47] | (F)-1 [3.0] | (S)-1 [2,400] |

In Table 31, the reference characters indicate the following. Note that components (A)-2 to (A)-7, (B)-6 and (B)-7, (D)-1, (E)-1 and (S)-1 are the same as defined above. Further, the values in brackets [ ] indicate the amount (in terms of parts by weight) of the component added.

(F)-1: a polymeric compound (F)-1 shown below (Mw: 18,000; Mw/Mn: 1.5. In the chemical formula, the subscript numerals shown on the bottom right of the parentheses ( ) indicate the percentage (mol %) of the respective structural units.)

[Chemical Formula 82]

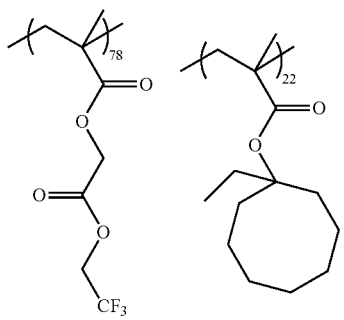

(F)-1

[Formation of Resist Pattern (3)]

A line and space resist pattern (hereafter, referred to as an "LS pattern") in which lines having a line width of 49 nm were spaced at equal intervals (pitch: 98 nm) was formed in the same manner as described above in the section [Formation of resist pattern (1)], with the exception that the resist compositions of Examples 12 to 15 and Comparative Examples 7 and 8 were used, the step of top coat formation was omitted, and the PEB treatment was conducted at temperatures indicated in Table 32.

[Evaluation of Resist Pattern (3)]

The values of MEF, LWR and EL margin as well as the pattern shape were evaluated in the same manner as described above in the section [Evaluation of resist pattern (1)]. The results are shown in Table 32.

TABLE 32

|  | PEB (° C.) | MEF | LWR (nm) | EL (%) | Shape |
|---|---|---|---|---|---|
| Ex. 12 | 120 | 2.41 | 6.5 | 7.55 | Vertical |
| Ex. 13 | 130 | 2.44 | 6.4 | 7.42 | Vertical |
| Ex. 14 | 130 | 2.79 | 6.8 | 7.38 | Vertical |
| Ex. 15 | 100 | 2.43 | 7.2 | 7.25 | Vertical |
| Comp. Ex. 7 | 90 | 3.35 | 8.4 | 4.31 | Taper |
| Comp. Ex. 8 | 130 | 3.56 | 9.1 | 5.98 | T-Top |

From the above results, it was confirmed that the resist compositions of Examples 12 to 15 were superior compared to the resist compositions of Comparative Examples 7 and 8 in that they exhibited excellent lithography properties (such as MEF, LWR and EL margin) and pattern shape.

Examples 16 to 21, Comparative Examples 9 and 10

The components shown in Table 33 were mixed together and dissolved to obtain positive resist compositions.

TABLE 33

|  | Component (A) | Component (B) | Component (D) | Component (E) | Component (S) |
|---|---|---|---|---|---|
| Ex. 16 | (A)-8 [100] |  | (D)-1 [0.38] | (E)-1 [0.47] | (S)-1 [2,400] |
| Ex. 17 | (A)-9 [100] |  | (D)-1 [0.38] | (E)-1 [0.47] | (S)-1 [2,400] |
| Ex. 18 | (A)-10 [100] |  | (D)-1 [0.38] | (E)-1 [0.47] | (S)-1 [2,400] |
| Ex. 19 | (A)-11 [100] |  | (D)-1 [0.38] | (E)-1 [0.47] | (S)-1 [2,400] |
| Ex. 20 | (A)-12 [100] |  | (D)-1 [0.38] | (E)-1 [0.47] | (S)-1 [2,400] |
| Ex. 21 | (A)-13 [100] |  | (D)-1 [0.38] | (E)-1 [0.47] | (S)-1 [2,400] |
| Comp. Ex. 9 | (A)-6 [100] | (B)-7 [8.34] | (D)-1 [0.38] | (E)-1 [0.47] | (S)-1 [2,400] |
| Comp. Ex. 10 | (A)-7 [100] |  | (D)-1 [0.38] | (E)-1 [0.47] | (S)-1 [2,400] |

In Table 33, the reference characters indicate the following. Note that components (A)-6 and (A)-7, (B)-7, (D)-1, (E)-1 and (S)-1 are the same as defined above. Further, the values in brackets [ ] indicate the amount (in terms of parts by weight) of the component added.

(A)-8: the abovementioned polymeric compound 4 (Mw: 6,900; Mw/Mn: 1.85; l/m/n/o=40.5/36.9/19.5/3.1 (molar ratio))

(A)-9: the abovementioned polymeric compound 5 (Mw: 7,200; Mw/Mn: 1.74; l/m/n/o=41.2/37.1/18.9/2.8 (molar ratio))

(A)-10: the abovementioned polymeric compound 6 (Mw: 8,200; Mw/Mn: 1.89; l/m/n=40.1/24.6/35.3 (molar ratio))

(A)-11: the abovementioned polymeric compound 7 (Mw: 7,200; Mw/Mn: 1.72; l/m/n/o=36.7/40.1/19.9/3.3 (molar ratio))

(A)-12: the abovementioned polymeric compound 8 (Mw: 7,500; Mw/Mn: 1.69; l/m/n/o=36.1/39.6/20.4/3.9 (molar ratio))

(A)-13: the abovementioned polymeric compound 9 (Mw: 7,500; Mw/Mn: 1.69; l/m/n/o=35.5/39.6/20.4/4.5 (molar ratio))

[Formation of Resist Pattern (4)]

A line and space resist pattern (hereafter, referred to as an "LS pattern") in which lines having a line width of 49 nm were spaced at equal intervals (pitch: 98 nm) was formed in the same manner as described above in the section [Formation of resist pattern (1)], with the exception that the resist compositions of Examples 16 to 21 and Comparative Examples 9 and 10 were used, the step of top coat formation was omitted, and the PEB treatment was conducted at temperatures indicated in Table 34.

[Evaluation of Resist Pattern (4)]

The values of MEF, LWR and EL margin as well as the pattern shape were evaluated in the same manner as described above in the section [Evaluation of resist pattern (1)]. The results are shown in Table 34.

TABLE 34

|  | PEB (° C.) | MEF | LWR (nm) | EL (%) | Shape |
|---|---|---|---|---|---|
| Ex. 16 | 100 | 2.32 | 6.5 | 7.28 | Vertical |
| Ex. 17 | 110 | 2.41 | 6.6 | 7.56 | Vertical |
| Ex. 18 | 90 | 2.31 | 6.1 | 7.78 | Vertical |

TABLE 34-continued

| | PEB (° C.) | MEF | LWR (nm) | EL (%) | Shape |
|---|---|---|---|---|---|
| Ex. 19 | 120 | 2.48 | 6.3 | 7.58 | Vertical |
| Ex. 20 | 120 | 2.59 | 7.1 | 6.92 | Vertical |
| Ex. 21 | 110 | 2.35 | 6.1 | 7.79 | Vertical |
| Comp. Ex. 9 | 90 | 3.23 | 8.5 | 4.56 | Taper |
| Comp. Ex. 10 | 130 | 3.31 | 8.9 | 5.43 | T-Top |

From the above results, it was confirmed that the resist compositions of Examples 16 to 21 were superior compared to the resist compositions of Comparative Examples 9 and 10 in that they exhibited excellent lithography properties (such as MEF, LWR and EL margin) and pattern shape.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A compound represented by general formula (1-1) shown below:

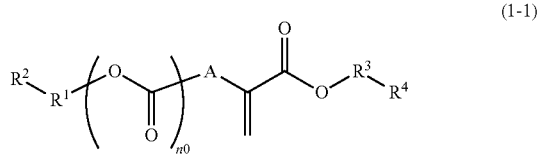

(1-1)

wherein each of $R^1$ and $R^3$ independently represents a single bond or a divalent linking group; A represents a divalent linking group; n0 represents 0 or 1, provided that, when n0 is 1, at least one of $R^2$ and $R^4$ is a group represented by any one of general formulae (1-an1), (1-an2) and (1-an3), and the other is an aliphatic cyclic group which may have a substituent, and when n0 is 0, $R^2$ is a group represented by any one of general formulae (1-an1), (1-an2) and (1-an3), and $R^4$ is an aliphatic cyclic group which may have a substituent:

wherein $Y^1$ represents a single bond or —$SO_2$—; $R^5$ represents a linear or branched monovalent hydrocarbon group of 1 to 10 carbon atoms, cyclic monovalent hydrocarbon group of 3 to 20 carbon atoms or monovalent hydrocarbon group of 3 to 20 carbon atoms having a cyclic partial structure which may be substituted with a fluorine atom; and $M^+$ represents an organic cation or a metal cation.

2. A polymeric compound comprising a structural unit derived from the compound of claim 1, wherein said $M^+$ represents an organic cation.

3. A resist composition comprising:
a base component (A') that generates acid upon exposure and exhibits changed solubility in a developing solution under action of acid,
wherein said base component (A') comprises a polymeric compound (A1') of claim 2.

4. An acid generator comprising the compound of claim 1, wherein said $M^+$ represents an organic cation.

5. A resist composition comprising:
a base component (A) which exhibits changed solubility in a developing solution under action of acid; and
an acid generator component (B) which generates acid upon exposure to irradiation with radiation,
wherein said acid generator component (B) comprises an acid generator (B1) of claim 4.

6. A method of forming a resist pattern, comprising:
forming a resist film on a substrate using the resist composition of claim 3 or 5;
conducting exposure to irradiation with radiation of said resist film; and
developing said resist film to form a resist pattern.

7. The compound according to claim 1, wherein n0 is 1, at least one of $R^2$ and $R^4$ is a group represented by any one of general formulae (1-an1), (1-an2) and (1-an3), and the other is an aliphatic cyclic group which may have a substituent, and A represents a divalent hydrocarbon group which may have a substituent.

8. The compound according to claim 1, wherein n0 is 1, at least one of $R^2$ and $R^4$ is a group represented by general formula (1-an1), and the other is an aliphatic cyclic group which may have a substituent.

9. The compound according to claim 1, wherein n0 is 1, $R^2$ is a group represented by general formula (1-an1), $R^4$ is an aliphatic cyclic group which may have a substituent, and A represents a divalent hydrocarbon group which may have a substituent.

10. The compound according to claim 1, wherein n0 is 0, $R^2$ is a group represented by any one of general formulae (1-an1), (1-an2) and (1-an3), and $R^4$ is an aliphatic cyclic group which may have a substituent.

11. The compound according to claim 1, wherein n0 is 0, $R^2$ is a group represented by any one of general formulae (1-an1), (1-an2) and (1-an3), $R^4$ is an aliphatic cyclic group which may have a substituent, and A represents a divalent hydrocarbon group which may have a substituent.

* * * * *